United States Patent [19]
Yamamoto et al.

[11] Patent Number: 6,059,719
[45] Date of Patent: May 9, 2000

[54] ENDOSCOPE SYSTEM

[75] Inventors: Tetsuya Yamamoto; Masahiro Ishikawa, both of Hachioji; Koichi Kawashima, Tokyo; Hideki Shimonaka, Hachioji; Koji Kanbara, Hachioji; Takayuki Suzuki, Hachioji; Hiroki Moriyama, Akishima; Yasuhito Kura, Hachioji; Akira Suzuki, Yamanashi, all of Japan

[73] Assignee: Olympus Optical Co., Ltd., Japan

[21] Appl. No.: 09/128,320

[22] Filed: Aug. 3, 1998

[30] Foreign Application Priority Data

| Aug. 6, 1997 | [JP] | Japan | 9-212133 |
| Jul. 2, 1998 | [JP] | Japan | 10-187801 |
| Jul. 2, 1998 | [JP] | Japan | 10-187802 |
| Jul. 2, 1998 | [JP] | Japan | 10-187803 |
| Jul. 2, 1998 | [JP] | Japan | 10-187804 |
| Jul. 2, 1998 | [JP] | Japan | 10-187805 |

[51] Int. Cl.$^7$ ............................................. A61B 1/00
[52] U.S. Cl. .................... 600/127; 600/104; 600/129; 606/1
[58] Field of Search ........................ 600/104, 106, 600/127, 129, 133; 606/1, 113, 170, 205

[56] References Cited

U.S. PATENT DOCUMENTS

| 5,368,014 | 11/1994 | Anapliotis et al. | 128/4 |
| 5,391,166 | 2/1995 | Eggers | 606/48 |
| 5,472,439 | 12/1995 | Hurd | 606/1 |
| 5,478,351 | 12/1995 | Meade et al. | 606/205 |
| 5,535,759 | 7/1996 | Wilk | 606/113 |
| 5,601,601 | 2/1997 | Tal et al. | 606/207 |
| 5,618,303 | 4/1997 | Marlow et al. | 606/205 |
| 5,630,782 | 5/1997 | Adair | 600/133 |
| 5,665,100 | 9/1997 | Yoon | 606/170 |
| 5,676,678 | 10/1997 | Schad | 606/170 |

FOREIGN PATENT DOCUMENTS

| 59-114511 | 8/1984 | Japan . |
| 64-80335 | 3/1989 | Japan . |
| 3-86315 | 8/1991 | Japan . |
| 9-215656 | 8/1997 | Japan . |

*Primary Examiner*—Linda C. M. Dvorak
*Assistant Examiner*—Brad C. Blaise
*Attorney, Agent, or Firm*—Ostrolenk, Faber, Gerb & Soffen, LLP

[57] ABSTRACT

An endoscope system in accordance with the present invention comprises a plurality of endoscope modules having different treatment instruments mounted therein, an endoscope to which the endoscope modules can be attached, and a coupling member fixed to the distal part of an insertion unit of the endoscope and used to make the plurality of endoscope modules freely exchangeable. The plurality of endoscope modules having the different treatment instruments mounted therein are freely exchangeable to be coupled to the distal part of the insertion unit of the endoscope.

69 Claims, 40 Drawing Sheets

| TYPE OF MODULE | CHARACTERS | COLOR |
|---|---|---|
| CLAMPS | HAJ | WHITE |
| BIOPSY FORCEPS | SEI | BLUE |
| SNARE | SUN | RED |
| LIGATURE | KES | YELLOW |

FIG.52
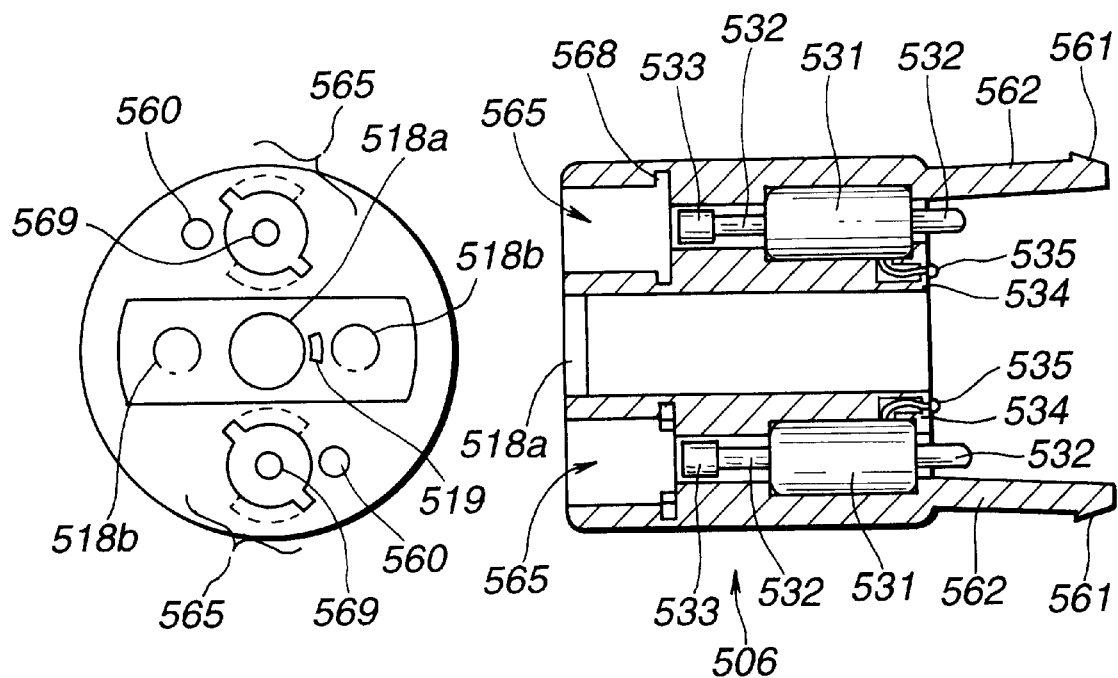
FIG.53A
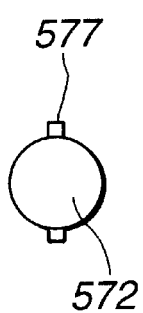
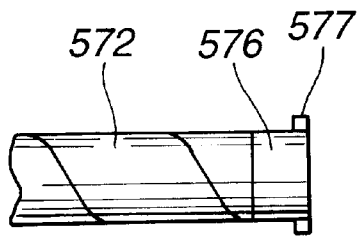
FIG.53B
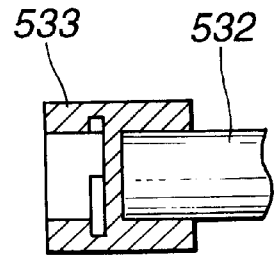

ENDOSCOPE SYSTEM

BACKGROUND OF THE INVENTION

1. Field of the Invention

The present invention relates to an endoscope system comprising an endoscope for use in an endoscopic examination or in surgery under endoscopic observation, and treatment instruments.

2. Description of the Related Art

In the past, endoscopes for medical use have been adopted widely. In such an endoscope, an elongated insertion unit thereof is inserted into a body cavity for observation of an intracorporeal organ or the like. If necessary, treatment instruments are inserted into a treatment channel in order to conduct various kinds of therapeutic treatments.

The treatment instruments are thin and long so that they can be inserted into the lumen of the treatment channel which lies through an endoscope and has a diameter of approximately 3 mm and a length of approximately 2 m. While the thin and long treatment instrument is being inserted into the elongated treatment channel in the endoscope, however, part of the instrument may be broken or damaged. For this reason, physicians must pay close attention to the treatment instrument to be inserted into the treatment channel.

For example, Japanese Unexamined Patent Publication No. 64-80335 has disclosed an endoscope for which treatment instruments are made of a material having appropriate elasticity or have distal ends thereof streamlined in order to prevent the treatment instruments from being damaged during insertion.

Moreover, for conducting a trans-endoscopic treatment, since the endoscope and treatment instruments are formed mutually independently, a physician must use both of his/her hands to handle the complex system of endoscope and treatment instruments. Alternatively, a plurality of people including paramedics must be called to assist in the handling of the endoscope and of the treatment instruments. Thus, expertise is needed. In some endoscopes, an operation unit for handling treatment instruments is coupled firmly to an operation unit for handling an endoscope in an effort to simplify handling of the endoscope and treatment instruments.

However, where the treatment instruments differ from traditional treatment elements such as by changing the material or streamlining its appearance, as described in the Japanese Unexamined Patent Publication No. 64-80335, no fundamental solution is provided. In particular, when a special material is used, it is hard to procure the material and the manufacturing process may be complex. The incorporation of such special materials is therefore unfavorable for mass-production and leads to an expensive treatment tool.

Moreover, when an endoscope and treatment instrument are coupled firmly to each other in order to simplify handling of the endoscope and treatment instrument, the operation unit for handling the endoscope and the operation unit for handling treatment instruments interfere with each other. This poses a problem of poor maneuverability.

Furthermore, when an elongated treatment instrument is post-processed, that is, cleared or sterilized after a treatment, a problem occurs in that it is hard to clean or the post-processing takes too much time. Moreover, when treatment instruments are stored or managed after the post-processing, since the treatment instruments are thin and long, a large storage space is needed.

SUMMARY OF THE INVENTION

An aspect of the present invention is to provide an endoscope system in which any treatment instrument can be located at a given position in an endoscope without being damaged.

Another aspect of the present invention is to provide an endoscope system in which any treatment instrument an be handled easily under endoscopic observation.

Another aspect of the present invention is to provide an endoscope system in which a treatment instrument can be cleaned satisfactorily after use.

Still another aspect of the present invention is to provide an endoscope system in which cleaned treatment instruments can be stored in a limited space.

Yet another aspect of the present invention is to provide an endoscope system in which a combination of a treatment instrument and endoscope can be identified easily.

Briefly, an endoscope system of the present invention comprises a plurality of endoscope modules having different treating means mounted therein, an endoscope to which the endoscope modules can be attached, and a coupling means fixed to the distal part of an insertion unit of the endoscope and used to make the plurality of endoscope modules freely exchangeable. The plurality of endoscope modules having the different treating means is freely exchangeable and attachable to the distal part of the insertion unit of the endoscope via the coupling means.

BRIEF DESCRIPTION OF THE DRAWINGS

FIG. 1 is a diagram for explaining an overall configuration of an endoscope system of the present invention;

FIG. 2 is a sectional view for explaining a coupling member of a ligation module, one of the endoscope modules to be attached to the endoscope of the endoscopic system shown in FIG. 1, for coupling the module to the distal part of the endoscope;

FIG. 3 is a diagram for explaining a structure of the operation unit on the endoscope;

FIG. 4 is a diagram for explaining a state in which the ligation module is attached to the distal part of the endoscope;

FIG. 5 is a diagram for explaining the operation of the endoscope having the ligation module attached thereto;

FIG. 6 is a diagram for explaining an application of the invention in which elastic rings are successively put on a lesion;

FIG. 7 is a diagram for explaining another structure of a coupling member of an incision module that is another one of the endoscope modules for coupling the module to the distal part of the endoscope;

FIG. 8 is an elevational view for explaining another structure of the operation unit on the endoscope;

FIG. 9 is a diagram for explaining a state in which the incision module has been attached to the distal part of the endoscope;

FIG. 10 is a diagram for explaining a state in which an incision module is located at a lesion in a body cavity;

FIG. 11 is a diagram for explaining an application in which a lesion is incised by the incision module;

FIG. 12 is a diagram for explaining another structure of a coupling member of an incision module, one of the endoscope modules, for coupling the module to the distal part of the endoscope;

FIG. 13 is diagram for explaining a clamping module which is another one of the endoscope modules;

FIG. 14 is a diagram for explaining a biopsy module which is another of the endoscope modules;

FIG. 15 is a diagram for explaining an example operation using the incision module of the present invention;

FIG. 16 is a diagram for explaining another structure of a coupling member of a biopsy module that is another one of the endoscope modules for coupling the module to the distal part of the endoscope;

FIG. 17 is a diagram for explaining a state in which the biopsy module is attached to the distal part of the endoscope;

FIG. 18 is a diagram for explaining the operation of the endoscope having the biopsy module attached thereto;

FIG. 20 is a diagram for explaining another structure of the distal part of the endoscope and of a module body;

FIG. 21 is a diagram showing the distal part of the endoscope as seen from the direction of arrow A in FIG. 20;

FIG. 23 is a diagram for explaining a structure of an endoscope module and of the distal part of the endoscope according to the sixth embodiment;

FIG. 24 is a diagram showing an operation unit located at a position at which a module-side connecting tool and endoscope-side connecting tool are coupled to each other;

FIG. 25 is a diagram for explaining a structure of the endoscope having a transmission wire enclosed in a wire passage tube and inserted in the endoscope, and a structure of an endoscope module according to the seventh embodiment;

FIG. 26 is an elevational view showing a structure of the operation unit on the endoscope according to the seventh embodiment;

FIG. 27 is a diagram for explaining a structure of a dilation module having a balloon and a structure of the distal part of the endoscope according to the eighth embodiment;

FIG. 28 is a diagram for explaining a state in which the dilation module is attached to the distal part of the endoscope;

FIG. 29 is a diagram for explaining the operation of the endoscope to which the dilation module is attached;

FIG. 30 is a diagram for explaining a structure of an endoscope module having biopsy forceps and a balloon and a structure of the distal part of the endoscope according to the ninth embodiment;

FIG. 31 is a diagram for explaining the operation of the endoscope having the endoscope module of FIG. 30 attached thereto;

FIG. 32A is a perspective view showing the appearance of an endoscope module according to the tenth embodiment;

FIG. 32B lists characters and colors for identifying different types of modules which are placed on the lateral circumference of a body member;

FIG. 33 is a diagram showing another configuration of the endoscope system;

FIG. 34 is a perspective view for explaining an incision module that is one of endoscope modules of the system shown in FIG. 33;

FIG. 35 is an explanatory sectional view showing a structure of the distal part of the endoscope and of an endoscope module according to an embodiment of the configuration shown in FIG. 33;

FIG. 36 is a diagram for explaining a structure of an endoscope system of the twelfth embodiment including endoscope modules which are freely detachably attachable to a plurality of endoscopes;

FIG. 37 is an elevational view showing the proximal parts of a transmission wire and tube extending from a treatment instrument insertion port of an operation unit;

FIG. 38 is a diagram showing a state in which an incision module is attached to the distal part of an endoscope of the twelfth embodiment;

FIG. 39 is a diagram for explaining the operation of the endoscope of the twelfth embodiment having an incision module attached to the distal part thereof;

FIG. 40 is a diagram for explaining another structure of an endoscope system including endoscope modules to be freely detachably attached to a plurality of endoscopes;

FIG. 41 is a diagram showing a state in which an incision module is attached to the distal part of an endoscope of the thirteenth embodiment;

FIGS. 45 to 51 are diagrams for explaining a sixteenth embodiment of the present invention;

FIG. 45 is a diagram for explaining another configuration of an endoscope system;

FIG. 46 is a diagram for explaining clamps that are an example of a treatment member according to the sixteenth embodiment;

FIG. 47A is a diagram showing biopsy forceps;

FIG. 47B is a diagram showing clamps;

FIG. 47C is a diagram showing a lithotriptor;

FIG. 47D is a diagram showing a diathermic snare;

FIG. 48 is a diagram for explaining the structure of a module body of the sixteenth embodiment;

FIG. 49 is a diagram for explaining a state in which the module body of FIG. 48 is attached to the distal part of an insertion unit;

FIG. 50A is a diagram showing the module body having the treatment member mounted therein;

FIG. 50B is a diagram for explaining the distal part of the endoscope of the sixteenth embodiment;

FIG. 50C is a diagram showing a state in which the module body having the treatment member mounted therein as shown in FIG. 50A has been attached to the distal part of the endoscope shown in FIG. 50B;

FIG. 51A is a diagram showing a state in which the treatment member is attached to the module body;

FIG. 51B is a diagram showing the module body having the treatment member located at a proper position in the module body;

FIGS. 52 and 53 are diagrams for explaining the seventeenth embodiment of the present invention;

FIG. 52 is a diagram for explaining another structure of a module body according to the present invention;

FIGS. 53A and 53B are diagrams showing another structure of a treatment instrument placement member;

FIG. 53A is a diagram for explaining the structure of the proximal part of a treatment member;

FIG. 53B is a diagram for explaining the structure of a coupling member;

FIG. 57A is a diagram for explaining a treatment instrument placement member and module body according to the eighteenth embodiment;

FIG. 57B is a detailed diagram of a locking member;

FIG. 57C is a diagram showing a state in which the treatment instrument placement member of FIG. 57A is dismounted from the module body; and FIG. 57D is a diagram showing a state in which the treatment instrument placement member of FIG. 57A has been dismounted from the module body.

DESCRIPTION OF THE PREFERRED EMBODIMENTS

Referring to FIGS. 1 to 6, a first embodiment of the present invention will be described below.

Figure 1:
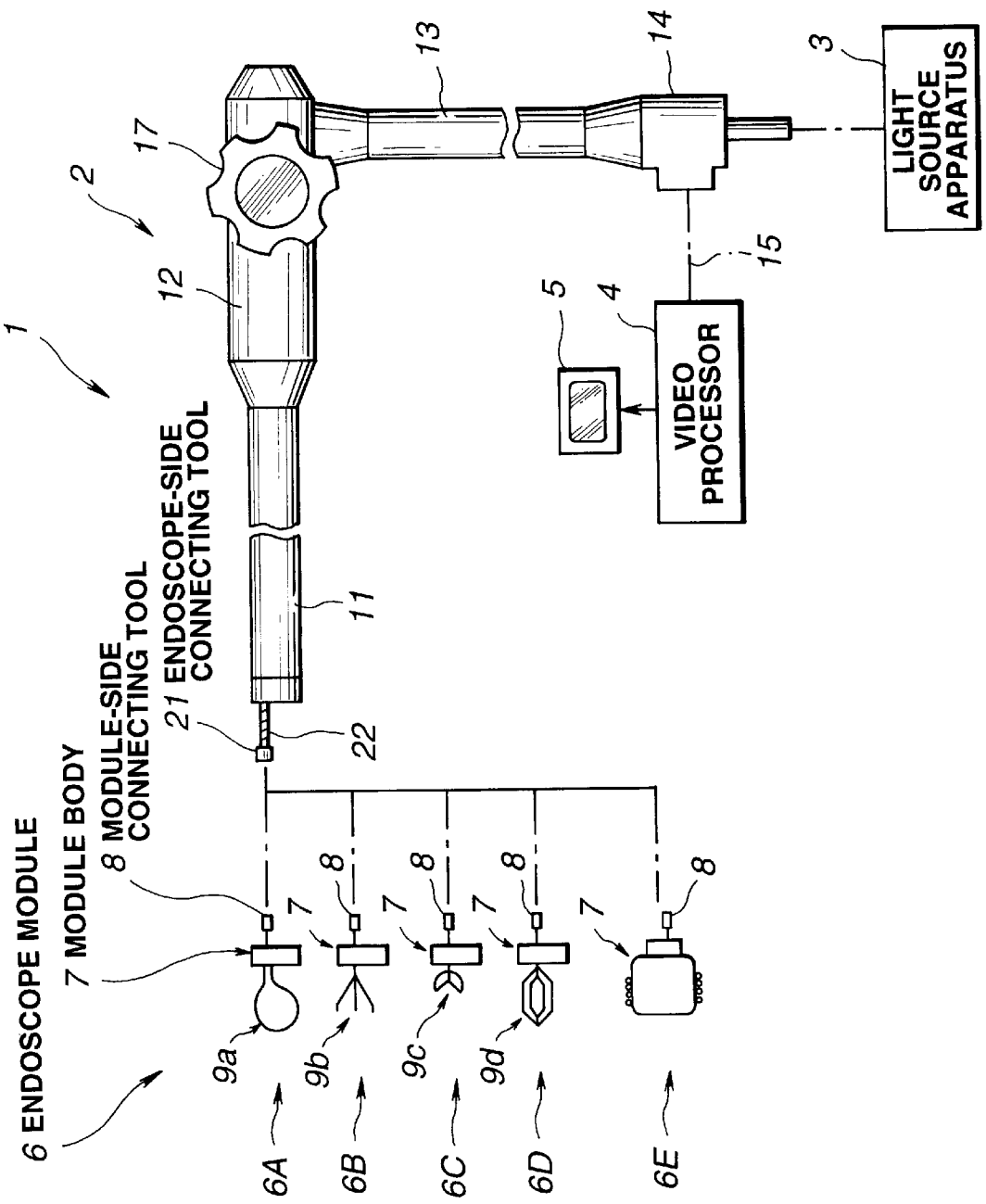
FIGS. 1 to 6 are diagrams for explaining a first embodiment of the present invention.

As shown in FIG. 1, an endoscope system 1 of this embodiment comprises an electronic endoscope (hereinafter an endoscope) 2, a light source apparatus 3, a video processor 4, a monitor 5, and a plurality of endoscope modules 6 each having a treatment instrument, which is a treatment instrument, which is a treating means, and is freely detachably attachable to the endoscope 2.

The endoscope 2 includes an insertion unit 11 that is elongated and is flexible, an operation unit 12 communicating with the proximal end of the insertion unit 11, and a universal cord 13 extending from the lateral side of the operation unit 12 and having flexibility. A connector 14 to be coupled to the light source apparatus 3 is a freely detachable fashion is spliced to an end of the universal cord 13. A signal cord 15 is extending from the lateral side of the connector 14, and spliced to a video processor 4 via an electric connector that is not shown. A monitor 5 for displaying an endoscopic image is connected to the video processor 4.

The endoscope modules 6 each include a module body 7 having a coupling member that serves as a coupling means for coupling the module body to the endoscope 2, and a treating means that is mounted in the module body 7 and is differentiated according to the purpose of the treatment or examination procedure. The treating means is provided with a module-side connecting tool 8 that is shaped like a bar. The treating means is connected to the endoscope 2 via the module-side connecting tool 8.

Figure 2:
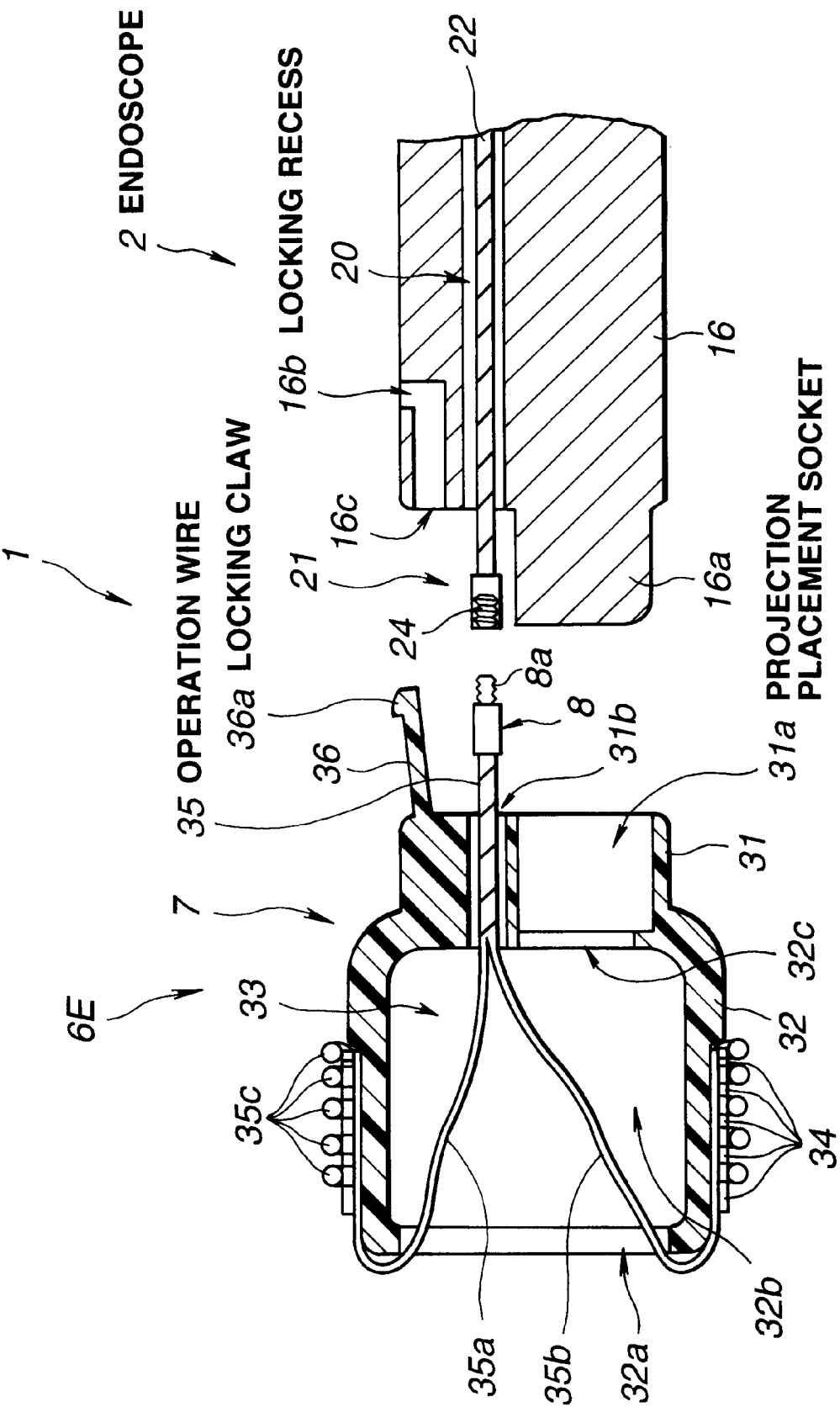

As the treating means, for example, an incision module 6A having a snare 9a, a clamping module 6B having a clamping member 9b, a biopsy module 6C having biopsy forceps 9c, a collection module 6D having a basket-shaped collector 9d, and a ligation module 6E shown in FIG. 2 are available.

The module body 7 has an insulator coated over the outer surface of the body . Alternatively, the whole module body 7 is made of a resin material that acts as an insulator. This structure is intended to prevent an examining physician from undergoing electrical shock due to current leakage occurring during a treatment procedure in which a high-frequency current is employed.

The distal part of the insertion unit 11 of the endoscope 2 is formed at a distal part 16 (FIG. 2) that serves as a coupling means to which the module body 7 of the endoscope module 6 is coupled. The distal part 16 is provided with a cylindrical endoscope-side connecting tool 21 that serves as a connecting means to be coupled with a module-side connecting tool 8 included in the endoscope module 6. A transmission wire 22 serving as an operation force transmitting means extends from the proximal end of the endoscope-side connecting tool 21. The transmission wire 22 is coupled to an operation knob 17 that is mounted on the operation unit 12 and serves as a traction means.

When the operation knob is handled with the module-side connecting tool 8 and endoscope-side connecting tool 21 coupled to each other the transmission wire 22 advances or withdraws. Thus, the treating means (for example, the snare 9a) of the endoscope module 6 attached to the distal part 16 is handled.

As shown in FIG. 2, an endoscope system 1 of this embodiment comprises an endoscope 2, and a ligation module 6E that is one of endoscope modules 6 to be freely detachably attached to the distal part 16 of the endoscope 2 and has a ligature 33 as a treating means.

The distal part 16 of the endoscope 1 includes a distal projection 16a serving as a coupling means for enabling freely detachable attachment of the ligation module 6E, a coupling hole 16c including a locking recess 16b, and an operation channel 20 through which the transmission wire 22 for transmitting an operation force is provided to be able to advance or withdraw freely. A female screw 24 is threaded on the inner circumference of the endoscope-side connecting tool 21 fixed to the distal end of the transmission wire 22.

The ligation module 6E is made of a hard transparent resin material and is substantially convex in shape. The ligation module 6E consists of a module body 7 including a coupling member 31 that has a smaller diameter than that of the whole ligation module 6E and is shaped to oppose the distal part 16 of the endoscope 2, and a cap 32 having a bit larger diameter than the coupling member 31, and the ligature 33 serving as a treating means and including ligation elastic rings 34 placed on the outer circumference of the cap 32 and a treatment instrument operation wire (hereinafter an operation wire) 35.

A module-side connecting tool 8 serving as a connecting means and operation force transmitting means is fixed to the proximal end of the operation wire 35 A male screw portion 8a to be engaged with the female screw 24 of the endoscope-side connecting tool 21 is threaded on the proximal part of the module-side connecting tool 8.

The cap 32 of the ligation module 6E is provided with an opening 32a and a treatment hollow 32b. A lesion can be placed in the treatment hollow 32b through the opening 32a.

The coupler member 31 is provided with a projection placement socket 31a into which the distal projection 16a of the distal part 16 is fitted, a wire passage hole 31b through which the operation wire 35 is passed so that it can advance or withdraw freely, and an attachment jut 36 having a locking claw 36a formed at the proximal end thereof, which serves as a coupling means to be fitted into the coupling hole 16c. The wire passage hole 31b communicates with the treatment hollow 32b. The projection placement socket 31a communicates with the treatment hollow 32b via a communication aperture 32c.

The operation wire 35 is formed by twisting a plurality of wires 35a and 35b. The operation wire 35 is bifurcated into the wires 35a and 35b within the treatment hollow 32b after passing through the wire passage hole 31b. The two branch wires 35a and 35b have the distal parts thereof placed on the outer circumference of the cap 32.

The distal parts of the wires 35a and 35b are each provided with a plurality of inductors 35c. The elastic rings 34 are each placed between adjoining inductors 35c with the distal parts of the wires 35a and 35b having the inductors 35c placed on the outer circumference of the cap 32.

Figure 3:
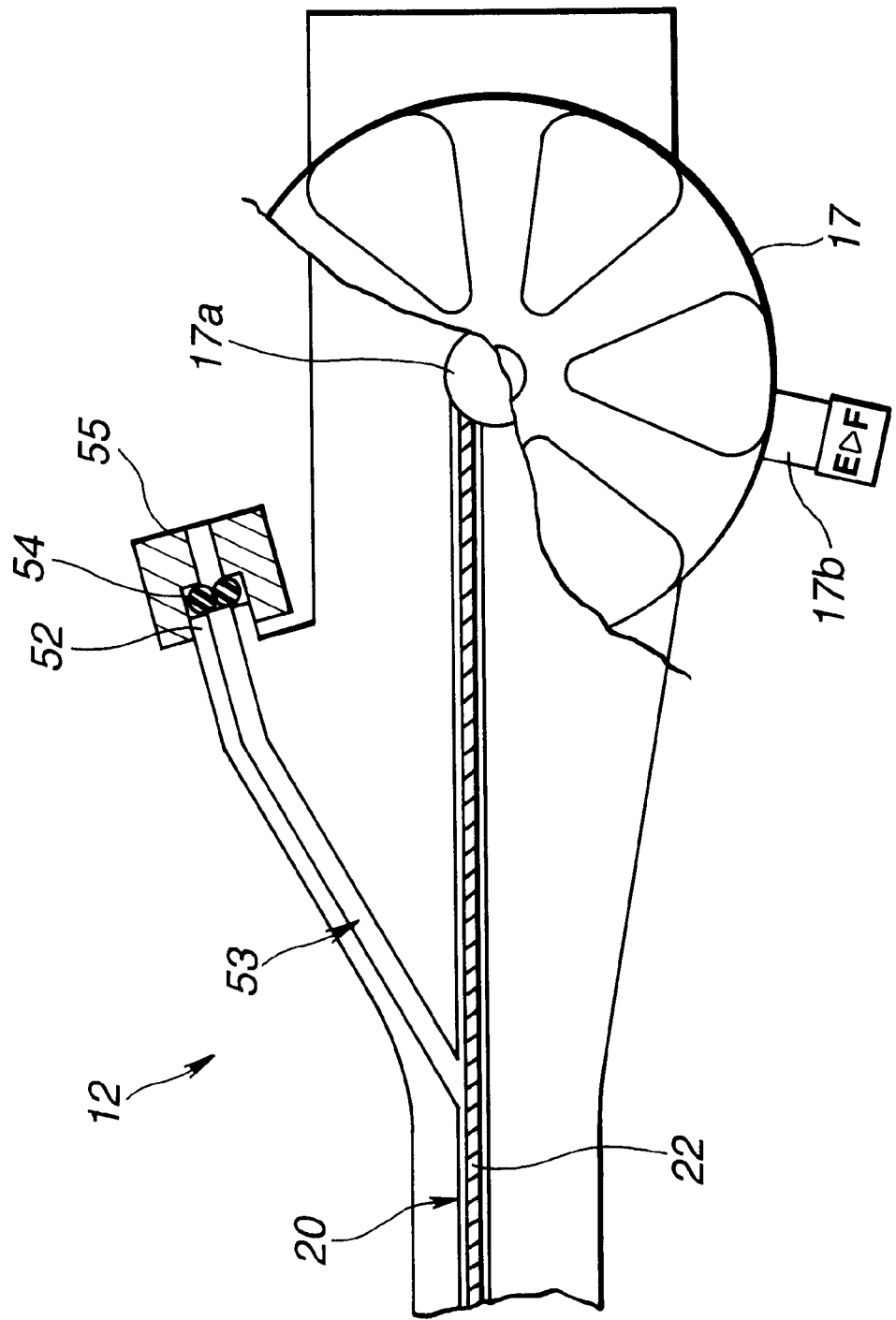

As shown in FIG. 3, an operation channel 20 formed in the distal part 16 reaches the operation unit 12 of the endoscope 1. The proximal end of the transmission wire 22 disposed in the operation channel 20 is fixed to a freely rotatable shaft 17a of the operation knob 17. The operation knob 17 is mounted on the operation 12 and serves as a handling means used to generate an operation force with which the treating means of the endoscope module 6 is handled. The operation knob 17 is provided with a locking knob 17b that is a locking mechanism capable of setting the operation knob selectively to a locked state or unlocked state.

By turning the operation knob 17, the transmission wire 22 can be advanced or withdrawn. The transmission wire 22 that advances or withdraws can be locked at a desired position by handling the locking knob 17b. Thus, a handled state can be retained.

The operation channel 20 communicates with an aeration/perfusion channel 53, which has an opening on the lateral side of the operation unit 12, at the middle thereof. A base 55 having a packing 54 fitted therein is attached to an opening end 52. The base 55, aeration/perfusion channel 53, and operation channel 20 constitute an aeration/perfusion channel for routing a liquid or gas.

The endoscope 2 includes optical lenses for illumination and observation a light transmitting means for enabling viewing of an optical image at the proximal end of the endoscope and which is input through the observation optical lens, and a bending portion for angling the distal part in a desired direction, though these components are not illustrated. An angling knob (not shown) used to angle the bending portion is mounted near the operation knob 17 on the operation unit 12.

The operations of the endoscope system 1 having the foregoing components will be described below.

Figure 4:
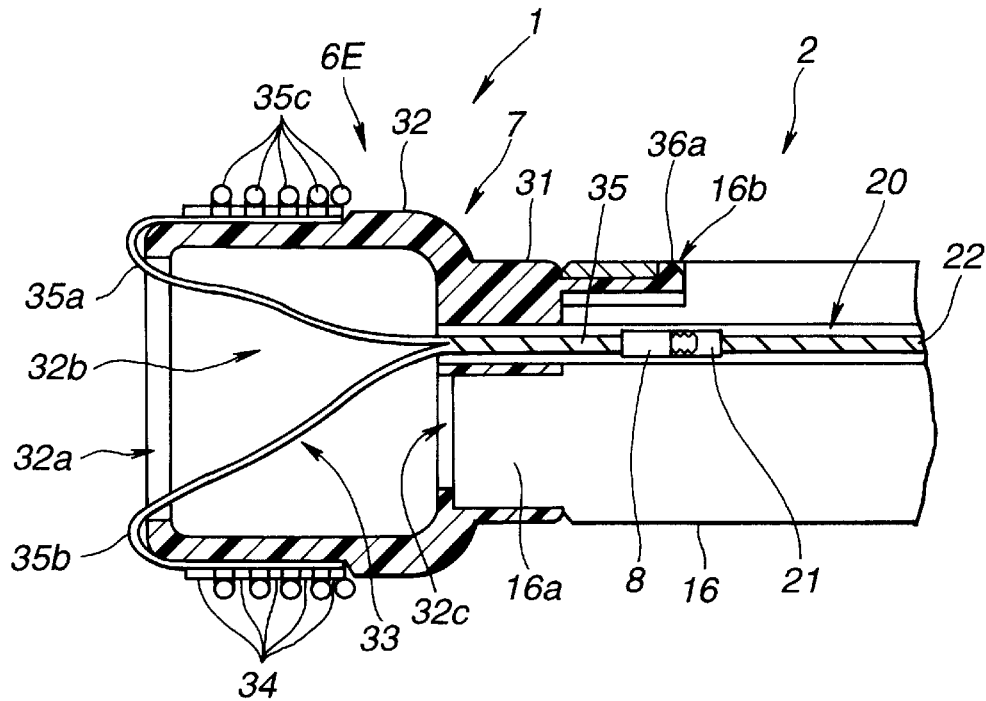

Before the endoscope 2 is inserted into a body cavity, the ligation module 6E to be attached to the distal part 16 of the endoscope 2 is picked up from among the plurality of endoscope modules 6 stowed in a storage box or the like. The female screw 24 of the endoscope-side connecting tool 21 fixed to the distal end of the transmission wire 22 disposed in the endoscope 2 is engaged firmly with the male screw portion 8a of the module-side connecting tool 8 fixed to the proximal end of the operation wire 35 in the ligation module 6E. Thereafter, the attachment jut 36 of the module body 7 is fitted into the coupling hole 16c. The distal projection 16a and projection placement socket 31a are aligned with each other. The ligation module 6E is then moved so that it will be attached to the endoscope 2. The distal projection 16a is then fitted into the projection placement socket 31a, and the locking claw 36a is engaged with the locking recess 16b. This causes the ligation module 6E to be, as shown in FIG. 4, located and securely locked at a given position in the distal part 16 of the endoscope 2.

Thereafter, the ligation module 6E is attached to the distal part 16. The endoscope 2 in which the operation knob 17 is locked using the locking knob 17b is inserted to a position near a region to be examined in a body cavity. The endoscope 2 is then moved so that the opening 32a located at the distal end of the cap 32 of the ligation module 6E will be opposed to a lesion 37 (FIG. 5) in the body cavity.

Thereafter, a suction unit that is not shown is used to carry out suction through the base 55 attached to the opening end 52 of the operation unit 12 of the endoscope 2. This allows the air in the body cavity to be sucked through the aeration/perfusion channel composed of the base 55, aeration/perfusion channel 53, and operation channel 20. Consequently, the lesion 37 is suctioned into the treatment hollow 32b.

Figure 5:
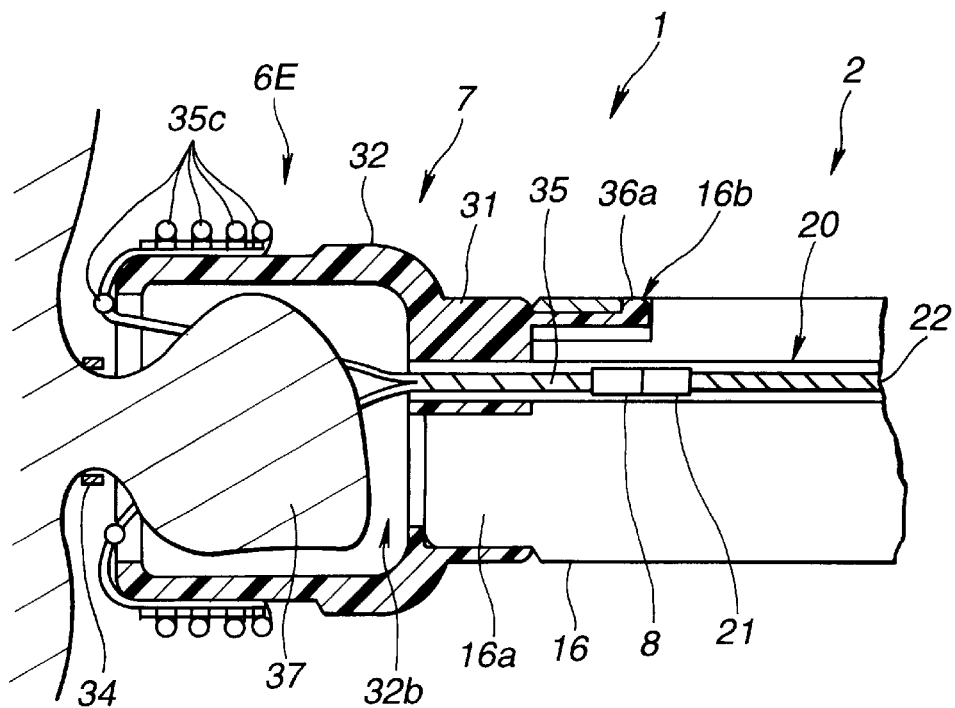

The locking knob 17b mounted on the operation unit 12 of the endoscope 2 is set to an unlocked-state position. Thereafter, the operation knob 17 is handled in order to retract the transmission wire 22. This causes the transmission wire 22 to move toward the operation unit 12. The operation wire 35 coupled to the transmission wire 22 is then moved in the same direction. With the movement of the operation wire 35, the inductors 35c formed in the distal parts of the wires 35a and 35b move. This cause the elastic rings 34 placed on the outer circumference of the cap 32 to move together with the inductors 35c. The leading one of the elastic rings 34 then comes off from the distal end of the cap 32, hereby the cap 32 contracts. Consequently, the root of the lesion 37 suctioned into the treatment hollow 32b is, as shown in FIG. 5, ligated due to an elastic force exerted by the elastic ring 34. The locking knob 17b is then re-set to the locked-state position.

Figure 6:
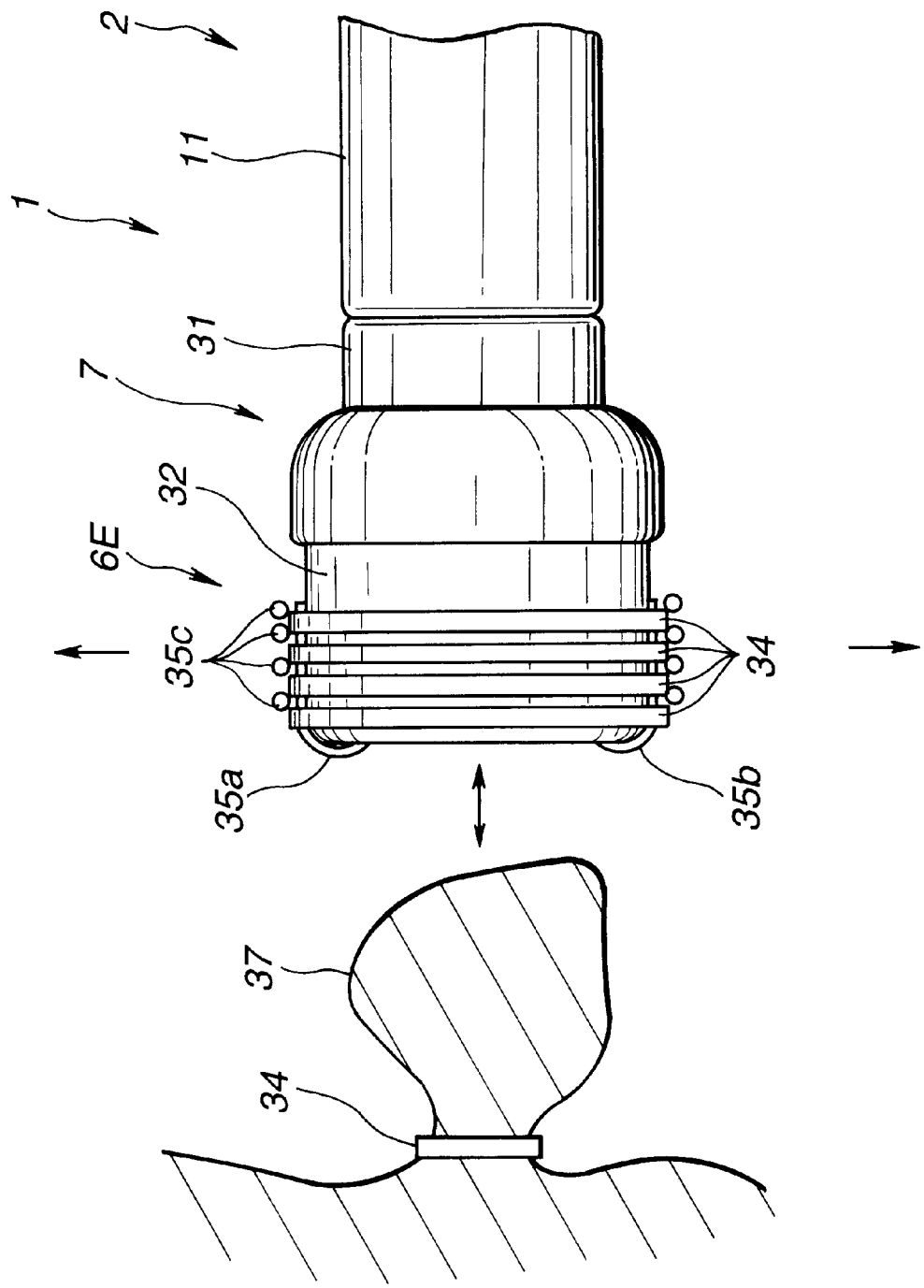

The endoscope 2, as shown in FIG. 6, can be moved in any of the directions indicated by the arrows, but is not pulled out of the body. The endoscope 2 is thus opposed to a different lesion 37. The foregoing handling sequence is repeated, whereby a plurality of lesions can be ligated with the elastic rings 34.

Moreover, when a treatment other than ligation is to be carried out next, the endoscope 2 is removed from the body cavity. The locking claw 36a that is engaged with the locking recess 16b of the coupling hole 16c is held down. Meanwhile, the ligation module 6E is moved in a direction in which it is separated from the distal part 16 of the endoscope 2. Thereafter, the endoscope module 6 having a different treating means is attached to the distal part 16 in order to conduct treatment. After the treatment is completed, the endoscope module 6 is separated from the distal part 16. The endoscope 2 and endoscope module 6 which have been used for the treatment are cleaned and sterilized.

As mentioned above, instead of inserting an elongated treatment instrument into a treatment channel in an endoscope, a small-sized endoscope module having a treating means is freely detachably attached to the distal part of the endoscope. Moreover, a transmission wire provided in the endoscope and a handling means for handling the treating means included in each module are coupled firmly with each other using connecting means. The treatment instrument can therefore be placed easily at a desired position in the endoscope without any damage.

Moreover, the same structure is used as coupling structure of endoscope modules for coupling them to an endoscope. Consequently, the endoscope modules are readily exchangeable so as to be attached easily to the endoscope according to the specific requirements of treatment and examination. This means that an endoscope module associated with the requirements of a particular treatment or examination can be selected and attached to the endoscope for the examination or treatment.

Furthermore, since the endoscope modules are freely detachably attachable to the distal part of the endoscope, the treatment instruments can be cleaned or sterilized efficiently. Moreover, due to their small size, the cleaned or sterilized endoscope modules can be stored in a limited space. This leads to enhanced maintenance and management of the treatment instruments.

Moreover, an operation knob used to handle the treating means of an endoscope module is located near an angling knob or the like mounted on the operation unit of the endoscope. The endoscope and the treating means included in the endoscope module can thus be handled easily.

Furthermore, since a locking knob used to set the operation knob selectively to the locked state or unlocked state is provided, the operation knob can be prevented from moving unintentionally.

Referring to FIGS. 7 to 11, a second embodiment of the present invention will be described below.

This embodiment is different from the first embodiment in the structure of a module body, and the structure of a coupling member of the module body for coupling the module body to an endoscope. The other components are identical to those of the first embodiment. The same reference numerals will be assigned to the same members. The descriptions of those members will be omitted.

Figure 7:
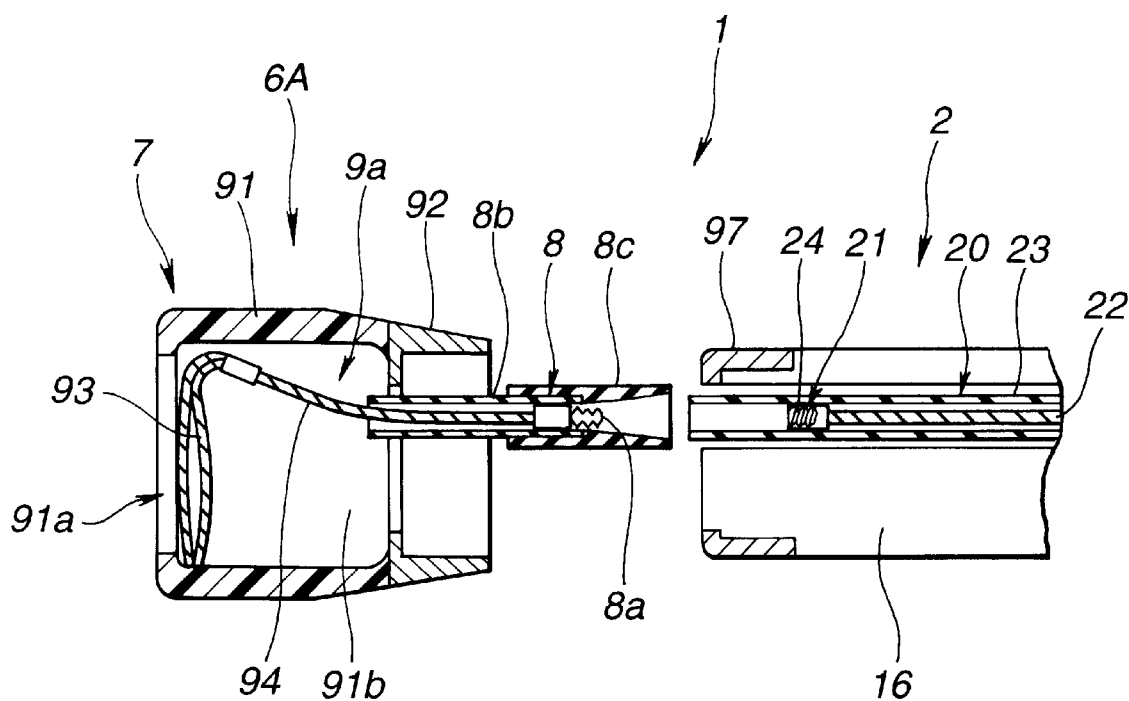
FIGS. 7 to 11 are diagrams for explaining a second embodiment of the present invention.

As shown in FIG. 7, an incision module 6A that is one of endoscope modules 6 of this embodiment is taken for instance. A module body of the incision module 6A consists of a main unit 91 made of a hard resin material and shaped substantially like a pipe, a first magnet 92 fixed to the proximal end of the main unit 91 for serving as a coupling means, and shaped substantially like a pipe, and an incision device 9a having an incising member 93 shaped substantially like a circular loop as the distal part thereof.

An opening 91a is formed on the distal side of the main unit 91. A lesion can be placed in a treatment hollow 91b through the opening 91a.

The incision device 9a consists of a snare 94 forming the incising member 93 shaped substantially like a loop, a treatment operation tube 8b which is mounted in the main unit 91 so that it can freely advance or withdraw and with which an advancement or withdrawal of the transmission wire 22 may be aligned, and a coupling member 8c having the distal part thereof fitted on the proximal part of the treatment operation tube 8b, and having the inner circumference of the proximal portion thereof tapered from the proximal end thereof toward the distal side thereof or formed as a tapered portion.

Moreover, a second magnet 97 serving as a coupling means is mounted on the distal part 16 of the endoscope 2 so that it can be turned on the outer circumference of the distal part 16.

Moreover, an operation tube 23 extends through the operation channel 20 so that it can advance or withdraw freely. The transmission wire 22 extends through the operation tube 23.

Figure 8:
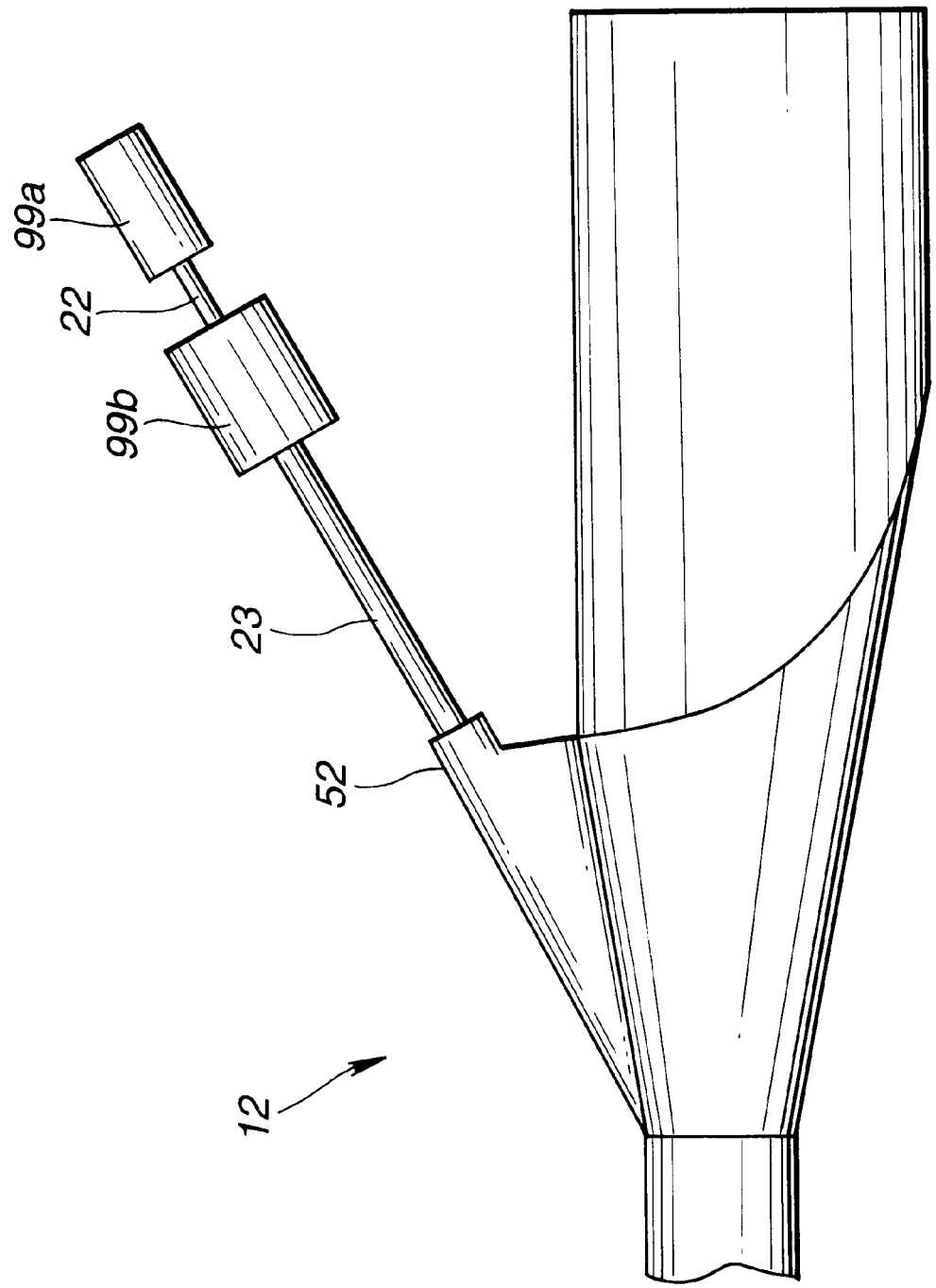

As shown in FIG. 8, a first operation handle 99a to which the proximal end of the transmission wire 22 is coupled and which exerts a first operation force, and a second operation handle 99b to which the proximal end of the operation tube 23 is coupled and which exerts a second operation force are located on an extension from the opening end 52 of the operation unit 12 of the endoscope 2. The transmission wire 22 and operation tube 23 can be advanced or withdrawn by advancing or withdrawing the first handle 99a and second handle 99b, respectively.

As mentioned above, the distal part 16 of the endoscope 2 of this embodiment is provided with neither the distal projection 16a nor the coupling hole 16c.

The operation of the endoscope system 1 including the incision module 6A and endoscope 2 will be described below.

Before the endoscope 2 is inserted into a body cavity, the incision module 6A is attached to the distal end of the endoscope 2. At this time, the endoscope-side connecting tool 21 fixed to the distal end of the transmission wire 22 is extended out from the operation tube 23 in the operation channel 20. The module-side connecting tool 8 fixed to the back end of the incision device 9a is extended out from the proximal end of the coupling member 8c. The male screw portion 8a of the module-side connecting tool 8 is engaged with the female screw 24 of the endoscope-side connecting tool 21. Thus, the transmission wire 22 and snare 94 are securely coupled with each other.

Thereafter, the distal part of the operation tube 23 is press-fitted in the tapered portion of the coupling member 8c of the incision module 6A. This causes the operation tube 23 and treatment operation tube 8b to be coupled firmly to each other via the coupling member 8c.

Figure 9:
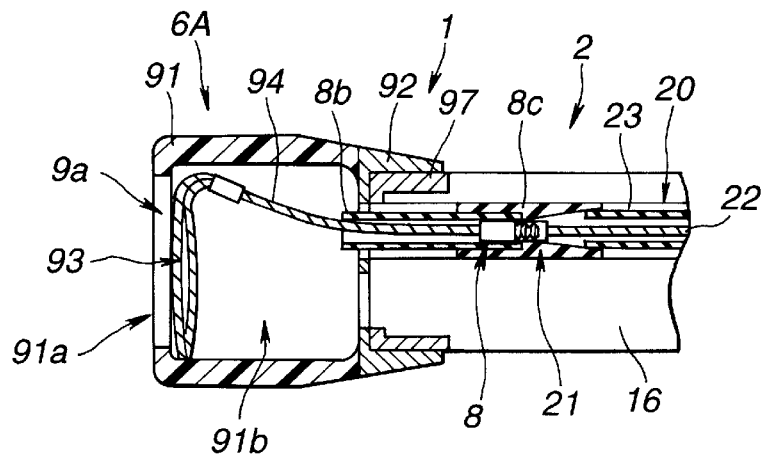

The second magnet 97 mounted on the distal part 16 of the endoscope 2 is then fitted into the through hole of the first magnet 92 of the incision module 6A. Due to the magnetic force exerted by the magnets 92 and 97, as shown in FIG. 9, the incision module 6A and endoscope 2 are securely fixed to each other . In this state, by following the same sequence as that in the first embodiment, the endoscope 2 is positioned at a desired location in a body cavity.

Figure 10:
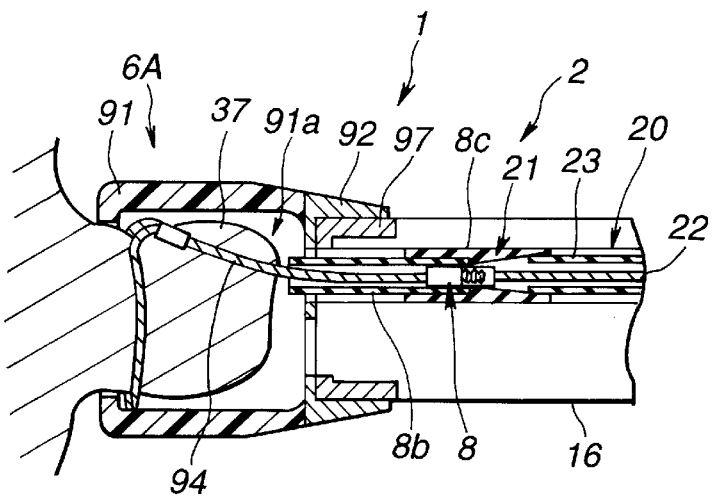

Thereafter, the lesion 37 is, as shown in FIG. 10, pulled into the treatment hollow 91b by utilizing suction force exerted through a suction channel (not shown) extending through the endoscope 2. At this time, the snare 94 is manipulated so that the incising portion 93 will be shaped like a loop along the opening 91a of the main unit 91. Thus, the suctioned lesion 37 is snared by the incising member 93.

In this state, the second handle 99b on the operation unit 12 is advanced. This causes the treatment operation tube 8b to thrust forward. The snare 94 is then pulled relatively into the treatment operation tube 8b. The root of the lesion 37 is substantially fastened by the snare 94.

Figure 11:
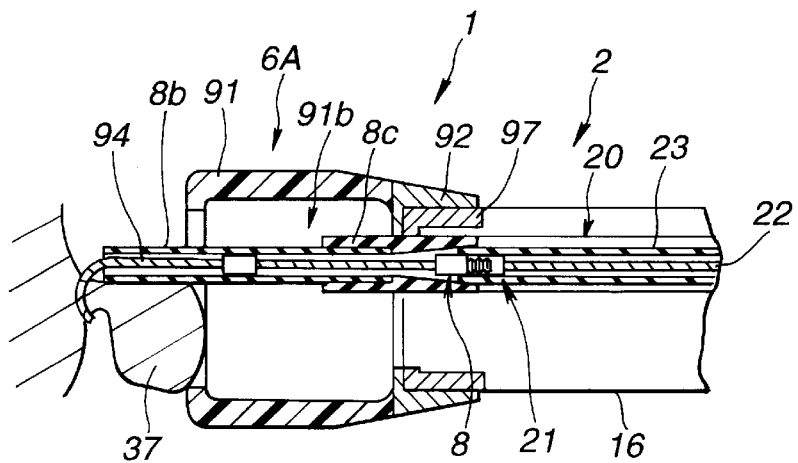

Successively the first handle 99a is withdrawn proximally. This causes, as shown in FIG. 11, the snare 94 to be pulled into the treatment operation tube 8b. The root of the lesion 37 is tightly fastened. In this state, when a high-frequency current is supplied to the snare 94, the lesion 37 is resected.

After the treatment is completed, the endoscope 2 is removed from the body cavity. The incision module 6A is then removed. In this case, the second magnet 97 mounted on the distal part 16 of the endoscope 2 is turned. The first magnet 92 of the endoscope module and the second magnet 97 of the endoscope 2 then repel each other due to their respective magnetic forces. This causes the incision module 6A and endoscope 2 to separate from each other.

As mentioned above, since the incision module and endoscope are detachably attached to each other by utilizing magnetic forces, the attachment and detachment of the module to and from the endoscope can be carried out easily.

Moreover, the snare included in the incision module and the incision device operation tube can be handled mutually independently. Thus, the root of the lesion 37 can therefore be fastened reliably.

Referring to FIGS. 12 to 15, a third embodiment of the present invention will be described below.

This embodiment is different from the second embodiment in the structure of the module body and the structure of a coupling member for coupling an endoscope module to an endoscope. The other components are identical to those of the second embodiment. The same reference numerals will be assigned to the same members. The descriptions of those members will be omitted.

Figure 12:
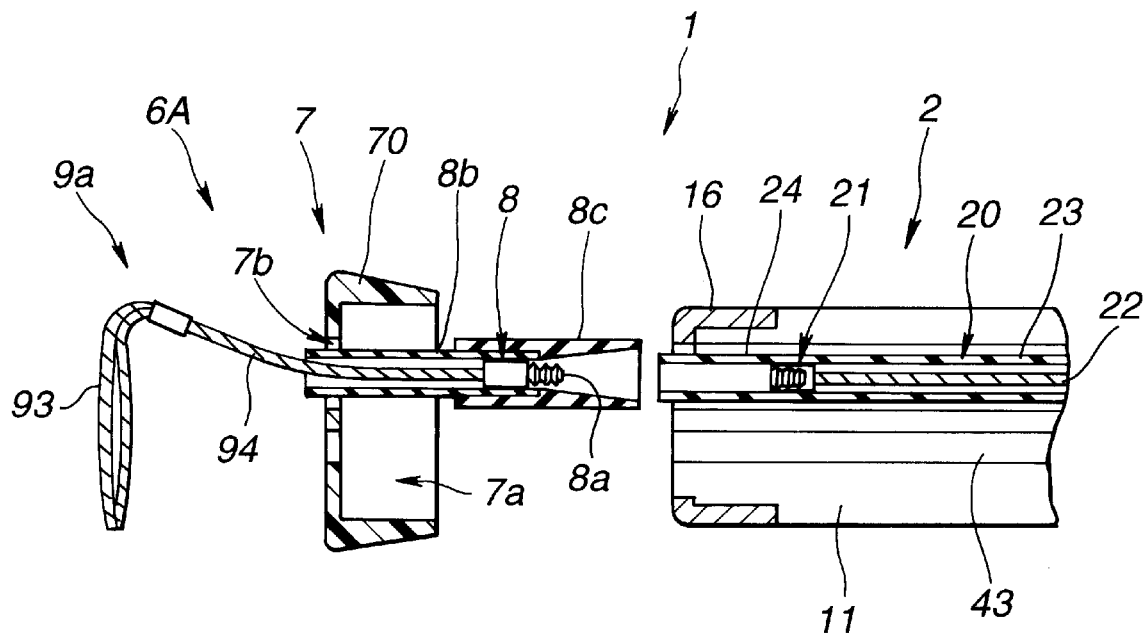
FIGS. 12 to 15 are diagrams for explaining a third embodiment of the present invention.

As shown in FIG. 12, the module body 7 of the incision module 6A that is one of the endoscope modules 6 in accordance with the present invention is formed with a cylindrical body member 70. The body member 70 is made of a resin material or rubber material having elasticity, for example, vinyl chloride resin, silicone, natural rubber, isoprene rubber, or neoprene rubber. The body member 70 is provided with an internal space portion 7a defined by an inner diameter of the body member that is smaller than an outer diameter of the distal part 16, and a treatment instrument passage hole 7b through which a treating means such as the incision device 9a, clamps 9b, or biopsy forceps 9c is passed and which extends in the direction of a longitudinal axis of module body 7. The internal space portion 7a of the body member 70 is fitted on the distal part 16. Due to an elastic force exerted by the body member 70, the inner circumference of the internal space portion 7a is closely fixed to the outer circumference of the distal part 16. With the thickness of the outer circumference of the body member 70, the distal part becomes thicker. Thus, the elastic force is intensified toward this region.

On the other hand, the operation channel 20 is formed separately from a treatment channel 43 which includes an observation window or an illumination window through which illumination light is emitted for illuminating the interior of a body cavity and through which debris is suctioned away or a treatment instrument is passed. The operation tube 23 through which the aforesaid endoscope-side connecting tool 21 and transmission wire 22 extends so as to be able to advance or withdraw freely is inserted into the operation channel 20 so that the operation tube can advance or withdraw freely.

Figure 13:
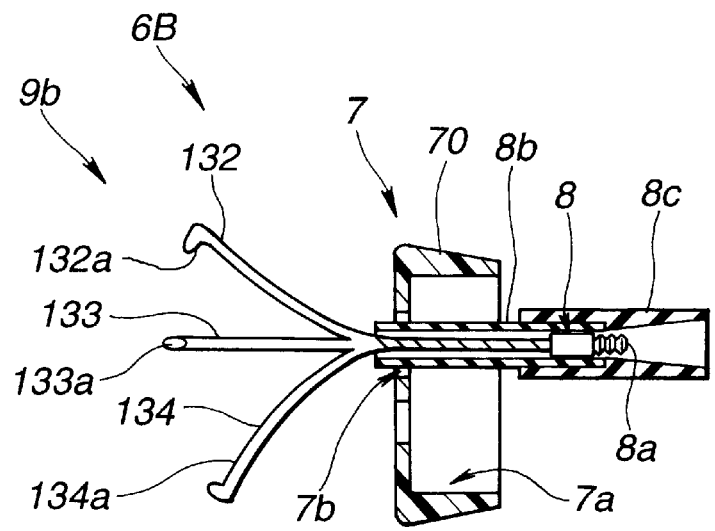
Figure 14:
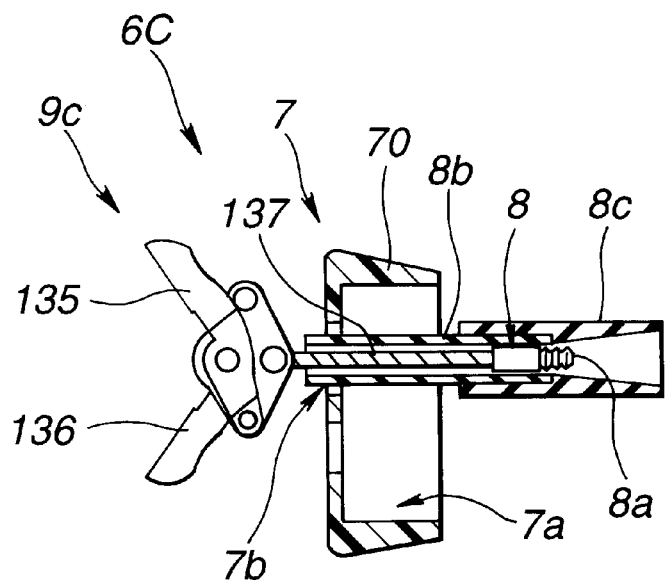

The endoscope modules 6 include, as shown in FIG. 13, a clamping module 6B that realizes clamps 9b. The clamping module 6B has, for example, three elastic members 132, 133, and 134, which are inclined to bend and are provided with clamping portions 132a, 133a, and 134a as the distal parts thereof, instead of the incision device 9a. Also included is a biopsy module 6C (FIG. 14) having a pair of forceps members 135 and 136 pivoted so that the forceps members can pivot freely, having forceps operation wire 137 extended, and thus realizing biopsy forceps 9c.

The number of the elastic members of the clamps 9b is not limited to three but may be a larger value.

Referring to FIG. 12, the procedure of attaching the incision module 6A to the distal part 16 of the endoscope 2 will be described below.

First, the endoscope-side connecting tool 21 fixed to the distal end of the transmission wire 22 is jutted out of the operation tube 23 which extends through the operation channel 20. The module-side connecting tool 8 fixed to the back end of the incision device 9a is then jutted out of the proximal end of the coupling member 8c. The male screw portion 8a of the module-side connecting tool 8 is engaged with the female screw 24 of the endoscope-side connecting tool 21. Thus, the transmission wire 22 and incision device 9a are securely coupled with each other .

Thereafter, the distal part of the operation tube 23 is press-fitted into the tapered portion of the coupling member 8c of the incision module 6A.

The internal space portion 7a of the body member 70 is then fitted on the distal part 16 of the endoscope 2, and thus firmly press-fitted thereon due to the elastic force exerted by the body member 70.

The module body 7 is attached while being turned so that the center axis of the operation channel 20 and the center axis of the treatment instrument passage hole 7b are aligned with each other The procedure for attaching the clamping module 6B or biopsy module 6C to the endoscope 2 is the same as for attaching the incision module 6A thereto.

Figure 15:
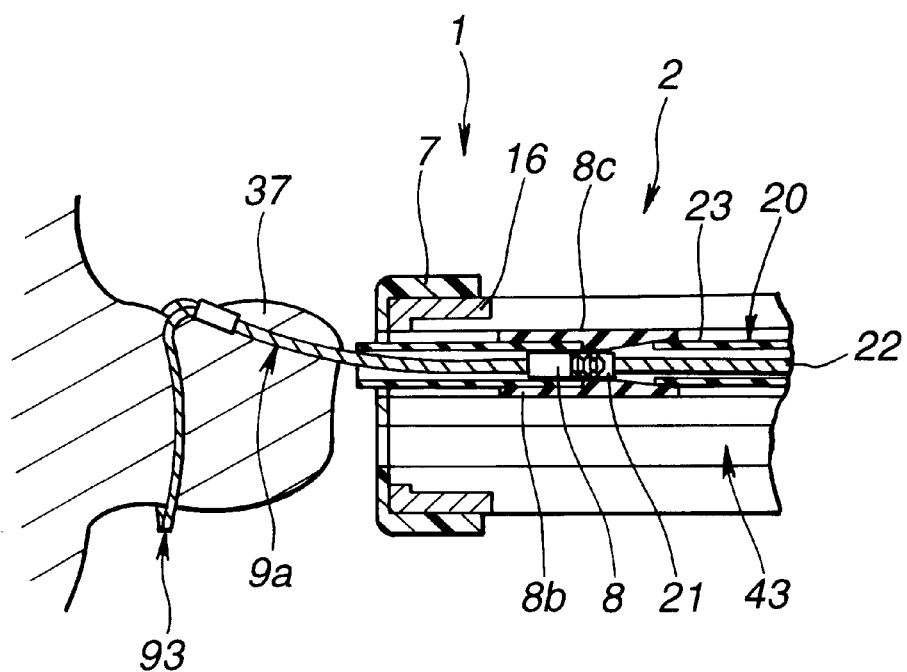

Referring to FIG. 15, the manner of operation of the endoscope 2 having the incision module 6A attached to the distal part 16 thereof as well as the function of the endoscope 2 of this embodiment will be described below.

First, the endoscope 2 having the incision module 6A attached to the distal part 16 is inserted into a body cavity, and the incision module 6A is positioned near a lesion.

Thereafter, the lesion 37 to be incised is placed in the incising member 93 of the incision device 9a. The operation tube 23 is then advanced toward the distal end .

Consequently, the coupling member 8c and the treatment operation tube 8b are pushed out toward the lesion 37, whereupon the lesion 37 is captured in incising member 93. The incising member 93 is pulled into the treatment operation tube 8b to tighten same around lesion 37. Thus, the root of the lesion 37 is fastened.

In this state, the incision device 9a is moved or rotated so that it can be pulled back into the treatment operation tube 8b with optimal smoothness. When the incision device 9a is pulled into the treatment operation tube 8b, the root of the lesion 37 is further fastened by the incising member 93.

In this state, a high-frequency current is supplied to the incision module 6A. This causes the lesion 37 to be cut at the root thereof. The treatment is then completed.

After the treatment is completed, the endoscope 2 is removed from the body cavity, and the incision module 6A is detached from the endoscope 2. The detaching procedure is the reversal of the attaching procedure. First, the module body 7 is dismounted from the distal pat 16. The operation tube 23 and the coupling member 8c are separated from each other. The female screw 24 of the endoscope-side connecting tool 21 and the male screw portion 8a of the module-side connecting tool 8 are disengaged from each other. This causes the endoscope 2 and incision module 6A to separate from each other. In this separated state, the endoscope 2 and incision module 6A can be cleaned or sterilized.

The manner of operating the clamping module 6B (FIG. 13) and the function of the clamping module 6B will be described below. The treatment operation tube 8b is advanced in order to approach the clamps 9b to an object to be clamped such as a cut lesion or foreign matter. The elastic members 132, 133, and 134 are opened. The clamps 9b are pulled into the treatment operation tube 8b, whereby the opened elastic members 132, 133, and 134 are closed. The object to be clamped is fetched and held by the clamping portions 132a, 133a, and 134a.

The manner of operating the biopsy module 6C (FIG. 14) and the function of the biopsy module 6C will be described below. The treatment operation tube 8b is advanced in order to move the biopsy forceps 9c toward a lesion. The transmission wire 22 is pushed and pulled so that the pair of forceps members 135 and 136 is opened and then closed in order to grip the lesion.

Furthermore, in the incision module 6A or clamping module 6B, when the transmission wire 22 is pulled toward the proximal side, the incision device 9a or clamps 9b can be enclosed in the treatment operation tube 8b. The treating means can therefore be evacuated from a field of view being observed. Consequently, impairment of observation efficiency can be prevented. When the incision device 9a or clamps 9b are extended out of the treatment operation tube 8b during observation, the attached state of the endoscope module 6 can be checked easily whenever it is needed.

As mentioned above, the coupling structure for coupling various endoscope modules such as an incision module, clamping module, and biopsy module to an endoscope and the procedure of using the endoscope with any of the endoscope modules attached thereto are the same among all of the endoscope modules. The endoscope modules are thus exchangeable to be attached readily to the endoscope according to a particular treatment or examination procedure. An endoscope module associated with a specific treatment or examination procedure can be selected and attached to the endoscope for the examination or treatment. Furthermore, after use, the endoscope module and endoscope can be separated from each other and then cleaned or sterilized efficiently. Thereafter, the endoscope modules and endoscope can be stored without the necessity of a large space.

Figure 16:
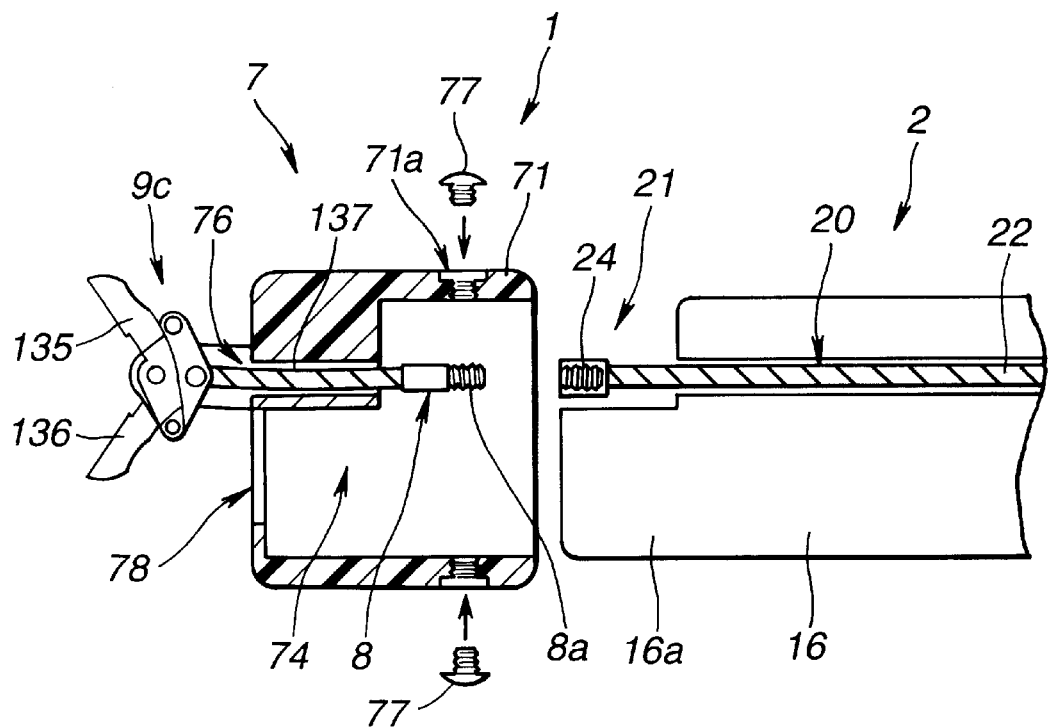
FIGS. 16 to 18 are diagrams for explaining a fourth embodiment of the present invention.
Figure 17:
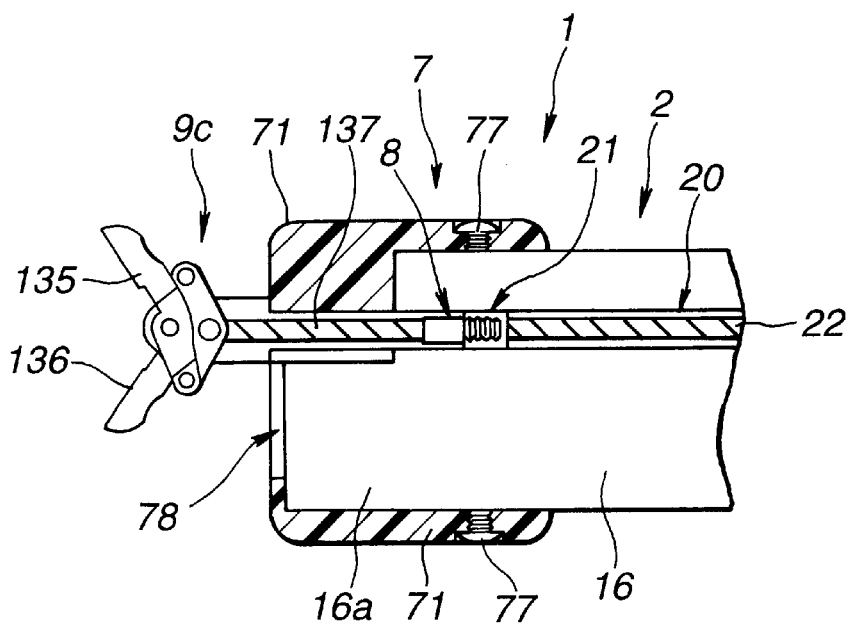
Figure 18:
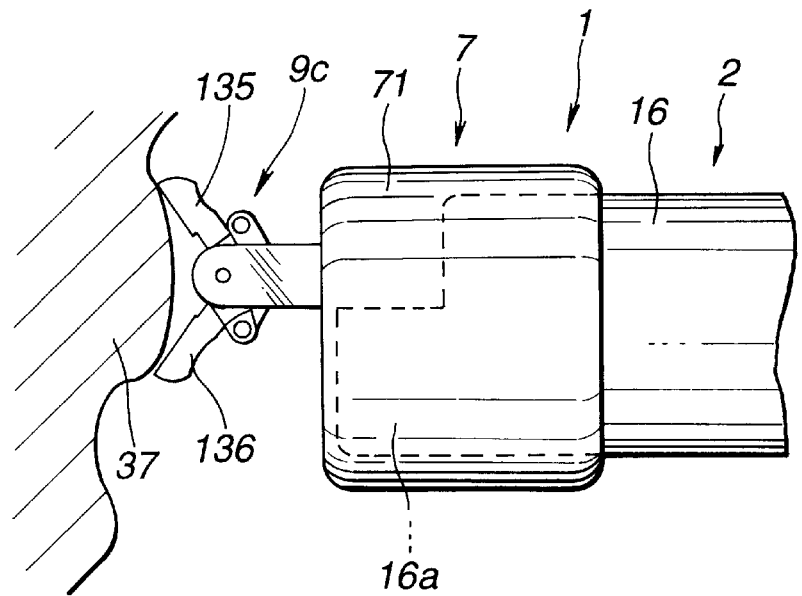

Referring to FIGS. 16 to 18, a fourth embodiment of the present invention will be described below.

In this embodiment, a module body is screwed firmly to an endoscope in an effort to prevent an endoscope module from coming off from the distal part of the endoscope. The other components are identical to those of the first embodiment. The same reference numerals will be assigned to the same members. The description of those members will therefore be omitted.

As shown in FIG. 16, a main unit 71 of a biopsy module 6C that is one of the endoscope modules 6 is made of a hard resin material, for example, polyolefine, polycarbonate, acrylonitrile butadiene styrene resin (ABS), polyamide, vinyl chloride, latex, or-natural rubber, and shaped substantially like a pipe. A pair of forceps members 135 and 136 is attached to the main unit 71 so that they can pivot freely. Thus, the biopsy forceps 9c from which a forceps operation wire 137 extends is realized.

Main unit 71 includes a distal part placement socket 74 into which the distal projection 16a of the distal part 16 serving as an attachment portion of the endoscope 2 is fitted, and a wire passage hole 76 through which the forceps operation wire 137 is provided to open or close the forceps members 135 and 136 by advancing or withdrawing the operation wire 137. The module-side connecting tool 8 is fixed to the proximal end of the forceps operation wire 137.

A threaded bore 71a communicating with the distal part placement socket 74 and having a screw seat formed thereon is formed in the outer circumference of the main unit 71. A locking screw 77 serving as a coupling and locking means is fitted into the threaded bore 71a.

The wire passage hole 76 communicates with the distal part placement socket 74. The distal part placement socket 74 communicates with the exterior of main unit 71 via a communication aperture 78.

The endoscope 2 of this embodiment does not require a locking attachment bore as in the second third embodiments discussed above.

As shown in FIG. 17, the female screw 24 of the endoscope-side connecting tool 21 fixed to the distal end of the transmission wire 22 in the endoscope 2 is engaged firmly with the male screw portion 8a of the module-side connecting tool 8 fixed to the proximal end of the forceps operation wire 137 in the biopsy module 6C. The distal part 16 of the endoscope 2 is then inserted into the distal part placement socket 74 in the main unit 71. Thereafter, the biopsy module 6C is securely fixed to the distal part 16 of the endoscope 2 by tightening the locking screw 77. Like the first embodiment, the endoscope 2 is introduced into a body cavity with the biopsy forceps 9C of the biopsy module 6C closed.

The transmission wire 22 is advanced or withdrawn by handling the operation knob 17 mounted on the operation unit 12 of the endoscope 2. The forceps operation wire 137 coupled to the transmission wire 22 is then, as shown in FIG. 18, correspondingly advanced or withdrawn. This causes the biopsy forceps 9c to open or close, whereupon biopsy is then performed on the lesion 37.

In this embodiment, the endoscope module and endoscope are secured using the screw. Attachment or detachment can be achieved easily. The endoscope module can be firmly fixed to the endoscope.

Figure 19:
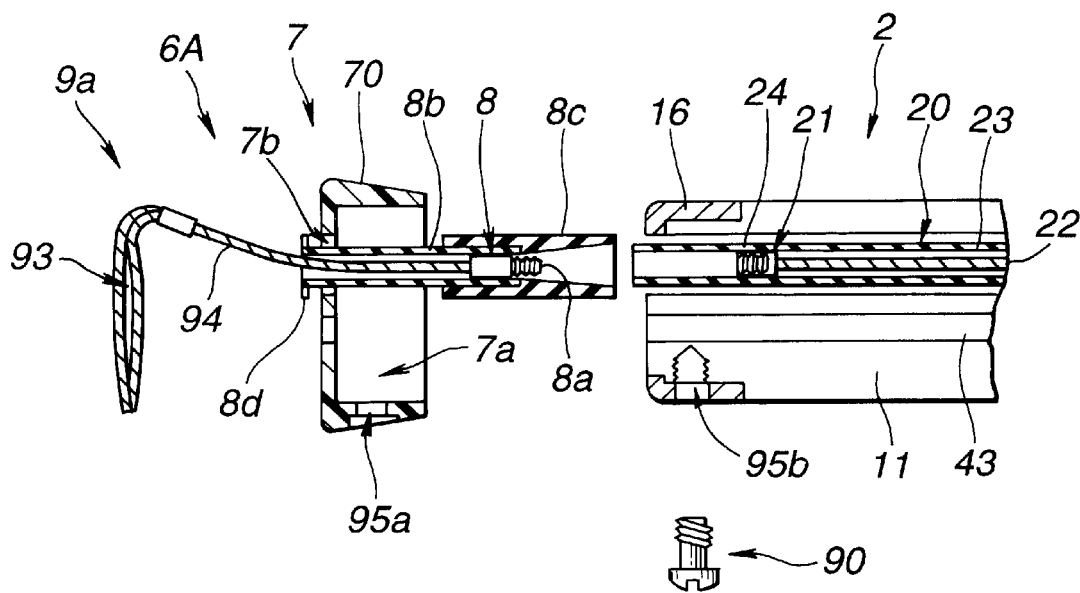
FIG. 19 is a diagram showing a structure of the distal part of the endoscope and of a module body for preventing the endoscope module from inadvertently becoming detached from the distal part of the endoscope.

FIG. 19 shows another embodiment in which an endoscope module is prevented from being inadvertently removed from the distal part of an endoscope.

As shown in FIG. 19 in this embodiment, like the third embodiment, when a treatment is conducted with the incision module 6A attached to the distal part 16, a load (external force) may be imposed on the cylindrical body member 70 in the direction of the longitudinal axis thereof. For this reason, merely press-fitting the body member 70 onto the distal part 16 does not impart sufficient locking strength . For providing an endoscope system 1 in which the endoscope module 6 is prevented from inadvertently separating from the endoscope 2 during use, the body member 70 is first press-fitted on the distal part 16, and then the body member 70 and distal part 16 are further secured using a screw 90.

To be more specific, a through-hole 95a through which the screw 90 is inserted is bored in the lateral circumference of the body member 70, so that the through-hole 95a will extend in a direction orthogonal to the longitudinal axis of the body member 70. A female screw 95b with which the screw 90 is engaged is threaded into the distal part 16 of the endoscope 2 so that it will coincide with the through-hole 95a of the body member 70.

The through-hole 95a and female screw 95b are aligned with each other when the body member 70 is perfectly press-fitted onto the distal part 16. The screw 90 is then engaged with the female screw 95b via the through-hole 95a. Consequently, the body member 70 is securely fixed on the distal part 16 of the endoscope 2 without risk of any relative movement therebetween in the direction of the longitudinal axis along which the endoscope is inserted. Reference numeral 8d denotes a stopper for preventing the treatment operation tube 8b from being removed through the proximal side of the endoscope.

As mentioned above, after the module body is press-fitted onto the distal part of an endoscope, the module body is firmly engaged with the distal part of the endoscope using a screw. Thus, the module body and the distal part of the endoscope can be firmly and securely attached. Consequently, the endoscope module can be prevented from being inadvertently separated from the distal part of an endoscope or displaced during an examination or treatment procedure and thereby impairing the performance of the endoscope.

In the third embodiment, even if the body member 70 were to become separated from the distal part 16, since the male screw portion 8a and female screw 24 are engaged with each other, the module will not fully detach from the endoscope . However, in this case, the performance efficiency of the treatment may be hindered. For example, a load concentrated on the interface between the mutually engaged male screw portion 8a and female screw 24 may lead to a breakage thereof.

Figure 20:
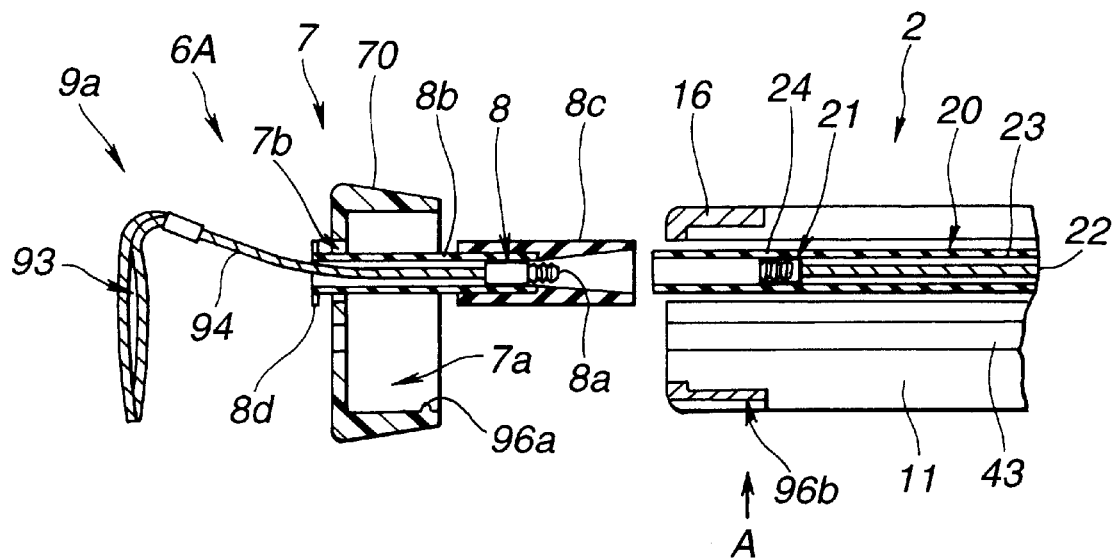
FIGS. 20 and 21 are diagrams for explaining another embodiment intended to prevent an endoscope module from inadvertently becoming detached from the distal part of the endoscope.
Figure 21:
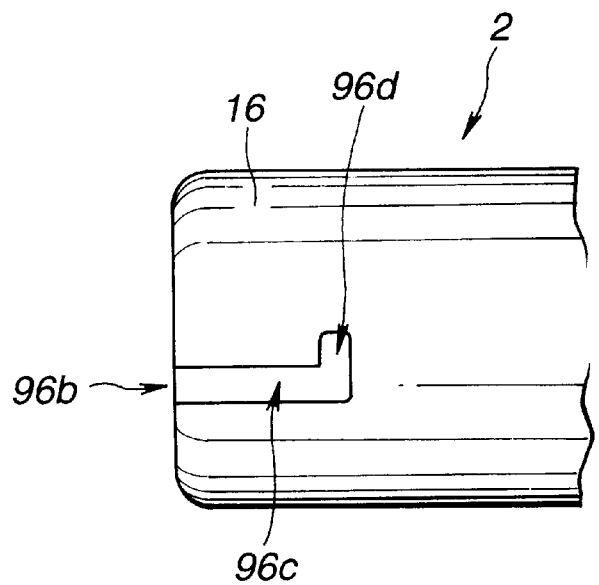

FIGS. 20 and 21 show another embodiment for preventing inadvertent detachment of an endoscope module from the distal part of the endoscope.

As shown in FIGS. 20 and 21, in this embodiment, a jut 96a serving as a locking means is formed as part of the inner circumference of the body member 70. Jut 96a is designed to prevent the endoscope module 6 from inadvertently detaching from the distal part 16 or from being displaced once attached thereto. Moreover, a groove 96b into which the jut 96a is fitted is formed as part of the outer circumference of the distal part 16. The groove 96b consists of a linear groove 96c extending from the distal end of the endoscope in the direction of the longitudinal axis of the endoscope, and a positioning groove 96d substantially orthogonal to the linear groove 96c.

When the body member 70 is attached to the distal part 16, the jut 96a of the body member 70 is aligned with the linear groove 96c in the distal part 16. In this state, the body member 70 is attached to the distal part 16. The body member 70 is then turned so that the jut 96a will be fitted in the positioning groove 96d. Thus, attachment of the module body 7 to the distal part 16 is completed.

With the simple task of turning the body member slightly relative to the distal part, inadvertent detachment or displacement can be prevented and the module body can be securely attached to the distal part.

The module body and the distal part may be structured so that when the jut 96a is moved from the linear grove 96c to the positioning groove 96d, a sense of resistance will be felt or a click will sound. This will help a user recognize the locked state.

Figure 22:
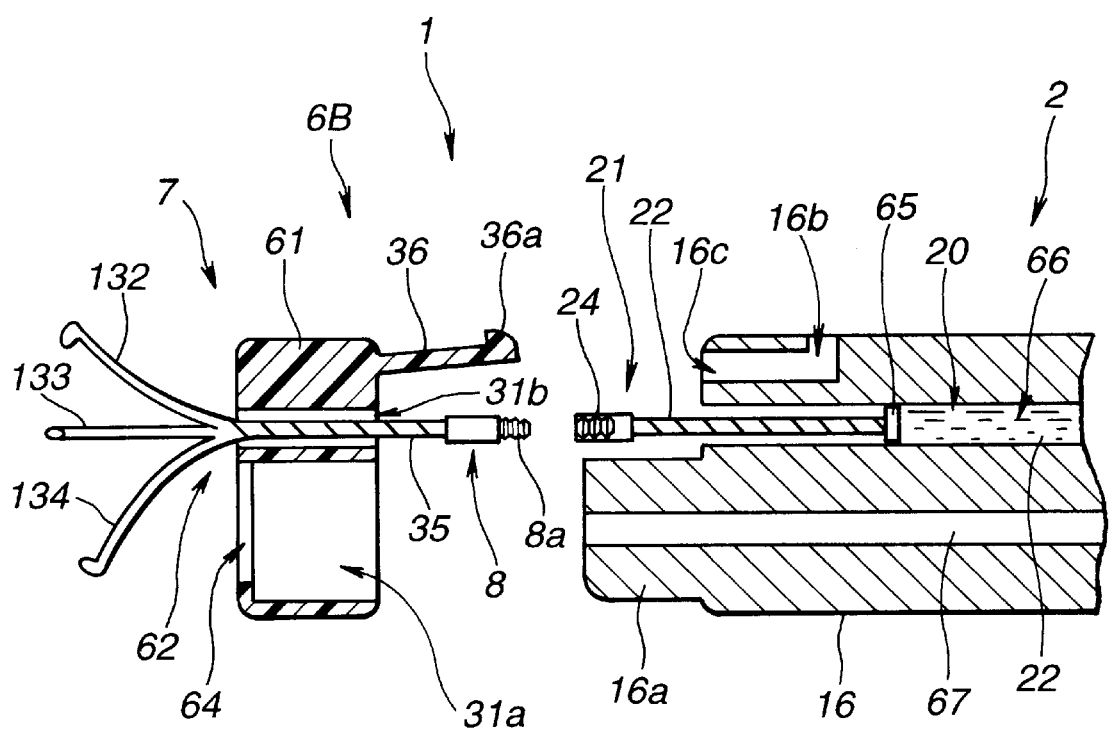
FIG. 22 is a diagram for explaining a fifth embodiment of the present invention, and for explaining the structure of an operation force transmitting means for opening or closing a clamping module that is one of the endoscope modules.

Referring to FIG. 22, a fifth embodiment of the present invention will be described below.

In this embodiment, an operation force transmitting means for transmitting an operation force to a treating means in an endoscope module is actuated with a fluid. The other components are identical to those of the first embodiment. The same reference numerals will be assigned to the same members. The description of those members will thus be omitted.

As shown in FIG. 22, the endoscope module 6 of this embodiment is the clamping module 6B. The clamping module 6B has a structure similar to that of the ligation module 6E made of a hard resin material, for example, polyolefine, polycarbonate, ABS, polyamide, vinyl chloride, latex, or natural rubber, and shaped substantially like a pipe. Specifically, the clamping module 6B comprises a body member 61 forming the module body 7 and including the projection placement socket 31a and attachment jut 36, and clamps 9b composed of, for example, three clamping members 132, 133, and 134.

Formed in the body member 61 are the projection placement socket 31a in which the distal projection 16a of the distal part 16 of the endoscope 2 is fitted, the attachment jut 36 having the locking claw 36a formed at the distal end thereof so as to be fitted into the coupling hole 16c, and the wire passage hole 31b through which the operation wire 35 extends to be able to advance or withdraw freely.

The wire passage hole 31b is a through-hole, and the projection placement socket 31a communicates with the exterior of the module body 7 via a communication aperture 64. The module-side connecting tool 8 that serves as a coupling means and has a substantially column-like shape is fixed to the proximal end of the operation wire 35.

A piston 65 having a dimension permitting substantially close contact with the inner circumference of the operating channel 20 is fixed at a point along the length of the transmission wire 22 extending from the endoscope-side connecting tool 21. Herein, the endoscope-side connecting tool 21 has the female screw 24 formed thereon, which is engaged with the male screw portion 8a of the module-side connecting tool 8. To advance the transmission wire 22, the operation channel 20 is filled with a liquid 66 such as physiological saline.

A liquid compressing means, for example, a cylinder, not shown, is mounted on the operation unit 12 of the endoscope 2 . The liquid compressing means communicates with the operation channel 20 to supply or suction a liquid to or from the operation channel 20.

Reference numeral 67 denotes a suction channel provided in the endoscope 2 for the purpose of suction removal of tissue or debris.

The operations of the endoscope system 1 of this embodiment having the foregoing components will be described below.

First, the female screw 24 in the distal part of the transmission wire 22 is engaged firmly with the male screw portion 8a of the module-side connecting tool 8 fixed to the proximal end of the operation tool 8 fixed to the proximal end of the operation wire 35 of the clamping module 6B. The attachment jut 36 of the body member 61 is fitted into the coupling hole 16c. The distal projection 16a and projection placement socket 31a are aligned with each other. The clamping module 6B is then moved to the distal part 16. The distal projection 16a is then fitted into the projection placement socket 31a. The body member 61 is thus located at a proper position. The locking claw 36a is fitted in the locking recess 16b. Consequently, the clamping module 6B is securely fixed to the distal part 16 of the endoscope 2.

Thereafter, the operation knob 17 on the operation unit 12 of the endoscope 2 is handled in order to stow the clamping members 132, 133, and 134 of the clamping module 6B in the wire passage hole 31b and operation channel 20. In this state, the endoscope 2 is inserted into a body cavity.

Thereafter, the liquid compressing means, not shown, is used to compress a liquid, whereby the piston 65 is moved toward the distal side of the endoscope. An operation force is thus transmitted to the transmission wire 22 and operation wire 35 in order to advance the clamping members 132, 133, and 134. By advancing and slightly retracting the clamping members 132, 133 and 134, an object is clamped. If necessary, fluids or other debris is removed from the treatment site through the suction channel 67.

As mentioned above, a liquid is utilized to exert an operation force required for handling a treating means in an endoscope module. The operation force can be transmitted reliably to the treating means irrespective of the angle of insertion of the endoscope. The treating means can therefore be moved reliably.

Moreover, since an independent suction channel is included in the endoscope, suction can be achieved reliably.

Figure 23:
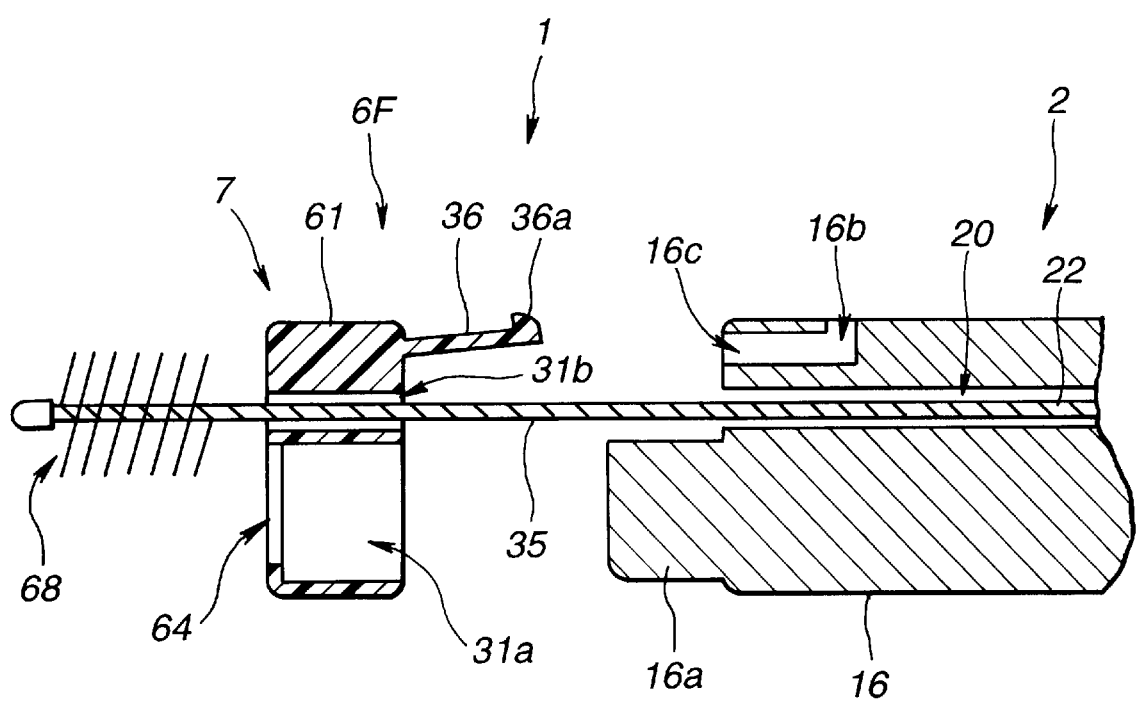
FIGS. 23 and 24 are diagrams for explaining a sixth embodiment of the present invention.
Figure 24:
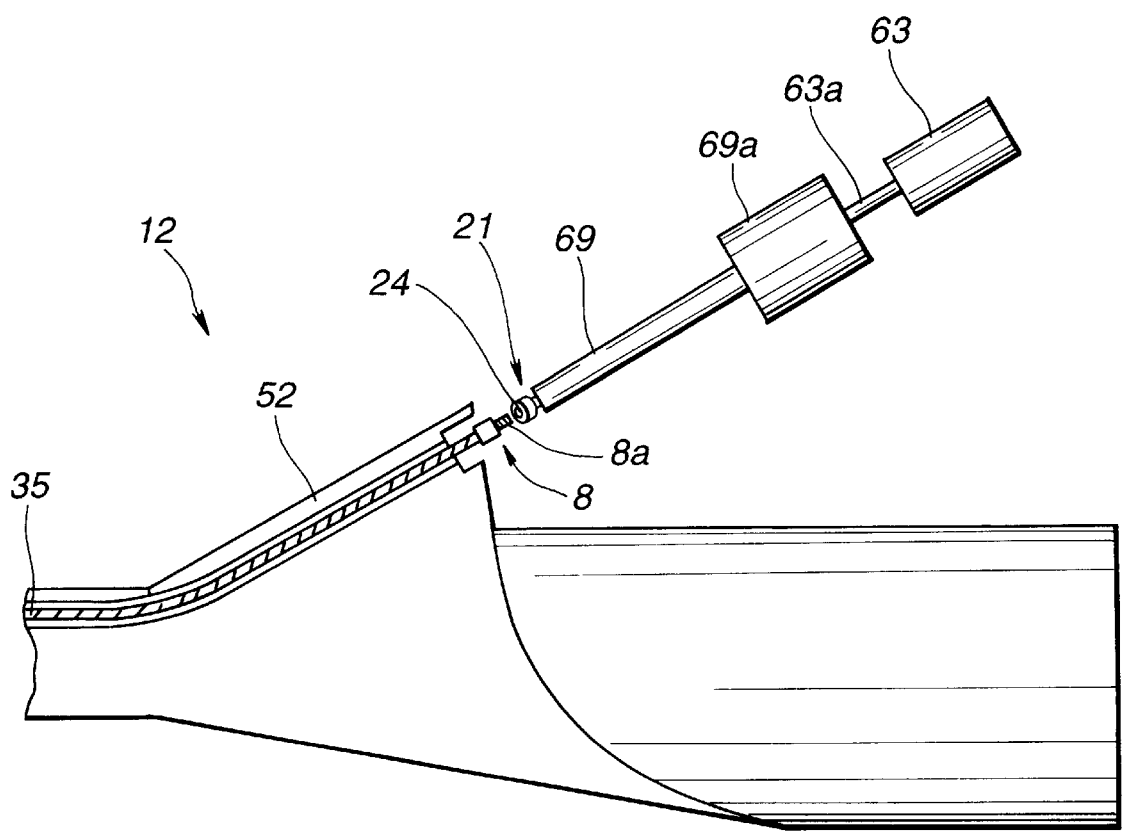

Referring to FIGS. 23 and 24, a sixth embodiment of the present invention will be described below.

This embodiment is different from the first embodiment in the position at which the module-side connecting tool 8 and endoscope-side connecting tool 21 are coupled with each other. The other components are identical to those of the first embodiments. The same reference numerals are assigned to the same members. The description of those members will therefore be omitted.

As shown in FIG. 23, the endoscope module 6 of this embodiment is a cytodiagnosis module 6F that has a brush 68 fixed to the distal part of the operation wire 35. The operation wire 35 disposed in the operation channel 20 extends from the distal end of the endoscope and, as shown in FIG. 24, out through the operation unit 12. The module-side connecting tool 8 having the male screw portion 8a as the proximal part thereof is fixed to the proximal end of the operation wire 35. The endoscope-side connecting tool 21, which is engaged with the male screw portion 8a of the module-side connecting tool 8, has the female screw 24 threaded therein and is fixed to the distal end of a small-diameter portion 63a of a knob 63. The knob 63 is loosely engaged with an operation body 69. When the knob 63 is turned relative to the operation body 69, the brush 68 is turned, causing cells at the treatment site to adhere to the brush 68. Reference numeral 69a denotes a support located proximally to the operation body 69 and designed to be grabbed with the user's fingers. Moreover, the cytodiagnosis module 6F, operation body 69, and knob 63 are made of a heat resistant material and can therefore be autoclaved or thermally sterilized.

In this embodiment, the operation wire 35 extends out of the operation unit 12. In this state, the module-side connecting tool 8 and endoscope-side connecting tool 21 are screwed firmly to each other. The operation wire 35 is thus coupled to the operation body 69.

As mentioned above, the operation wire is extended through the operation unit. A module-side connecting tool of the operation wire and an endoscope-side connecting tool of the operation body are coupled with each other on the side of the operation unit. Consequently, this embodiment can operate in a similar manner and provide the same advantages as the afore-described embodiments.

Figure 25:
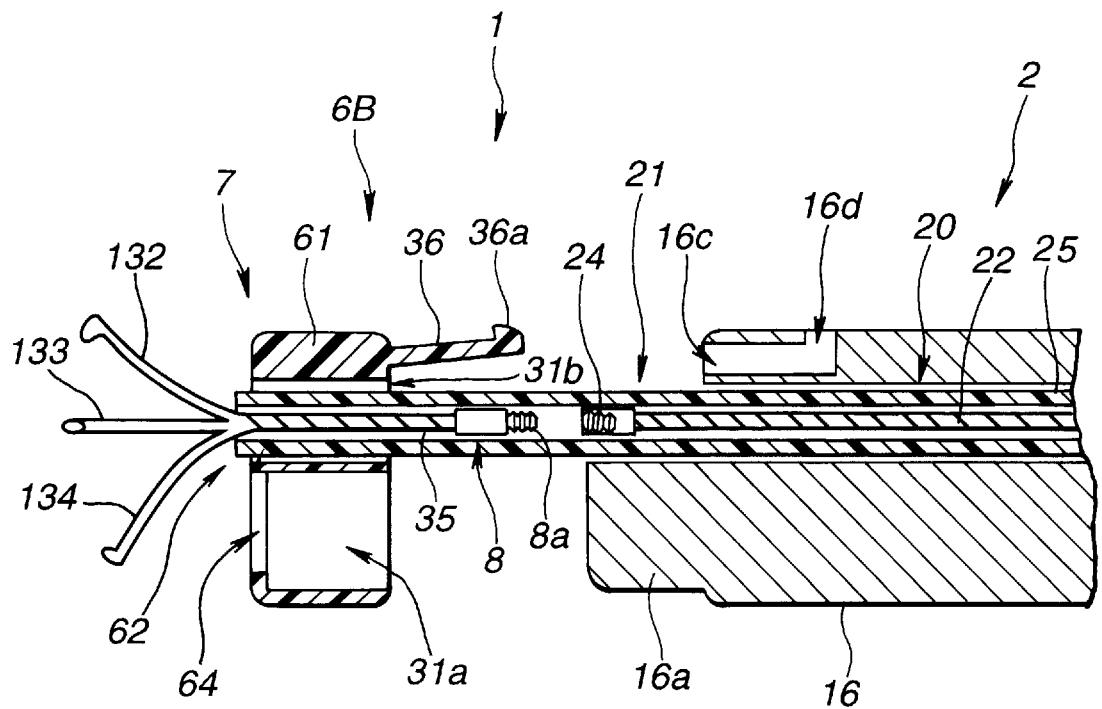
FIGS. 25 and 26 are diagrams for explaining a seventh embodiment of the present invention.
Figure 26:
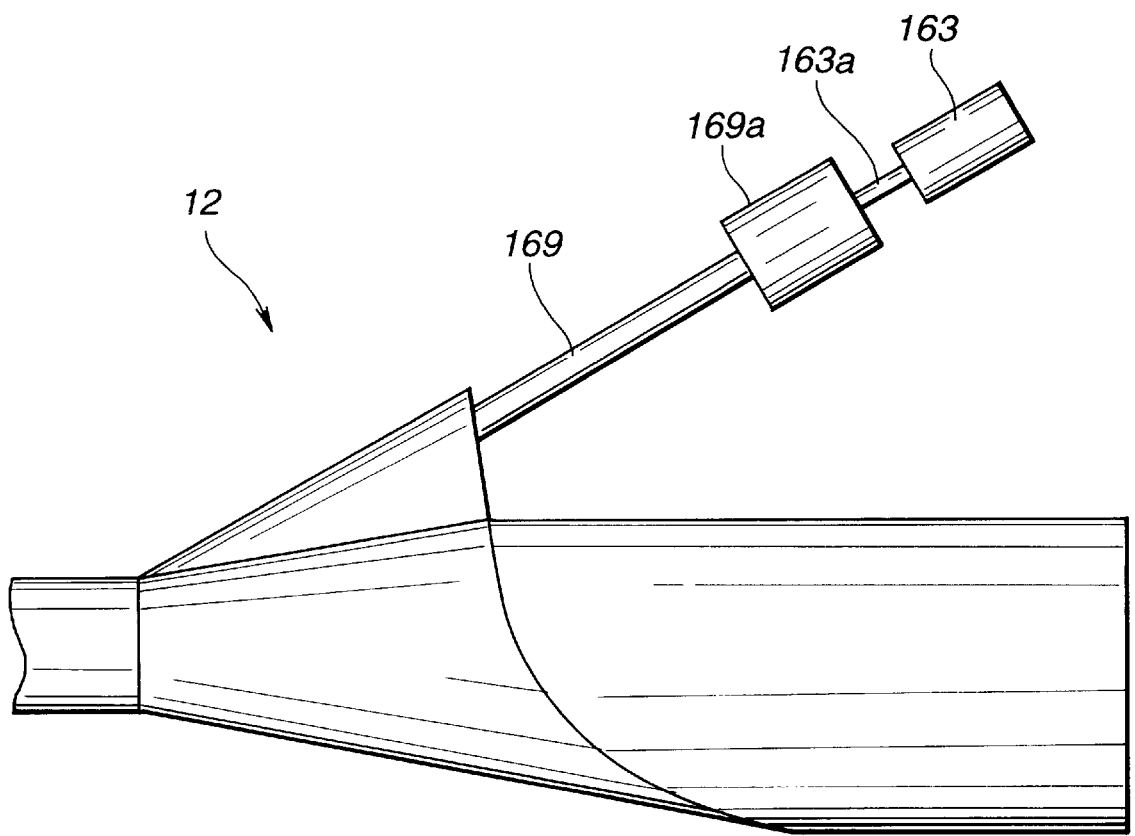

Referring to FIGS. 25 and 26, a seventh embodiment of the present invention will be described below.

As shown in FIG. 25, in this embodiment, the module-side connecting tool 8 and endoscope-side connecting tool 21 are designed to be joined to each other as discussed with previous embodiments. Thus, the clamping members 132, 133, and 134, operation wire 35, and transmission wire 22, once united with one another, are passed through a wire passage tube 25 so that they can be advanced or withdrawn freely. The wire passage tube 25 is enclosed in the operation channel 20 so that it can also be advanced or withdrawn freely.

As shown in FIG. 26, an operation body 169 designed to be able to be advanced or withdrawn freely and shaped like a pipe extends out from the operation unit 12. A small diameter portion 163a of a knob 163 is loosely engaged with the through-hole in the operation body 169 through a large-diameter support 169a that is fixed to the proximal end of the operation body 169.

The proximal end of the wire passage tube 25 is fixed to the distal end of the operation body 169. The proximal end, not shown, of the transmission wire 2 is fixed to the distal end of the knob 163.

When the operation body 169 is moved in a direction in which the endoscope is inserted, the distal end of the wire passage tube 25 is advanced out of the distal end of the body member 61 attached to the distal part 16 of the endoscope 2. By moving the knob 163 in the direction of insertion, the transmission wire 22 is moved to cause the clamping members 132, 133, and 134 located at the distal end of the operation wire 35 to open.

As mentioned above, an operation wire extending from a treating means and a transmission wire coupled to the operation wire are passed through a wire passage tube that can be advanced or withdrawn freely relative to an operation channel. When the operation wire is handled with the wire passage tube extending out of the distal end of the module body, a lesion located at the distal end thereof can be treated or examined.

Figure 27:
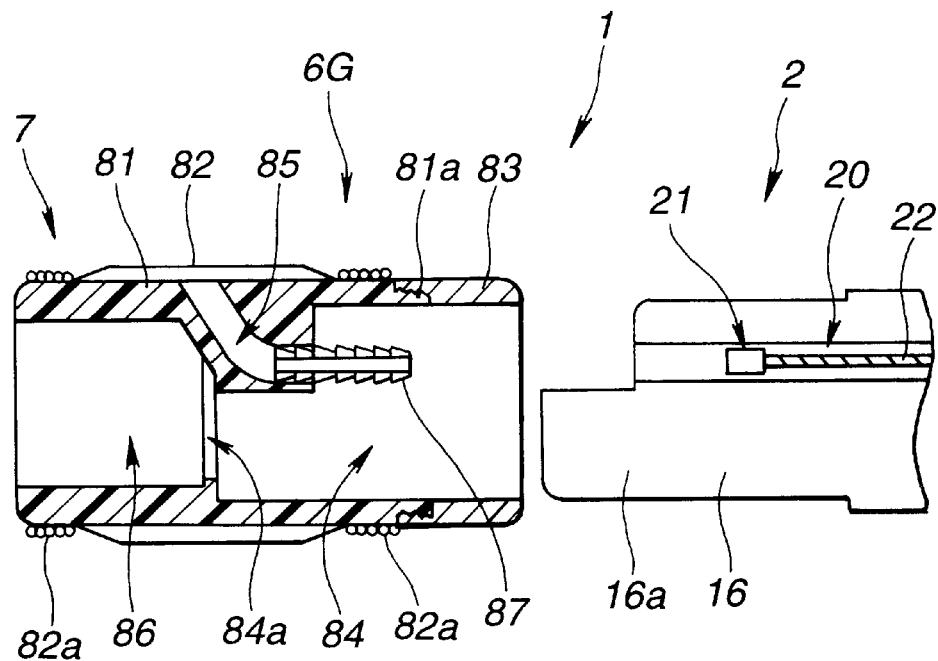
FIGS. 27 to 29 are diagrams for explaining an eighth embodiment of the present invention.
Figure 28:
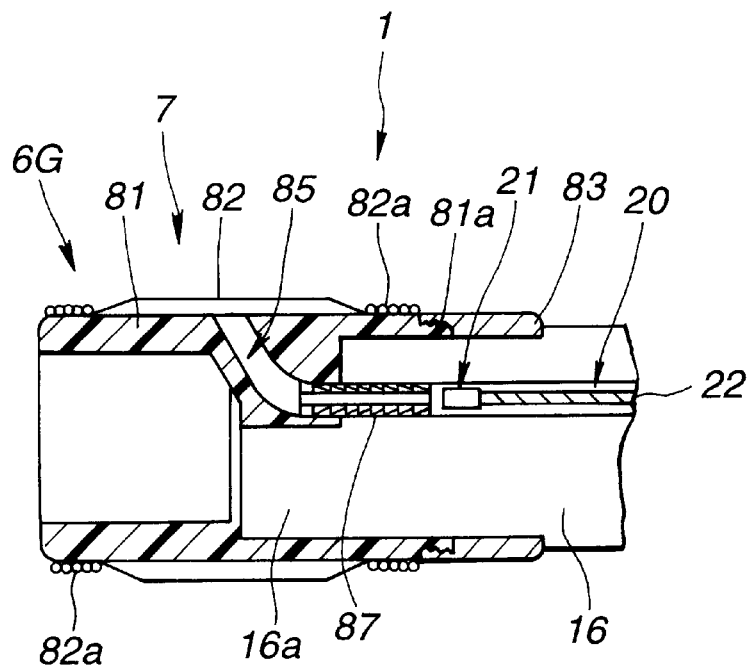
Figure 29:
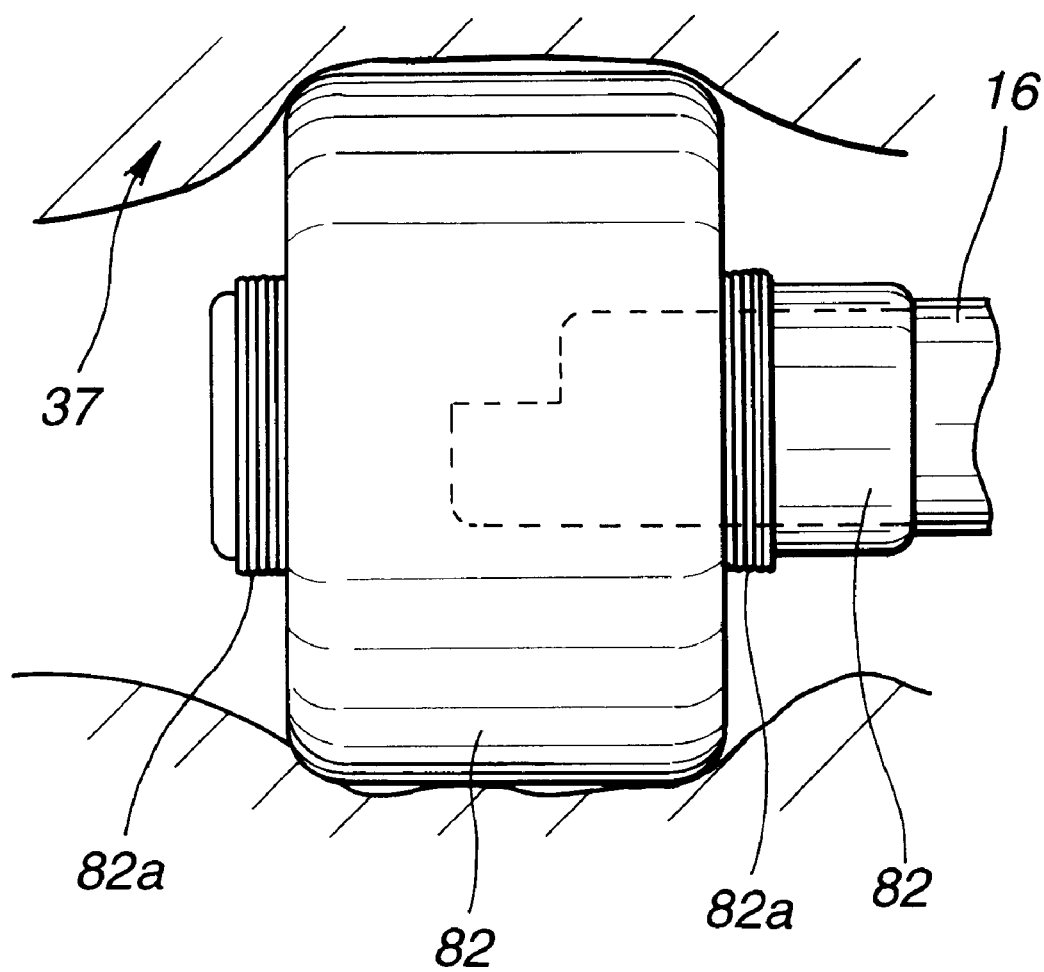

Referring to FIGS. 27 to 29, an eighth embodiment of the present invention will be described below.

As shown in FIG. 27, the endoscope module 6 of this embodiment is a dilation module 6G. In the dilation module 6G, a balloon 82 made of an elastomer having elasticity and a small thickness, for example, vinyl chloride resin, silicone, natural rubber, isoprene rubber, or neoprene rubber, and shaped substantially like a cylinder is placed on the outer circumference of a body member 81 made of a hard resin, for example, polyolefin, polycarbonate, ABS, polyamide, vinyl chloride, latex, or natural rubber, and shaped substantially like a pipe.

A convex portion 81a having a male screw threaded thereon is formed as the proximal portion of the body member 81. A female screw threaded on the distal part of a joint member 83 shaped substantially like a pipe is engaged with the male screw. The joint member 83 is thus engaged with a convex portion 81a of the body member 81. When the joint member 83 is turned in a direction in which the connection between convex portion 81a and joint member 83 is tightened, the inner diameter of the convex portion 81a is reduced gradually.

Both ends of the balloon 82 are fixed to the body member 81 with bobbin attachments 82a.

The body member 81 also has formed therein a distal placement socket 84 into which the distal part 16 having a distal projection 16a that serves as an attachment portion of the endoscope 2 is fitted, an aeration/perfusion passageway 85 through which air or liquid used to dilate the balloon 82 is supplied, and a distal hollow 86 having an opening at the distal end thereof.

One end of the aeration/perfusion passageway 85 opens on the outer circumference of the body member 81 on which the balloon 82 is placed, and the other end thereof communicates with the distal part placement socket 84. The distal part placement socket 84 communicates with the distal hollow 86 via a communication aperture 84a. A connection member 87, which is designed to serve as coupling means and aeration/perfusion passageway defining means, is hollow and made of a material having elasticity. Additionally connection member 87 is shaped like a nipple and is fixed to the proximal end of the aeration/perfusion passageway 85. The connection member 87 can be inserted into the operation channel 20 provided in the endoscope 2 so that it can be readily removed.

The connection member 87 is made of a material exhibiting good adhesiveness and causing neither liquid leakage nor air leakage, such as, silicone, natural rubber, isoprene rubber, or neoprene rubber.

The operations of the endoscope system 1 of this embodiment having the foregoing components will be described below.

First, the operation knob 17 mounted on the operation unit 12 of the endoscope 2 is turned. The endoscope-side connecting tool 21 fixed to the distal end of the transmission wire 22 is, as shown in FIG. 27, placed in the operation channel 20. In this state, the distal part 16 of the endoscope 2 is inserted into the distal part placement socket 84 in the body member 81 through the through-hole of the joint member 83. The connection member 87 is pushed into the operation channel 20. This causes the dilation module 6G to be temporarily fixed to the distal part 16 of the endoscope 2.

Thereafter, the joint member 83 is turned in a direction to tighten the connection between body member 81 and joint member 83. Accordingly, the inner diameter of the convex portion 81a is decreased gradually. The inner circumference of the convex portion 81a presses against the outer circumference of the distal part 16 of the endoscope 2. Consequently, the dilation module 6G and endoscope 2 are, as shown in FIG. 28, securely connected.

Thereafter the endoscope 2 having the dilation module 6G attached to the distal part 16 thereof is inserted into a body cavity. A syringe that is not shown is coupled to the base on the operation unit and a liquid contained in the syringe is injected into the operation channel 20. The liquid injected from the syringe then flows into the balloon 82 through the operation channel 20 in the endoscope 2, the connection member 87, and the aeration/perfusion passageway 85. The balloon 82 is then dilated as shown in FIG. 29. Using the dilated balloon 82, the lesion 37 is dilated and pressurized. Thus, a stenotic lesion in a body cavity can be treated or a lesion can be pressurized for hemostasis.

As mentioned above, when the dilation module and endoscope are attached to each other, the connection member having elasticity is press-fitted into the operation channel. The joint member is tightened, whereby the inner diameter of the dilation module is partly decreased. The outer circumference of the distal part of the endoscope is pressed and fastened with the inner circumference of the region of the dilation module in which the inner diameter has been decreased. Thus, the module body and endoscope can be securely fixed to each other easily and firmly.

Figure 30:
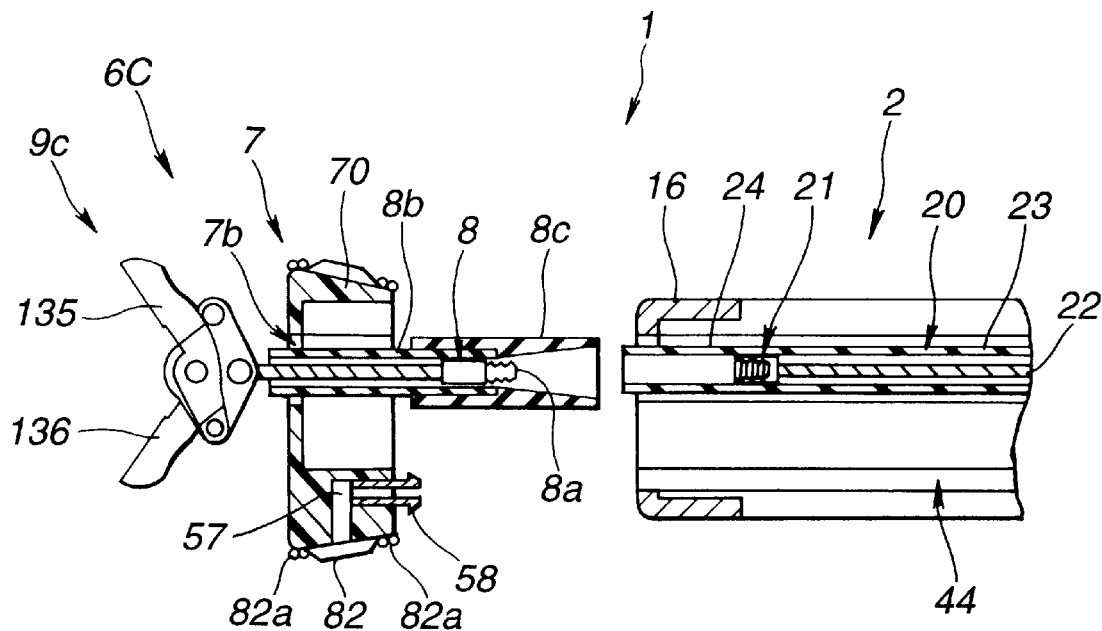
FIGS. 30 and 31 are diagrams for explaining a ninth embodiment of the present invention.
Figure 31:
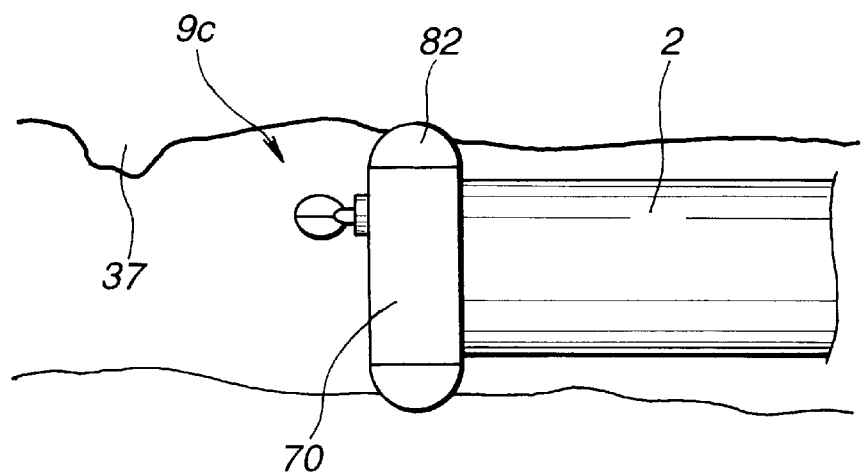

Referring to FIGS. 30 and 31, a ninth embodiment of the present invention will be described below.

As shown in FIG. 30, in this embodiment, the balloon 82 is placed on the lateral circumference of the body member 70 of, for example, the biopsy module 6C that is one of the endoscope module 6. The balloon 82 is secured on the outer circumference of the body member 70 using the bobbin attachments 82a.

The body member 70 has an aeration hole 57 reaching the inner surface of the balloon 82. An aeration base 58 that can be engaged with an aeration/perfusion channel 44 provided in the endoscope 2 so that it can be disengaged freely therefrom is formed at the back end of the aeration hole 57.

With the body member 70 attached to the distal part 16, the balloon 82 is, say, aerated through the aeration/perfusion channel 44 in the endoscope 2. The balloon 82 then dilates as shown in FIG. 31. The endoscope 2 is held and immobilized in the body cavity. Consequently, biopsy can be performed on the lesion 37 on a stable basis.

As mentioned above, when an endoscope module is formed with a balloon placed on the outer circumference thereof, the balloon can be dilated at a desired position in a lumen in order to hold and immobilize the endoscope. Consequently, an examination or treatment can be carried out with the endoscope immobilized. The reliability and workability of the treatment or examination will improve greatly.

Figures 32A, 32B:
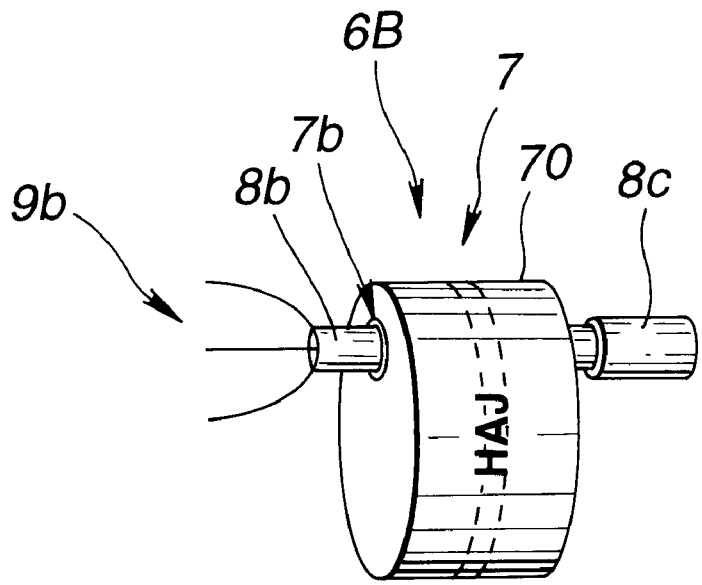
FIGS. 32A and 32B are diagrams for explaining a tenth embodiment of the present invention.

Referring to FIGS. 32a and 32b, a tenth embodiment of the present invention will be described below.

As mentioned above, the endoscope modules included in the endoscope system 1 have mutually different treating means associated with different purposes or treatments or examinations. In this embodiment, as shown in FIG. 32A, an endoscope module such as the clamping module 6B having clamps 9b is the treating means. Characters describing the type of treating means or a color indicator indicating the type of treating means is inscribed or painted on the outer surface of the body member 70, for example, the lateral circumference thereof.

Characters or a color used to identify a type of module is determined, for example, as shown in FIG. 32B, according to the treating means included in a module. Specifically, characters "HAJ" may be inscribed on the lateral circumference of the clamping module 6B, as shown in FIG. 32A.

Otherwise, an annular belt-like zone on the lateral circumference of the body member 70, which is indicated with dashed lines, may be painted white or other distinguishing solid color.

Thus, colors on the outer surfaces of modules which are mutually differentiated, distinguishing characters, or a symbol which indicates the type of module is provided on the outer surface of each module. Various types of endoscope modules can therefore be distinguished based on the treating means included in the modules. Consequently, the treating means included in the module can be easily identified. This feature is helpful in preventing incorrect use of a module.

Moreover, the type of endoscope module can be quickly identified before and after the endoscope module is attached to the endoscope.

Alternatively, the different types of modules may be distinguished by varying the width of the belt-like zone or the number of belt-like zones. The lateral circumference, distal surface, whole surface of the body member 70, or the coupling member 8c may be colored so as to correspond with the colors of the different types of modules listed in FIG. 32b. As further alternatives, a model name, graphical characters, a symbol, or the like indicating the treating means may be substituted for characters. As long as the model name, graphical characters, symbols, or the like are discernable, their shapes or orientation are a matter of design choice.

Figure 33:
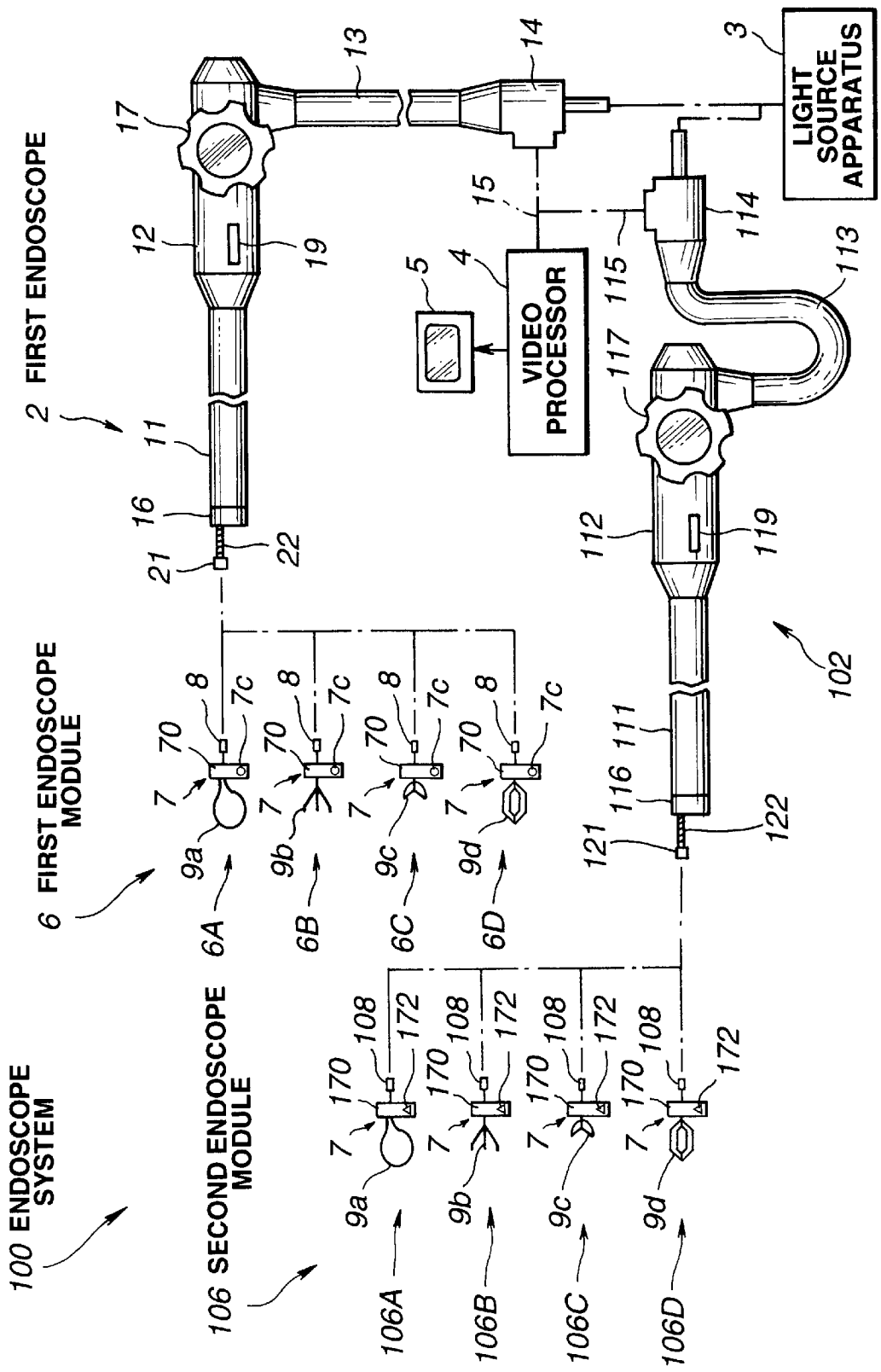
FIGS. 33 to 35 are diagrams for explaining an eleventh embodiment of the present invention.
Figure 34:
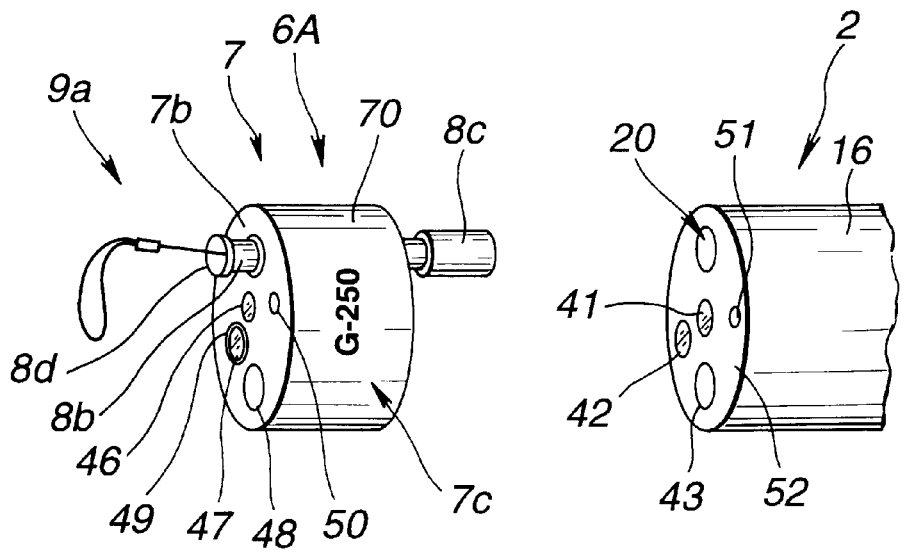
Figure 35:
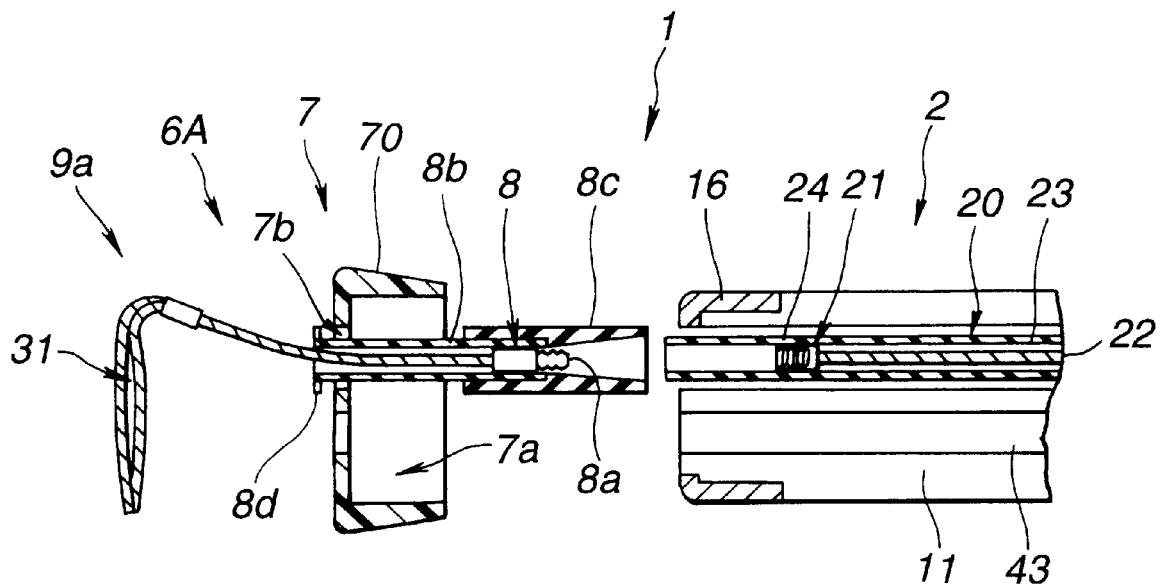

Referring to FIGS. 33 to 35, an eleventh embodiment of the present invention will be described below.

As shown in FIG. 33, an endoscope system 100 of this embodiment comprises a light source apparatus 3, a video processor 4, a monitor 5, and, for example, two electronic endoscopes (hereinafter, a first endoscope and second endoscope) 2 and 102. The first endoscope 2 includes first endoscope modules 6 such as an incision module 6A that has an incision device 9a and which is freely detachably attachable to the endoscope 2, a clamping module 6B having clamping members 9b, a biopsy module 6C having biopsy forceps 9c, and a collection module 6D having a basket type collector 9d. The second endoscope 102 includes second endoscope module 106 such as an incision module 106A having an incision device 9a and which is freely detachably attachable to the endoscope 102, a clamping module 106B having clamping members 9b, a biopsy module 106C having biopsy forceps 9c, and a collection module 106D having a basket type collector 9d.

The first endoscope 2 includes an insertion unit 11 that is elongated and is flexible, an operation unit 12 communicating with the proximal end of the insertion unit 11, and a universal cord 13 extending from the lateral side of the operation unit 12 and having flexibility. A connector 14 to be coupled to the light source apparatus 3 in a freely detachable fashion is attached to the end of the universal cord 13. A signal cord 15 is spliced to the lateral side of the connector 14. The signal cord 15 is coupled to a video processor 4 via the electric connector that is not shown so that it can be uncoupled freely.

The second endoscope 102 includes, like the first endoscope 2, an insertion unit 111 that is elongated and flexible, an operation unit 112, and a universal cord 113. A connector 114 is attached to the end of the universal cord 113. A signal cord 115 is spliced to the lateral side of the connector 114. The signal cord 115 is coupled to the video processor 4 via an electric connector that is not shown so that it can be uncoupled freely.

The monitor 5 for displaying an endoscopic image is connected to the video processor 4.

The endoscope modules 6A, 6B, 6C and 6D of the first endoscope modules each include a module body 7 having a body member 70, a treating means associated with a purpose of treatment or examination, and a module-side connecting tool 8 used to couple the treating means to the endoscope 2. The body member 70 has the outer surface thereof coated with an insulator or the whole of the body member is made of a resin material that is an insulator. This feature is intended to prevent electrical current leaks to the endoscope 2 which may cause an examining physician to undergo electrical shock.

Similarly, the endoscope modules 106A, 106B, 106C, and 106D of the second endoscope modules 106 each include, like the first endoscope modules 6, a module body 7 having a body member 170 made of an elastomer having elasticity and shaped substantially like a cylinder, a treating means associated with a purpose of treatment or examination, and a module-side connecting tool 108 used to couple the treating means to the endoscope 102. Like those of the first endoscope modules 6, the body member 170 is structured to prevent electrical current leaks to the endoscope 102 which may cause an examining physician to undergo electrical shock during a treatment procedure using a high-frequency current.

Moreover, the distal part of the insertion unit 11 of the endoscope 2 is the distal part 16 to which the body member 70 of any of the first endoscope modules 6 is attached. The distal pat 16 is provided with an endoscope-side connecting tool 21 to be joined with the module-side connecting tool 8 of any of the endoscope modules 6A, 6B, 6C or 6D. A transmission wire 22 extends from the proximal end of the endoscope-side connecting tool 21, through the insertion unit 11, and is coupled to an operation knob 17 mounted on the operation unit 12 By handling the operation knob 17, the treating means in the endoscope module attached to the distal part 16 can be maneuvered.

An indicator 7c serving as a matching means indicating the endoscope to be used in combination with the endoscope module is located on the outer surface of each body member 70. A symbol representing the model name of the endoscope 2 which indicates that the endoscope module matches the first endoscope 2 is written in the indicator 7c. A corresponding indicator 19 serving as a matching means that indicates that an endoscope module is used in combination with the endoscope 2 is located on the outer surface of the operation unit 12 of the first endoscope 2. A symbol indicating the model name of the first endoscope 2 is written in the indicator 19.

The distal part of the insertion unit 111 of the endoscope 102 is a distal part 116 to which the body member 170 of any of the second endoscope modules 106 is attached. The distal part 116 is provided with an endoscope-side connecting tool 121 to be coupled with the module-side connecting tool 108 of any of the endoscope modules 106A, 106B, 106C, and 106D of the second endoscope modules 106. A transmission wire 122 extends from the proximal end of the endoscope-side connecting tool 121, through the insertion unit 111, and is coupled to an operation knob 117 mounted on the operation unit. By handling the operation knob 117, the treating means in the endoscope module attached to the distal part 116 can be maneuvered.

An indicator 172 is provided on the outer surface of each body member 170. A symbol representing the model name of the endoscope 102 to thus indicate that the endoscope module is associated with the second endoscope 102 is written in the indicator 172. A corresponding indicator 119 is placed on the outer surface of the operation unit 112 of the second endoscope 102. A symbol indicating the model name of the second endoscope 102 is written in the indicator 119.

As shown in FIG. 34, an operation channel 20, through which the transmission wire 22 is provided, has a distal opening on the distal surface of the distal part 16 of the endoscope 2. Additionally, an observation window 41 located in front of an observation optical system that is not shown, an illumination window 42 through which illumination light for illuminating the interior of a body cavity is irradiated are mounted in the distal surface of the distal part 16 of the endoscope 2. Moreover, a treatment channel 43 through which debris is removed by suction or a treatment instrument is passed has its distal opening located on the distal surface of the distal part 16 of the endoscope 2. Furthermore, an opening 51 to an aeration/perfusion channel through which water and air used to clean the observation window 41 and illumination window 42 is provided in the distal surface of the distal part 16 of the endoscope 2.

By contrast, a treatment instrument passage hole 7b has its distal opening on the distal surface of the body member 70 of the incision module 6A and is located so as to oppose the distal opening of operation channel 20. Besides, an observation window cover 46 opposed to the observation window 41 and made of a transparent material, and an illumination window cover 47 opposed to the illumination window 42 and made of a transparent material are mounted in the distal surface of the body member 70 of the incision module 6A. Moreover, a treatment channel opening 48 located so as to oppose the treatment channel 43, and an aeration/perfusion nozzle 50 opposing the aeration/perfusion channel opening 51 are provided in the distal surface of the body member 70 of the incision module 6A. Characters "G-250" indicating the model name "GIF-250" of the first endoscope 2 is written in the indicator 7c on the body member 70. The characters "GIF-250" indicating the model name of the first endoscope 2 is written in the indicator 19 on the first endoscope 2. In addition, a light interceptor 49 surrounds the illumination window cover 47.

As shown in FIG. 35, when the incision module 6A having the incision device 9a is attached to the endoscope 2, the body member 70 is fitted onto the distal part 16. An internal space portion 7a is formed in the body member 70 whose inner diameter is made slightly smaller than the outer diameter of the distal part 16. The body member 70 is coupled to the distal part 16 with the inner circumference of the body member 70 in close contact with the outer circumference of the distal part 16.

An operation tube 23 in which the endoscope-side connecting tool 21 and transmission wire 22 can be advanced or withdrawn freely is inserted into the operation channel 20 in the endoscope 2 so that the operation tube 23 itself can be advanced or withdrawn freely. The proximal ends of the transmission wire 22 and operation tube 23 are coupled to the operation knob 17 mounted on the operation unit 12. The transmission wire 22 and operation tube 23 can be advanced or withdrawn mutually independently.

Now, the procedure of attaching the incision module 6A to the distal part 16 of the endoscope 2 will be described with reference to FIG. 35.

First, the endoscope-side connecting tool 21 fixed to the distal end of the transmission wire 22 is extended out of the operation tube 23 inserted through the operation channel 20. The module-side connecting tool 8 fixed to the back end of the incision device 9a is likewise extended out of a coupling member 8c. A male screw portion 8a of the module-side connecting tool 8 is engaged with a female screw 24 in the endoscope-side tool 21. Thus, the transmission wire 22 and incision device 9a are securely connected to each other.

Thereafter, the distal part of the operation tube 23 is press-fitted into a tapered portion of the coupling member 8c of the incision module 6A. This causes the operation tube 23 and the coupling member 8c to be joined to each other.

The structure of the first endoscope 2 including the incision module 6A attached thereto has been described so far. The structures of each of the other endoscope modules 6B, 6C and 6D as attached to the first endoscope 2, and the structure of the second endoscope 102 as attached to second endoscope modules 106 are identical to the structures of the incision module 6A as attached to the first endoscope 2. The description of these structures will therefore be omitted.

Moreover, the symbol "G-250" indicating that an endoscope module is associated with the first endoscope 2 is written in the indicators 7c on the body members 70 of the incision module 6A, clamping module 6B, biopsy module 6C, and collection module 6D of the first endoscope modules 6. In contrast, the characters "C-250", standing for "CF-M250" which is the model name of the second endoscope 102, indicates that an endoscope module is associated with the second endoscope 102 and is written in the indicators 172 on the body members 170 of the incision module 106A, clamping module 106B, biopsy module 106C, and collection module 106D of the second endoscope modules 106. The characters "CF-M250" is correspondingly written in the indicator 119, which is not shown on the second endoscope 102.

Furthermore, the endoscope system 100 of this embodiment comprises a group including the first endoscope 2 and the first endoscope modules 6 capable of being used in combination with the first endoscope 2, and a group including the second endoscope 102 and the second endoscope modules 106 capable of being used in combination with the second endoscope 102. However, the endoscope system 100 is not limited to a configuration consisting of only two groups. Alternatively, the endoscope system 100 may be configured so that one or more groups each including another endoscope and endoscope modules capable of being used in combination with the associated endoscope are additionally included. In this case, needless to say, the symbol or characters to be written in the indicators are differentiated between the different groups so that the groups can be distinguished from one another.

As mentioned above, an endoscope system of the present invention has a plurality of groups each composed of an endoscope and a plurality of endoscope modules to be used in combination with the endoscope. The same number of endoscopes and sets of endoscope modules are provided to match the number of groups present. An endoscope and a plurality of endoscope modules to be used in combination with the endoscope are each provided with an indicator having a symbol or characters which indicate that the plurality of endoscope modules are to be used in combination with the endoscope. By distinguishing the indicators, it can be easily determined which endoscope modules are matched with which endoscope.

This feature can solve the drawback that an endoscope module and endoscope are attached imperfectly to each other because of mismatch or than an endoscope module and endoscope cannot perform efficiently or as intended because they have been incorrectly and forcibly attached to each other. For example, assume that the first endoscope is dedicated to the superior alimentary canal and is therefore inserted into the esophagus, stomach, and duodenum through the mouth during use, and that the second endoscope is dedicated to the inferior alimentary canal and is therefore inserted into the intestine through the anus during use. In this case, the endoscope system of the present invention prevents an endoscope and endoscope module from being combined incorrectly.

Instead of providing a symbol of characters in an indicator to serve as the matching means, the colors of the module bodies of the first endoscope modules 6 and the colors of the module bodies of the second endoscope modules 106 may be made to be different from each other. For example, the module bodies of the first endoscope modules may be colored in yellow, while the module bodies of the second endoscope modules 106 may be colored in green. The distal part 16 of the first endoscope 2 to which the first group of modules 6 is attached may be likewise colored in yellow, while the distal part 116 of the second endoscope 102 may be correspondingly colored in green. Thus, which endoscope module matches which endoscope can be determined instantaneously. With this embodiment, the module bodies and the distal parts of the associated endoscopes may be colored entirely or partly. For example, assume that both the module bodies and the distal parts of the endoscopes are colored in black or made of a transparent material. In this case, the indicators 7c and 172 on the module bodies are colored in yellow and green, and the indicators 19 and 119 on the endoscope are respectively colored in yellow and green.

In another alternative, assume that the first endoscope 2 is dedicated to the superior alimentary canal and is therefore inserted into the esophagus, stomach, and duodenum through the mouth during use, and the second endoscope 102 is dedicated to the inferior alimentary canal and therefore inserted into the large intestine through the anus during use. In this case, the outer diameters of the endoscopes dedicated to the superior and inferior alimentary canals may be significantly different from each other so as to physically prevent incorrect combination of an endoscope and endoscope module.

To be more specific, the sizes of the body members 70 and 170 of the endoscope modules 6 and 106 and the sizes of the distal parts 16 and 116 of the endoscopes 2 and 102 may be clearly differentiated from each other. For example, the outer diameter of the distal part 16 is 9 mm and the outer diameter of each of the body members 70 is 11 mm, while the outer diameter of the distal part 116 is 12 mm and the outer diameter of each of the body members 170 is 14 mm. Even when all the module bodies and distal parts are the same color if the differences in outer diameter are 10% or higher, they can be identified upon sight. Such structure would obviate the necessity of color coding the module bodies and endoscopes, which simplifies the manufacturing process. Thus, in this embodiment of endoscope system 100, the outer diameters of the body members 70 and 170, and accordingly, the dimensions of the portions of the body members 70 and 170 which engage the endoscopes 2 and 102 are mutually differentiated to agree with the sizes of the distal parts 16 and 116, respectively.

While the diameter of an endoscope dedicated to the superior alimentary canal may be made to be larger than that of an endoscope dedicated to the inferior alimentary canal, generally however, the endoscope dedicated to the superior alimentary canal is thinner than the endoscope dedicated to the inferior alimentary canal. In the endoscope system 100 described above, assuming that the first endoscope 2 is dedicated to the superior alimentary canal and the second endoscope 102 is dedicated to the inferior alimentary canal, one of ordinary skill in the art would expect that there would be a difference in size between the body members 70 and 170 and between the distal parts 16 and 116. By increasing the differences in size to 10% or greater, it becomes easier to determine which module matches which type of endoscope.

In use, an endoscope dedicated to the inferior alimentary canal is inserted into the patient's body by frequently pushing or pulling the insertion unit thereof or by twisting the insertion unit for a prolonged period of time. In this manner, an enormous load (external force) is imposed on the insertion unit of the endoscope dedicated to the inferior alimentary canal during insertion, as compared to the load required to insert an endoscope dedicated to the superior alimentary canal. For this reason, only the endoscope dedicated to the inferior alimentary canal would necessitate the threaded structure as shown in FIG. 16 or 19. Based on this structure, the difference between a group composed of the endoscope dedicated to the inferior alimentary canal and associated endoscope modules and a group composed of the endoscope dedicated to the superior alimentary canal and associated endoscope modules can be discerned by checking for the presence of the through-hole or female screw portion. With this embodiment, one or a plurality of fixtures, i.e., screws, may be provided to secure the connection. A plurality of fixtures would serve to intensify the connection strength when attaching any module body to the distal part of the endoscope. Specifically, the endoscope dedicated to the inferiority alimentary canal may be provided with a plurality of fixtures such as screws. In this case, the difference between the group composed of the endoscope dedicated to the inferior alimentary canal and associated endoscope modules and the other group can be discerned by the difference in the number of through-holes present.

As another alternative, the position of a screw in the direction of the longitudinal axis of the endoscope may be differentiated from group to group. In this manner, the difference between the groups can be discerned. Furthermore, incorrect attachment can be physically prevented.

In another embodiment of the endoscope system of the present invention, one group of an endoscope and associated endoscope modules may be provided with the jut and groove shown in FIG. 20. The other group of an endoscope and associated endoscope modules may be provided without the jut and groove. This makes it possible to distinguish between the groups each composed of an endoscope and associated endoscope modules by checking for the presence of the jut and groove, assuming that the sizes of the first endoscope and the first endoscope modules and the sizes of the second endoscope and second endoscope modules are very close to each other. Even if an attempt is made to attach any of the first endoscope modules to the second endoscope, the difference in the presence or absence of the jut and groove will prevent the erroneous attachment. In other words, since the groove in which the jut is fitted is not formed in the second endoscope, the first endoscope modules cannot be attached to the second endoscope. The user will then recognize that he/she has attempted to perform an incorrect attachment. Thus, the incorrect attachment is prevented.

In yet another alternative embodiment, the first endoscope 2 and second endoscope 102 may be differentiated from each other by changing the position of the operation channel 20 through which the transmission wire 22 extends relative to the central axis of the endoscope. Here, the different positions of the treatment instrument passage holes 7b in the body members 70 and body members 170 relative to the central axes serve to distinguish each other according to the associated endoscopes.

Due to the foregoing structures, even when the sizes of the distal parts and/or the sizes of the module bodies are substantially the same in the different groups, a distal part and module body other than those belonging to the same group will therefore not be attached to each other. Consequently, the user will recognize that he/she has attempted to perform an incorrect attachment. In such manner, incorrect attachments can be prevented.

Referring to FIGS. 36 to 39, a twelfth embodiment of the present invention will be described below.

Figure 36:
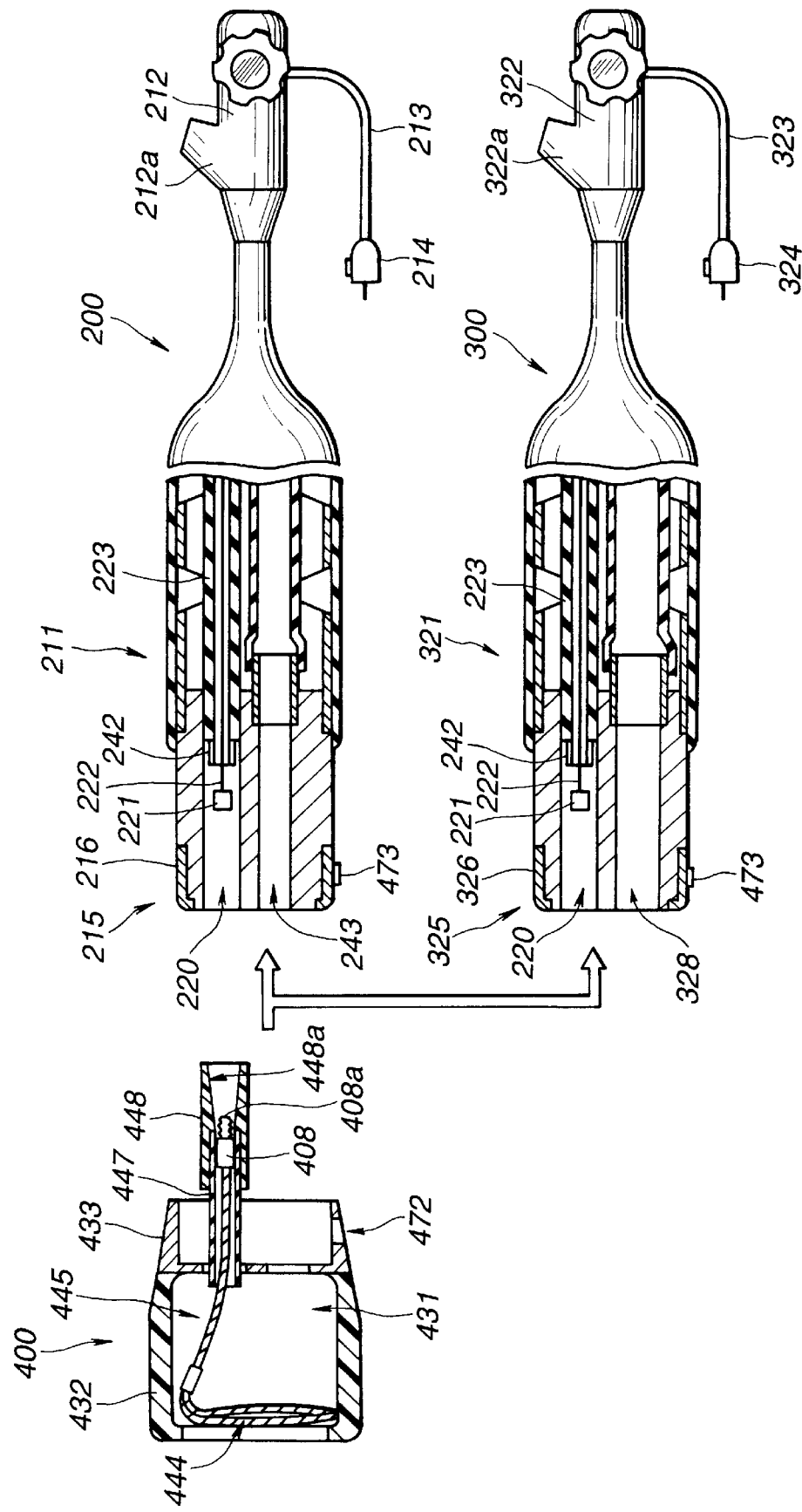
FIGS. 36 to 39 are diagrams for explaining a twelfth embodiment of the present invention.

As shown in FIG. 36, an endoscope system of this embodiment comprises a first endoscope 200, a second endoscope 300, and an endoscope module 400 designed for incision and which is selectively and detachably attachable to the first endoscope 200 and the second endoscope 300 (hereinafter, an incision module).

The first endoscope 200 includes an insertion unit 211, an operation unit 212, a universal cord 213, and a connector 214. A first locking member 216 serving as a coupling means and making it possible to freely detachably attach the incision module 400 is provided on the outer circumference of a distal part 215 of the insertion unit 211. The first locking member 216 is made of a magnet or a metal to be attracted by a magnet, and is painted in a color different from the surrounding components, for example, red.

In the distal surface of the distal part 215, there are the openings of an operation channel 220 through which a transmission wire 222 used to transmit an operation force to the incision module 400 is provided and which can be advanced or withdrawn freely, of a suction channel 243, and an aeration/perfusion channel communicating with a cleaning nozzle used to wash out debris or water drops from the surface of a lens included in an objective optical system or illumination optical system that is not shown.

An endoscope-side connecting tool 221 serving as a coupling means and operation force transmitting means, having a cylindrical shape, and having an inner surface thereof threaded as a female screw 224 is fixed to the distal end of the transmission wire 222. The transmission wire 222 is enclosed in a tube 223 that is fitted in a reticular duct and that has the distal lateral side thereof threaded as a male screw portion 242. The tube 223 is fixed in a watertight fashion to the lumen of the operation channel 220 formed in the rigid distal part 215 by applying an adhesive or the like.

The incision module 400 is made of a hard resin material, for example, polyolefine, polycarbonate, ABS polyamide, vinyl chloride, latex, or natural rubber, and shaped substantially like a pipe. The incision module 400 comprises a body member 432 having a treatment hollow 431 in which a lesion can be placed, a first magnet 433 fixed to the proximal end of the body member 432, and designed to also serve as a coupling means and to act as a fitting member to be fitted on the first locking member 216 of the endoscope 200, and an incision device 445 that is a treating means including, for example, an annular incising member 444.

The incision device 445 has the incising member 444 at one side thereof. A module-side coupling member 408 having a male screw portion 408a that can be engaged with a female screw 224 threaded in the endoscope-side connecting tool 221 of the endoscope 200, a treatment operation tube 447 capable of advancing or withdrawing freely relative to the body member 432, and a coupling member 448 having the internal circumference of the proximal end thereof threaded as a female screw 448a to be engaged with the male screw portion 242 of the tube 223, and made of a hard resin material, for example, polyolefine, polycarbonate, ABS, polyamide, vinyl chloride, latex, or natural rubber, or a metallic material are formed on the other side of the incision device 445.

Figure 37:
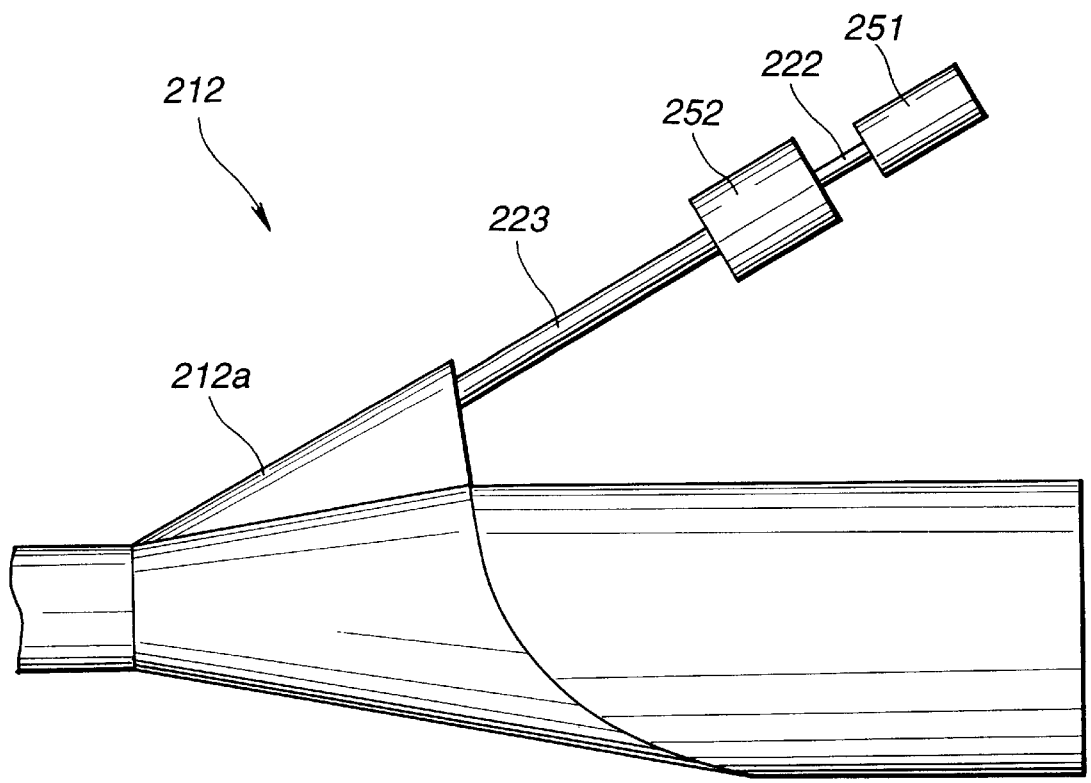

As shown in FIG. 37, for example, the transmission wire 222 and tube 223 are extending through an opening end 212a of the operation unit 212 of the first endoscope 200. A first knob 251 is fixed to the proximal end of the wire 222, and a second knob 252 is fixed to the proximal end of the tube 223.

The second endoscope 300 includes, like the first endoscope 200, an insertion unit 321, an operation unit 322, a universal cord 323, and a connector 324. A second locking member 326 also serving as a coupling means and making it possible to freely detachably attach the incision module 400 is placed on the outer circumference if the distal part 325 of the insertion unit 321. The outer diameter of the second locking member 326 and the outer diameter of the first locking member 216 are set to the same value.

The second endoscope 300 has a suction channel 328. The inner diameter of the suction channel 328 is larger than the inner diameter of suction channel 243 in the first endoscope 200. Consequently, the second endoscope 300 provides a larger magnitude of suction than the first endoscope 200.

Moreover, an target organ into which the second endoscope 300 is inserted is a long organ such as the large intestine. The insertion unit 321 is therefore longer than the insertion unit of the first endoscope 200. The other components of the second endoscope 300 are identical to those of the first endoscope 200. The same reference numerals will be assigned to the same members. The description of those members will therefore be omitted.

A bore 472 is formed in the body member 432 so that when the incision module 400 is attached to either the first endoscope 200 or the second endoscope 300, it can be easily checked if the endoscope module 400 has been attached in a proper state. A mark 473 having a color different from the color of its surroundings is located at the position on the circumference of the first endoscope 200 and on the second endoscope 300 at which the mark will be opposed to the bore 472.

Figure 38:
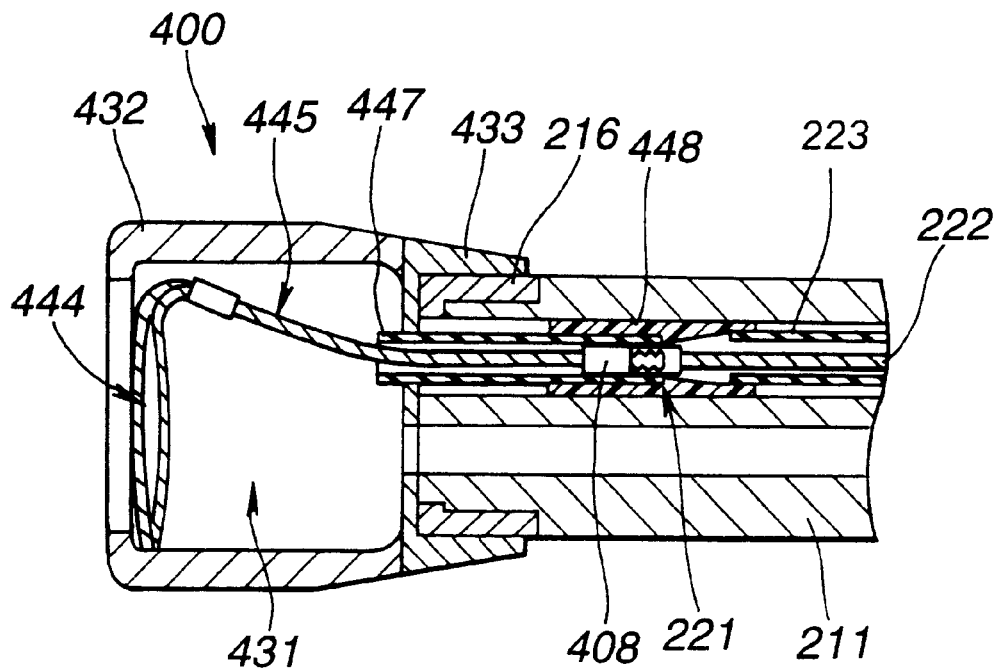

Referring to FIG. 38, the procedure of attaching the incision module 400 to the first endoscope 200 will be described below.

First, the endoscope-side connecting tool 221 fixed to the distal end of the transmission wire 222 is extended out of the operation channel 220. The module-side coupling member 408 fixed to the back end of the incision device 445 is likewise extended out of the coupling member 448. The male screw portion 408a of the module-side coupling member 408 is engaged with the female screw 224 of the endoscope-side connecting tool 221. Thus, the transmission wire 222 and incision device 445 are securely connected to each other.

Thereafter, the male screw portion 242 that is the distal portion of the tube 223 is extended out of the operation channel 220. The female screw 448a in the coupling member 448 and the male screw portion 242 are engaged with each other. The tube 223 and coupling member 448 are securely fixed to each other.

Thereafter, the first magnet 433 of the body member 432 is slid in the direction of the longitudinal axis of the insertion unit relative to the first locking member 216 on the distal part 215 of the first endoscope 200. With a magnetic force exerted by the first magnet 433, the body member 432 is attracted to the first locking member 216. Thus, attachment is completed.

Figure 39:
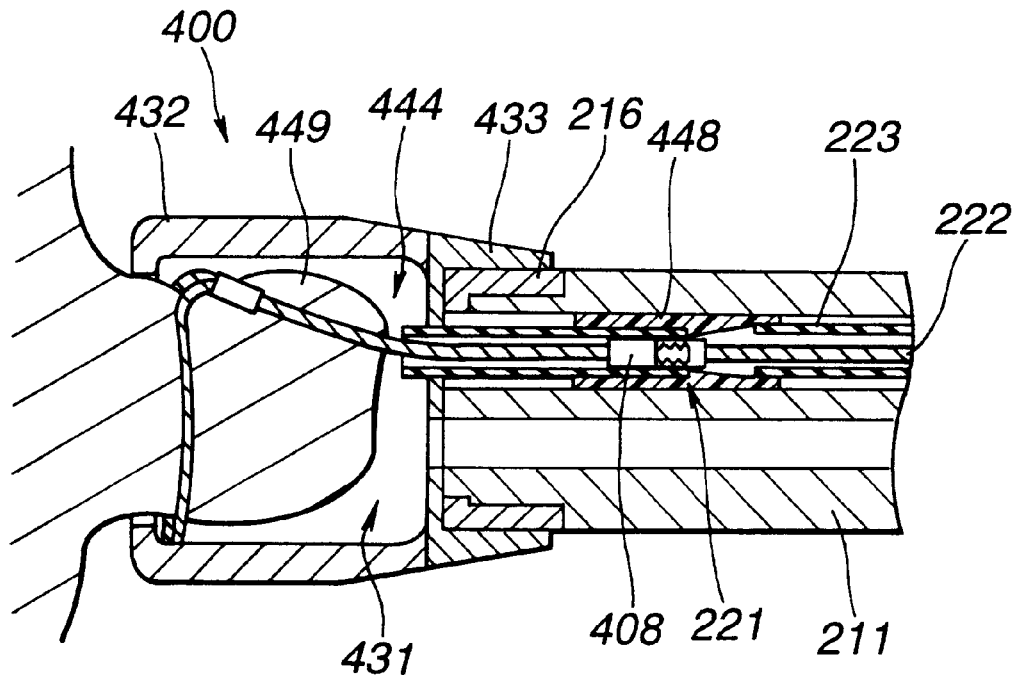

Referring to FIG. 39, the method of operating the endoscope 200 with the incision module 400 attached to the first locking member 216, and the functions of the endoscope 200 will be described below.

First, the endoscope 200 having the incision module 400 attached to the first locking member 216 is inserted into, for example, a body cavity. The body member 432 is then positioned near a lesion 449.

Thereafter, the first knob 251 at the proximal end of transmission wire 222 (FIG. 37) is pushed toward the second knob 252 at the proximal end of the tube 223 to extend incision member 445 out of body member 432 in order to trap the lesion 449 to be incised with the incising member 444 of the incision device 445. As the incising member 444 moves forward, the lesion 449 becomes trapped inside incising member 444.

Thereafter, the first knob 251 is withdrawn relative to the second knob 252. This causes the incision device 445 to be pulled inside treatment operation tube 447 to be adjacent the first magnet 443. The loop of the incising member 444 thereby gets smaller, whereupon the lesion 449 is fastened inside treatment hollow 431.

In the fastened state, a high-frequency current is supplied to the incision module 400. Consequently, the lesion 449 is cut at the root thereof. In this manner, the treatment is completed.

After completion of the treatment, the endoscope 200 is removed from the body cavity, and the incision module 400 is detached from the endoscope 200. The procedure of detaching the incision module is the reverse of the procedure of attachment. Specifically, the body member 432 is first dismounted from the first locking member 216. Thereafter, the male screw portion 242 of the operation tube 223 is disengaged from the female screw 448a in the coupling member 448. The female screw 224 in the endoscope-side connecting tool 221 is then disengaged from the male screw portion 408a of the module-side coupling member 408. This causes the endoscope 200 and incision module 400 to separate from each other.

Referring to FIGS. 38 and 39, the procedure of attaching the incision module 400 to the first endoscope 200, and the operations of the first endoscope 200 having the incision module 400 attached to the distal part 215 thereof have been described. The procedure of attaching the incision module 400 to the distal part 325 of the second endoscope 300 and the operations of the second endoscope 300 having the incision module 400 attached to the distal part 325 thereof are identical to the procedure of attaching the incision module 400 to the first endoscope 200 and the operations of the first endoscope 200 having the incision module 400 attached to the distal part thereof 215.

As mentioned above, the outer diameters of a first locking member and second locking member of the two endoscopes are set to the same value. Thus, one type of incision module can be attached selectively to both the first endoscope and second endoscope Moreover, a magnetic force exerted by a first magnet included in the endoscope module is used to affix the endoscope module to a first locking member or a second locking member. The workability in attaching the endoscope module to the distal part of the insertion unit of the endoscope can thus be improved drastically.

Furthermore, the direction of the contacting surfaces in which the locking member and fitting member are joined with each other is the direction of the longitudinal axis of the insertion unit. The fitting member will therefore not interfere with an objective optical system or the like at the distal end of the insertion unit. The outer diameter of the distal part can therefore be decreased.

Moreover, when the first magnet is fitted on the first locking member or second locking member, the first magnet and locking member contact each other along a given length in the direction of the longitudinal axis of the insertion unit. The first magnet can therefore be fitted on the locking member in a stable manner.

Moreover, when the first magnet is properly fitted on the first locking member or the second locking member, the first locking member or second locking member, which has a color different from the color of its surroundings, is fully covered by the first magnet. It can therefore be easily checked if the endoscope module has been attached in the proper position.

Moreover, the distal parts of the first endoscope and second endoscope are painted in a color different from the color of the surroundings, for example, in red. The endoscopes can therefore be easily distinguished from endoscopes whose distal parts are not of that color and which are not of a modular type.

Moreover, the distal part of the first endoscope or second endoscope to which the incision module is not attached is painted in a color different from the color of the surroundings, for example, in red. Consequently, an examination with the incision module left unattached to the endoscope can be prevented.

Instead of including the first magnet 433 in the body member 432, an elastic fixing member whose inner diameter is smaller than the inner diameter of the first magnet or the outer diameter of the first locking member 216 and second locking member 326 in a natural state may be employed as an alternative. When the elastic fixing member is attached to the first locking member 216 or second locking member 326, the elastic fixing member deforms to dilate because of its elasticity. A restoration force exerted by the elastic fixing member acts as a fastening force. The incision module having the elastic fixing member can therefore be fixed to the first endoscope 200 or second endoscope 300.

Moreover, a concave part extending in the circumferential direction may be formed along the outer circumferences of the first locking member 216 and of the second locking member 326. A convex part to be mated with the concave part may be formed along the inner circumference of the elastic fixing member of the incision module 400. In this case, when the incision module 400 is attached to the first locking member 216 or second locking member 326, the convex part is fitted into the concave part. Consequently, the incision module can be fixed to the first endoscope 200 or second endoscope 300 more reliably.

Figure 40:
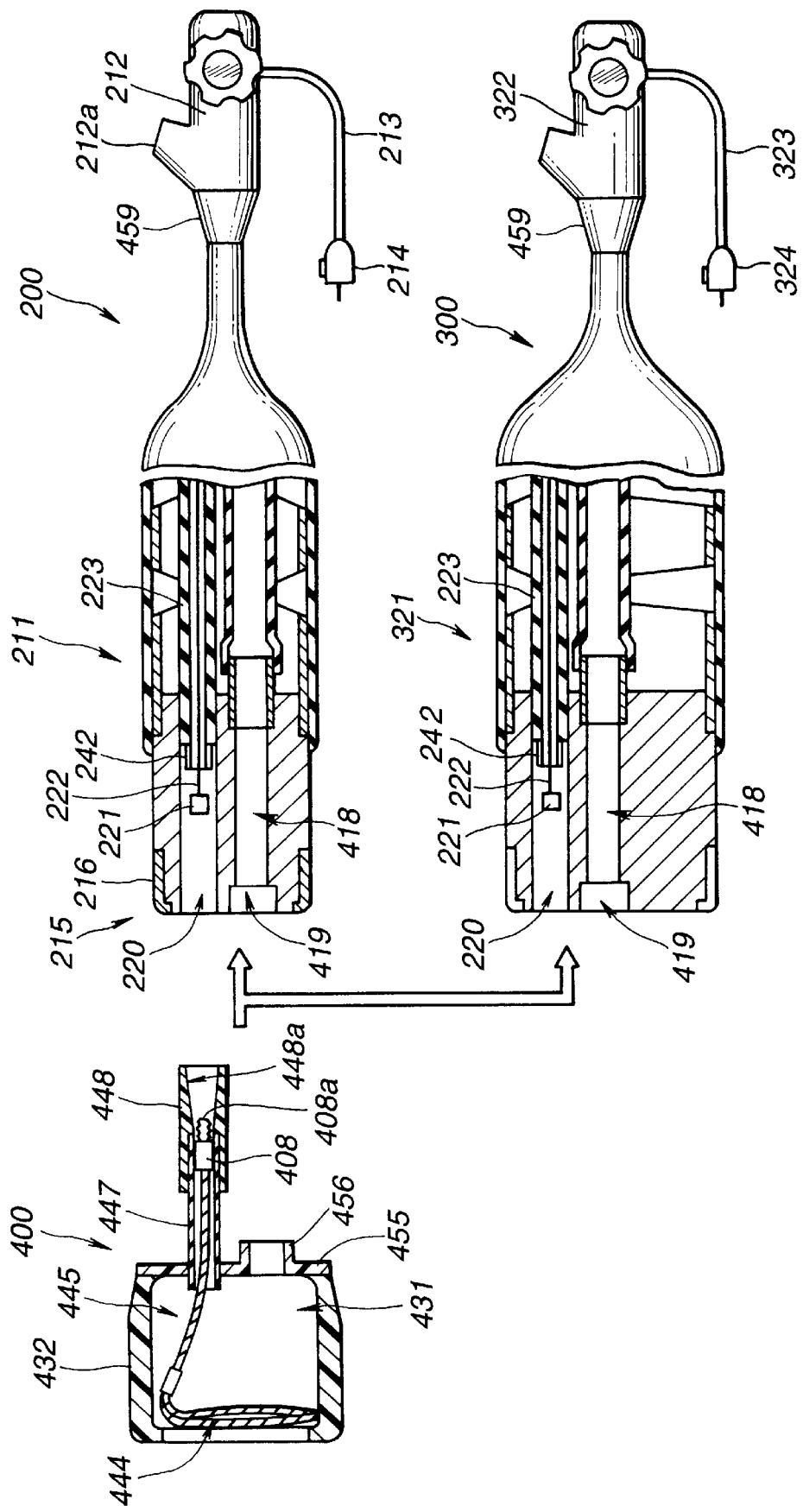
FIGS. 40 and 41 are diagrams for explaining a thirteenth embodiment of the present invention.
Figure 41:
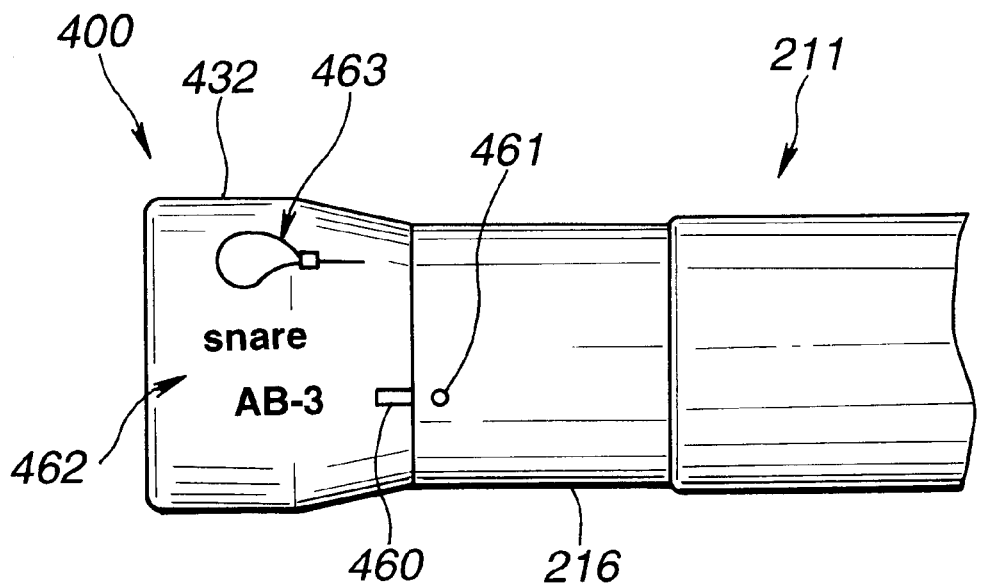

Referring to FIGS. 40 and 41, a thirteenth embodiment of the present invention will be described below.

As shown in FIG. 40, in an endoscope system of this embodiment, an attachment member 455 designed to also serve as a coupling means and made of an elastomer having elasticity is fixed to the proximal end of a body member 432 in place of the first magnet 433. Attachment member 455 is shaped substantially like a pipe and is designed to serve as a coupling means and to act as a fitting member to be fitted on the first locking member 216 of the endoscope 200. A tubular convex part 456 serving as a coupling means is formed at a position which coincides with the position of a suction channel 418 in the endoscope 200 and extends out from the proximal surface of the attachment member 455.

On the other hand, an extended recess 419 whose diameter is slightly smaller than the outer diameter of the convex part 456 is formed at the distal end of the suction channel 418 in the endoscope 200 so as to receive convex part 456.

A second endoscope 300 of this embodiment includes an objective optical system that is superior to an objective optical system in the first endoscope 200. The outer diameter of insertion unit 321 is therefore larger than the outer diameter of insertion unit 211 of the first endoscope 200. However, the same extended recess 419 as the one formed in the first endoscope 200 is formed at the distal end of suction channel 418 in the second endoscope 300. The extended recesses are located at the same position relative to operation channels 220 in both the first endoscope 200 and second endoscope 300.

The convex part 456 of the incision module 400 which acts as a fitting member is inserted into the extended recess 419 of the first endoscope 200 or second endoscope 300 which acts as a locking member. Due to an elastic force exerted by the convex part 456, the incision module 400 and first endoscope 200 or second endoscope 300 are securely fixed to each other.

An indicator 459 having a color different from the color of its surroundings is provided on an operation unit 212 of the first endoscope 200 and an operation unit 322 of the second endoscope 300 near the proximal end of the insertion units thereof. Characters "module" meaning that the endoscopes 200 and 300 are of a modular type are written in the indicator 459.

Moreover, as shown in FIG. 41, a line 460 serving as an instructing marker is inscribed on the outer circumference of the body member 432 near the convex part 456. For example, a circle 461 serving as an index for the line 460 is inscribed on the endoscopes 200 and 300 to which the body member 432 is attached.

When the incision module 400 is attached to the first endoscope 200 or second endoscope 300, the circle 461 is opposed to the line 460. This ensures that the incision module has been attached to the proper position. Characters 462 indicating "snare" and a mark 463 which represents the capability of the incision module 400 are inscribed together with the line 460 on the outer circumference of the body member 432.

As mentioned above, a convex part of the module is fitted into an extended recess in the suction channel of the endoscope. Due to an elastic force exerted by the convex part, the endoscope module can be securely fixed to the distal end of the endoscope. The same type of incision module can therefore be attached to endoscopes whose insertion units have different outer diameters as long as the suction channels in the endoscopes have almost the same diameter. This feature greatly improves the user-friendliness of the modular endoscope system of the present invention.

Moreover, an endoscope can be identified easily by checking for the characters "module" written in an indicator on the operation unit or for the color of the indicator.

Furthermore, the endoscope module may be considered to be properly attached to the endoscope when the line inscribed on the endoscope module is juxtaposed to the circle inscribed on the endoscope.

Consequently, the incision module and the first endoscope or second endoscope can be easily and properly positioned by turning.

Moreover, since the line and circle are inscribed near the fitting member and locking member, the relative positions of the fitting member and locking member can be determined readily. After the line and circle are aligned with each other the incision module is attached to the first endoscope or second endoscope. Thus, proper positioning can be achieved readily in the course of attachment.

Furthermore, characters or a mark inscribed on the outer circumference of the module body enable the capability or model of the endoscope module to be identified readily.

Figure 42:
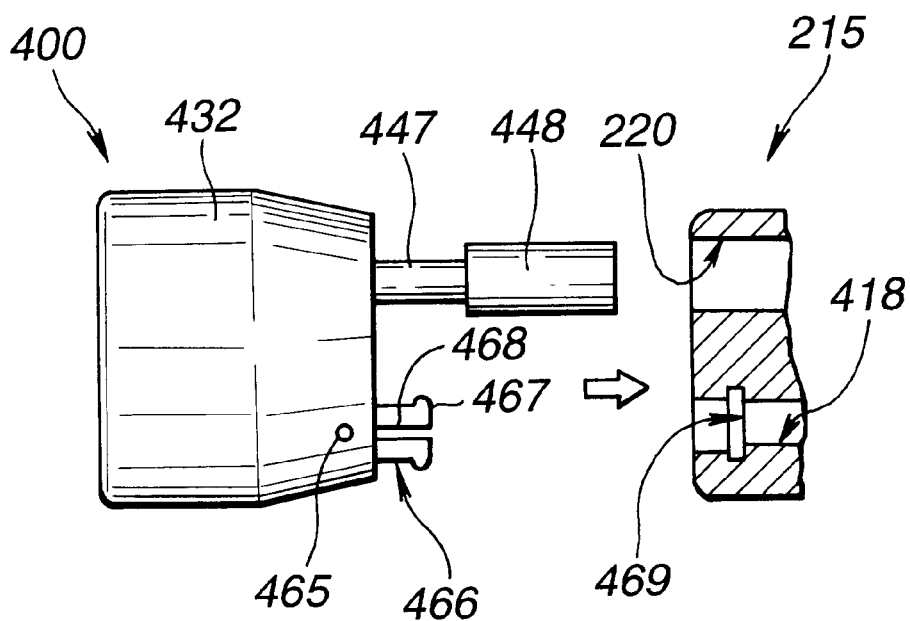
FIG. 42 is a diagram for explaining a variant of the thirteenth embodiment, and for explaining an endoscope module having a coupling means of a different structure.

Referring to FIG. 42, a variant of the thirteenth embodiment will be described below.

As illustrated in this embodiment, instead of the convex part 456, an arm 466 is formed as part of the body member 432. The arm 466 is composed of a collar 467 extending from the end of the body member on the side of the endoscope in the direction of the outer circumference, and the slit 468 extending in the direction of the longitudinal axis of the insertion unit. The projection 467 elastically deforms in a radial direction.

On the other hand, a groove 469 serving as a fitting member into which the collar 467 is fitted is formed at the distal end of the suction channel 418. When the back end surface of the body member 432 and the distal surface of the distal part 215 are brought into contact with each other, the arm 466 elastically deforms. The collar 467 is then fitted in the groove 469. When the collar 467 attempts to dilate in the direction of the outer circumference due to its elastic force, the endoscope 200 or 300 and the endoscope module 400 become securely attached to each other.

Figure 43:
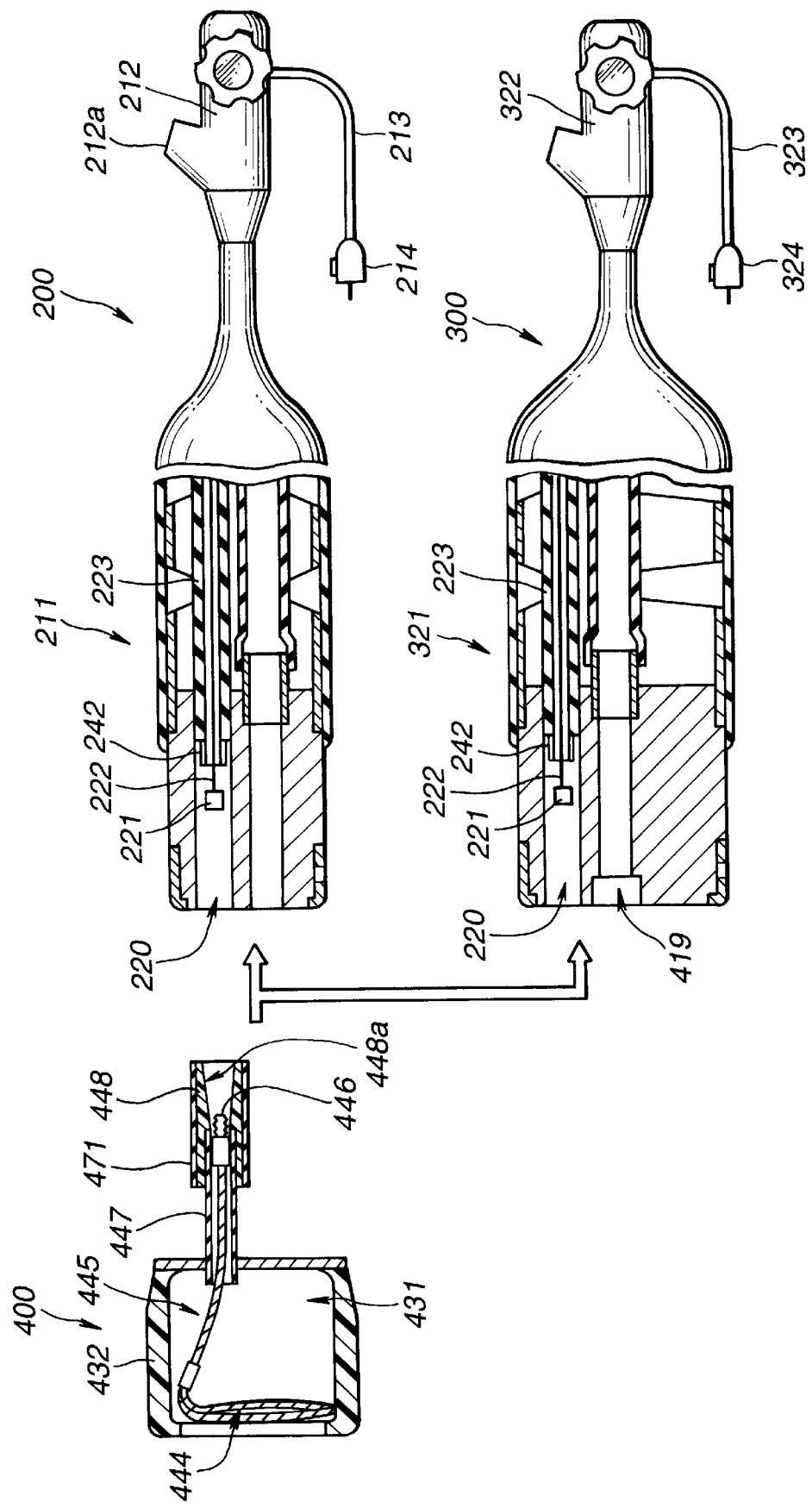
FIG. 43 is a diagram for explaining a fourteenth embodiment of the present invention and for explaining another structure of an endoscope system having a coupling means of a different structure.

Referring to FIG. 43, a fourteenth embodiment of the present invention will be described below.

As shown in FIG. 43, in this embodiment, an elastic member 471 made of an elastomer having elasticity, for example, vinyl chloride resin, silicone, natural rubber, isoprene rubber, or neoprene rubber and designed to serve as a coupling member is placed on the outer circumference of the coupling member 448.

The outer diameter of the elastic member 471 is slightly larger than the inner diameter of the operation channel 220 serving as a locking member. When the coupling member 448 is inserted into the operation 220, the endoscope module is securely fixed to the distal part of the endoscope due to the elastic force exerted by the elastic member 471 placed on the outer circumference of the coupling member 448.

As mentioned above, a restoration force stemming from elastic deformation of the elastic member is used to secure the endoscope module to the first endoscope or second endoscope. Even when endoscopes having different outer diameters or including suction channels whose inner diameters are different are used in combination with the endoscope module of this embodiment, as long as the fitting member of the endoscope module remains unchanged, the endoscope module can be attached to the different endoscopes. Thus, the same endoscope module can be used in common among endoscopes that are designed according to a wide range of specifications.

Figure 44:
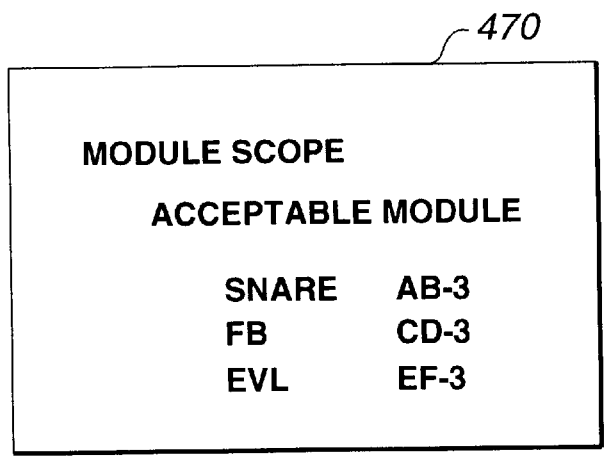
FIG. 44 is a diagram for explaining a fifteenth embodiment, and showing an example of a display on a monitor.

Referring to FIG. 44, a fifteenth embodiment of the present invention will be described below.

A CCD (not shown) is located on the image plane of an objective optical system in a first endoscope 200 or second endoscope 300. Data acquired by the CCD is transmitted to a video processor via a connector 214 or 324. An image signal is then produced. The produced image signal is transmitted to a monitor, whereupon an endoscopic image is then displayed on the monitor.

The first endoscope 200 and second endoscope 300 each have a ROM or CPU incorporated therein. ID data indicating that the endoscope is of the type to which a particular endoscope module is attachable is recorded in the ROM or CPU.

In this embodiment, the ID data is utilized to match the modules to endoscopes. In other words, the ID data is checked to see which module can be used in combination with an identified endoscope.

To be more specific, the first endoscope 200 or second endoscope 300 is connected to the processor. The processor is switched on. A screen 470 displaying ID information read from the ROM or the like incorporated in the endoscope is, as shown in FIG. 44, shown on the monitor. A message indicating that the endoscope is of a modular type and further indicating the types of modules that can be combined with the endoscope are displayed in the screen 470.

As mentioned above, data representing the specification of an endoscope is recorded in advance in a ROM or the like incorporated in the endoscope. The specification of the endoscope and the types of endoscope modules associated with the endoscope can be identified by checking the data displayed on the monitor.

Referring to FIGS. 45 to 52, a sixteenth embodiment of the present invention will be described below.

Figure 45:
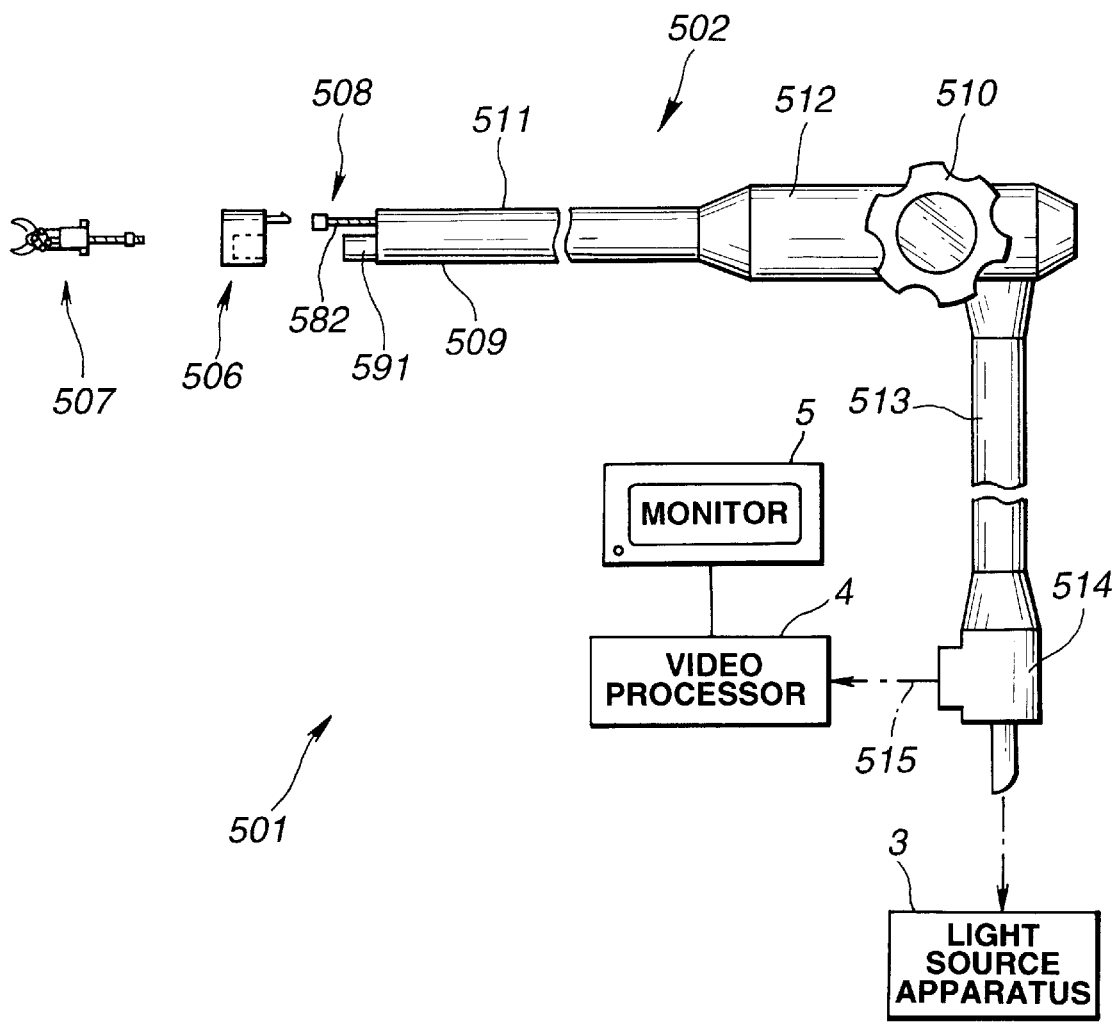

As shown in FIG. 45, an endoscope system 501 of this embodiment comprises an electronic endoscope (hereinafter endoscope) 502, a light source apparatus 3, a video processor 4, a monitor 5, a module body 506 in which a plurality of treatment instruments can be mounted and which can be coupled to the endoscope 502 via a coupling means, and a treatment member 507 having a treatment instrument that serves as a treating means to be mounted in the module body 506.

The endoscope 502 includes an insertion unit 511 that is elongated and flexible, an operation unit 512 communicating with the proximal end of the insertion unit 511, and a universal cord 513 extending from the lateral side of the operation unit 512 and having flexibility. The insertion unit 511 is provided with a distal part 509 having a convex part 591 thereof shaped substantially like a sideways letter D (See FIG. 49). An endoscope-side connecting tool 508 shaped like a cylinder and having an inner circumference thereof threaded as a female screw (581 in FIG. 50B). A control wire 582 extends proximally from the endoscope-side connecting tool 508.

The proximal end of the control wire 582 is coupled to a handle 510 mounted on the operation unit 512 of the endoscope 502. By turning the handle 510, the control wire 582 is advanced or withdrawn.

The operation unit 512 is provided with another handle, which is not shown, on the opposite side thereof relative to the handle 510. The handles act mutually independently. Moreover, the operation unit 512 is provided with still another operation handle (not shown) for angling a bending portion (not shown) so that the distal part 509 will be angled in a desired direction.

A connector 514 to be coupled to the light source apparatus 3 in a freely detachable fashion is spliced to the end of the universal cord 513. A signal cord 515 extends from the lateral side of the connector 514. The signal cord 515 is spliced to the video processor 4 via an electrical connector that is not shown. The monitor 5 for displaying an endoscopic image is connected to the video processor 4.

Figure 46:
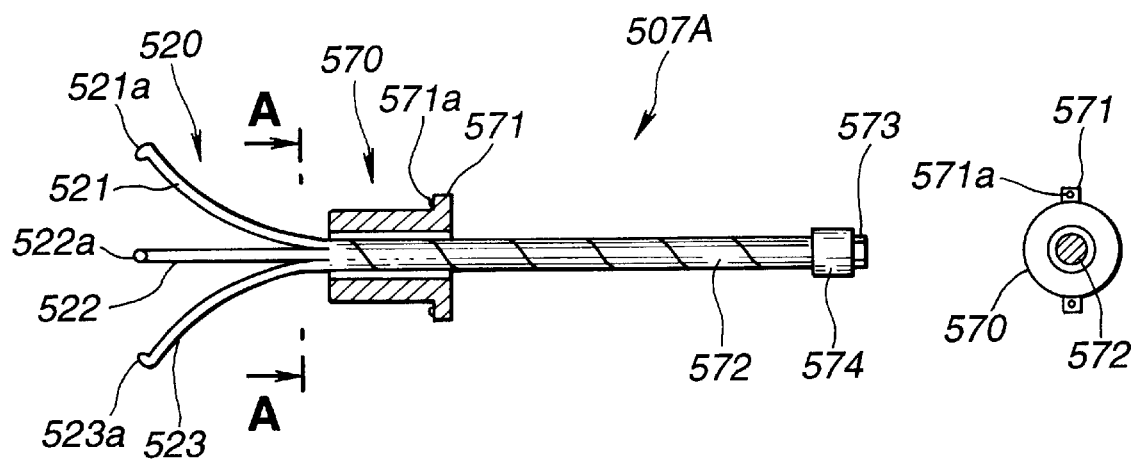

As shown in FIG. 46, a tripod-like forceps member 520 is fixed to a treatment instrument placement member 570. The treatment instrument placement member 570 is an attachment member shaped substantially like a pipe and having locking portions 571 which jut out from the outer circumference of the treatment instrument placement member 570, at the back end thereof. The forceps member 520 is then mounted in the module body 506. Thus, the treatment member 507 shown in FIG. 46 is structured as clamps 507A serving as an endoscope module.

Convex parts 571a provide means to check for proper attachment and are formed on the distal surfaces of the locking portions 571.

The forceps member 520 includes elastic clamping members 521, 522, and 523 having clamping portions 521a, 522a, and 523a, respectively, at the distal ends thereof and which are inclined to bend by a given magnitude. The elastic clamping member 521, 522, and 523 are spliced to the distal end of an operation wire 572. A coupling member 574 having a male screw portion 573 is fixed to the proximal end of the operation wire 572.

The treatment member 507 can be structured to provide a plurality of endoscope modules by affixing different treatment instruments associated with different purposes of treatments and examinations to the distal end of the operation wire 572.

Figure 47A:
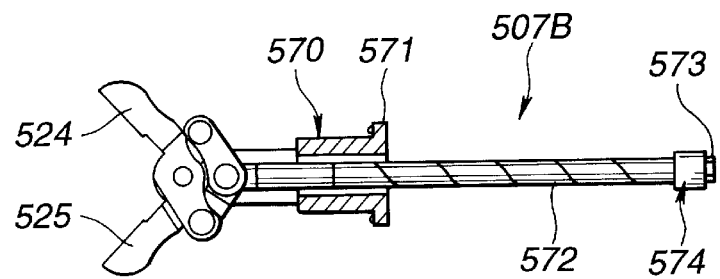
FIGS. 47A to 47D are diagrams for explaining other examples of treatment members of the sixteenth embodiment.
Figure 47B:
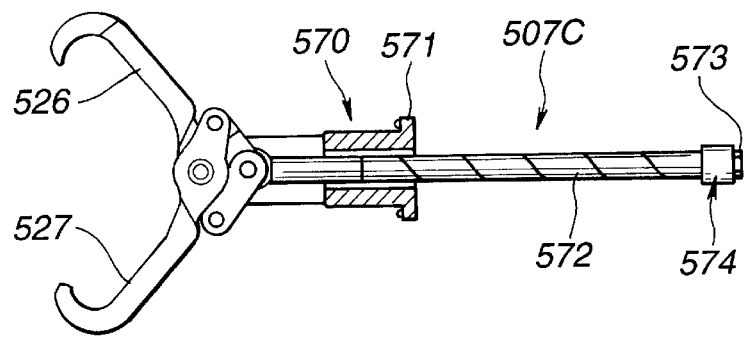
Figure 47C:
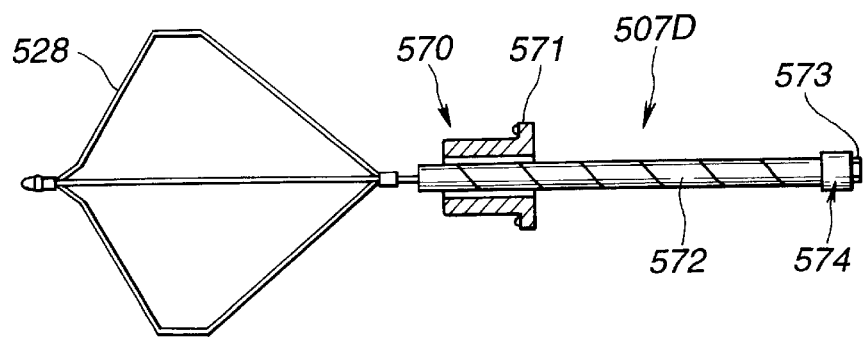
Figure 47D:
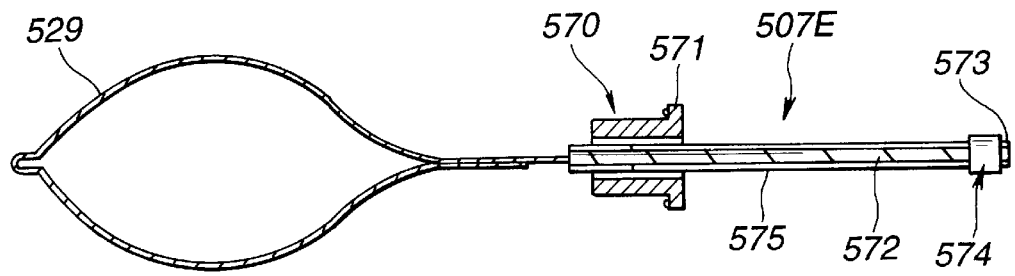

For example, as shown in FIG. 47A, when a pair of biopsy members 524 and 525 is provided as the treatment instrument, biopsy forceps 507B are formed. As shown in FIG. 47B, when a pair of sharp V-shaped clamping member 526 and 527 is provided, clamps 507C are formed. As shown in FIG. 47C, when a basket-shaped member 528 is provided, a lithotriptor 507D is formed. As shown in FIG. 47D, when a half moon-like snare 529 is provided, a diathermic snare 507E is formed.

For forming the diathermic snare 507E, the operation wire 572 is enclosed in an insulation tube 575. The distal part 509, control wire 582, and coupling member 574 are similarly insulated.

Moreover, aside from the foregoing treatment instruments, treatment instruments such as a needle, cannula, EVL, ligature, measure, dilation balloon, papillotomy knife, clip forceps, hot biopsy forceps, dispersion tube, high-frequency coagulation electrode, clip, magnetic collector, and drainage tube indwelling catheter can be employed in the treatment member 507.

Figure 48:
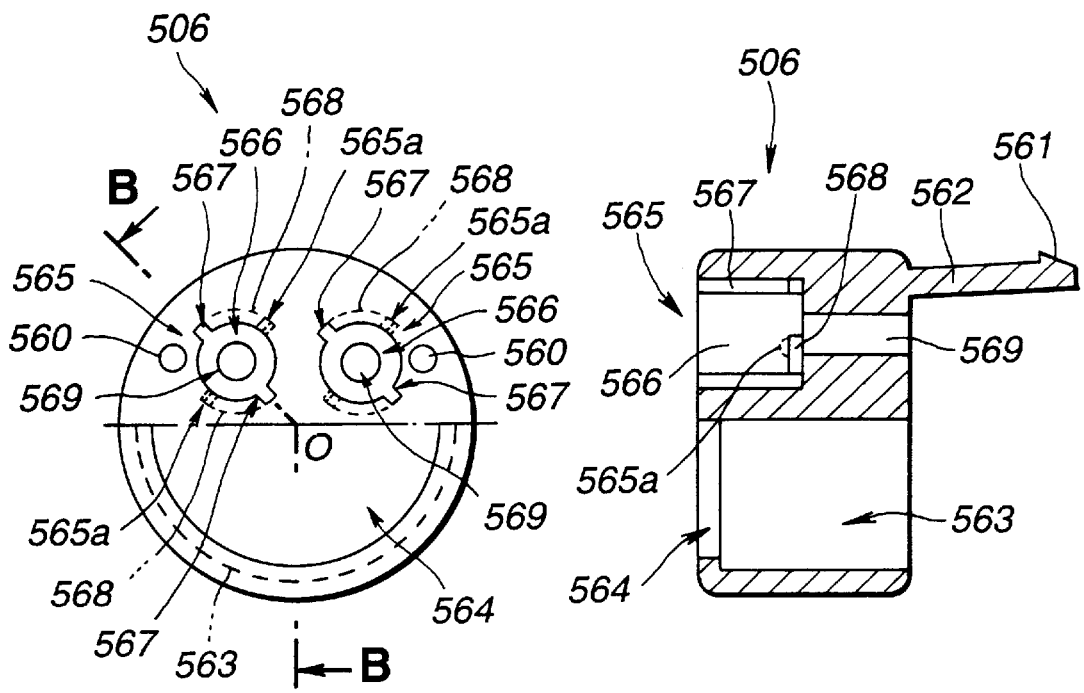

As shown in FIG. 48, the module body 506 is shaped substantially like a column. A locking claw 562 provided with a locking member 561 projects out from the back end of the module body 506. A distal convex part placement socket 563 into which a D-shaped convex part 591 of the endoscope 502 is fitted is bored into the lower half of the proximal surface of the module body 506 and has a given depth in the direction of the longitudinal axis of the module body. The distal convex part placement socket 563 opens to the outside of the module body on the distal side thereof via a D-shaped aperture 564 that is slightly smaller than the distal convex part placement socket 563.

Moreover, two treatment member coupling holes 565 are bored into the upper half of the module body. The treatment member coupling holes 565 are used to couple the treatment instrument placement member 570 to the module body 506 in a freely detachable fashion. The treatment member coupling holes 565 are each composed of a member placement socket 566 bored in the distal surface of the module body 506 in the direction of the longitudinal axis, guide grooves 567 recessed from the member placement socket 566 and designed to guide the locking portions 571 of the treatment instrument placement member 570 to the bottom of the member placement socket 566, and locking grooves 568 which are provided at the interior-most surfaces of the proximal surfaces of the member placement socket 566 as indicated with dashed lines in the drawing and in which the dilated locking portions 571 are placed within 90° clockwise with respect to the guide grooves 567 that serve as cardinal points. The member placement socket 566 communicates with the outside of module body 506 on the proximal side of the module body via a through hole 569 whose center axis is aligned with that of the member placement socket 566.

A fitting notch 565a provides means to check for proper attachment and extends in a direction orthogonal to the center axis is formed at positions angled 90° from the cardinal points. The fitting notch 565a is bored into the upper sides of the locking grooves 568. The convex parts 571a of the locking portions 571 are fitted into the fitting notches 565a.

Reference numeral 560 denotes an identification marker.

Furthermore, the treatment member 507 is provided with an identifying means. For example, each of the treatment instrument placement members 570 shown in FIGS. 46, 47A, 47B, 47C, and 47D is, as a whole, provided with a mark or color indicating a treatment instrument.

For example, each treatment instrument placement member 570 may be partly colored or marked according to whether or not the treatment member 507 is designed for diathermy. Additionally, each treatment instrument placement member 570 may be provided with a color or mark which serves as a mate identifying means in order to indicate whether the treatment members 507 can be fitted into the two treatment member coupling holes 565 and used simultaneously.

Figure 49:
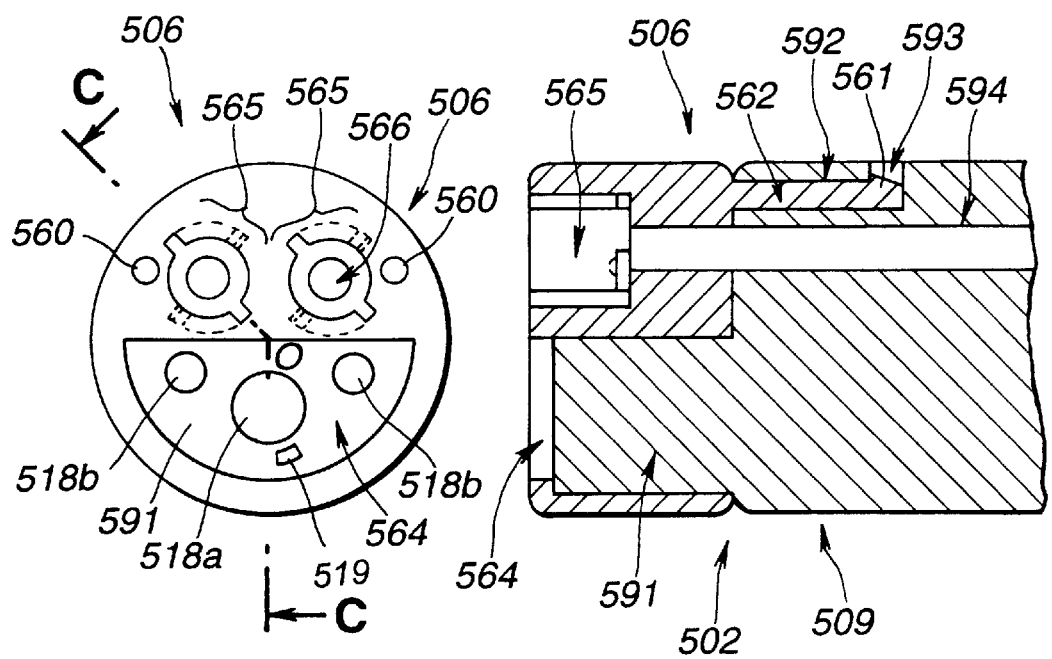

As shown in FIG. 49, a guide hole 592, through which the locking claw 562 projecting from the back end of the module body 506 is inserted, is bored in the distal part 509 of the endoscope 502. A locking recess 593 extending in a direction orthogonal to the center axis of the guide hole 592 is bored at the proximal end of the guide hole 592.

Moreover, two wire passage holes 594, through which the control wire 582 extending from the endoscope-side connecting tool 508 is provided, are bored in the distal part 509 so that the wire passage holes 594 will communicate with the through-holes 569 in the module body 506.

To attach the module body 506 to the distal part 509 of the endoscope 502, the convex part 591 is aligned with the convex part placement socket 563 and the locking claw 562 is aligned with the guide hole 592. The module body 506 and distal part 509 are then brought together in the direction of the longitudinal axis. The convex part 591 is then fitted into the convex part placement socket 563, and the locking member 561 of locking claw 562 is fitted into the locking recess 593. Thus, the module body 506 is united with the distal part 509.

To detach the module body, a releasing jig that is not shown is used to readily separate the module body 506 from the distal part 509.

Moreover, an objective lens 518a, illumination lenses 518b, and an opening of an aeration/perfusion nozzle 519 through which the objective lens 518a can be aerated or perfused are mounted in the distal surface of the D-shaped convex part 591 of the distal part 509. The objective lens 518a, illumination lenses 518b, and aeration/perfusion nozzle 519 are arranged to be opposed to a D-shaped opening 564 in module body 506.

A signal cable extending from a solid-state imaging device, which is not shown, located on the image plane of the objective lens 518a, light guides, which are not shown, opposed to the back ends of the illumination lenses 518b, and an aeration/perfusion tube, which is not shown, communicating with the aeration/perfusion nozzle 519 extend to the connector 514 by way of the insertion unit 511, and universal cord 513.

Incidentally, the module body 506 and the treatment instrument placement member 570 of the treatment member 507 are made of, for example, a metallic material permitting thermal sterilization such as stainless steel, aluminum, nickel, copper pyrite, titanium, iron, phosphor bronze, or tungsten, or a resin material such as polysulfide, polyphenylsulfide, polyethermide, polytetrafluoroethylene (PTFE), tetrafluoroethylene, perfluoroalkoxylethylene (PFA), tetrafluoroethylene propylene hexafluoride (FEP), polyacetal (POM), or polyether ether ketone (PEEK).

Moreover, the module body 506 or treatment instrument placement member 570 may be made of an inexpensive resin material such as polyolefine, polycarbonate, ABS, polyamide, vinyl chloride, latex, or natural rubber. The module body 506 and/or treatment instrument placement member 570 may thus be designed to be disposable.

Figure 50A:
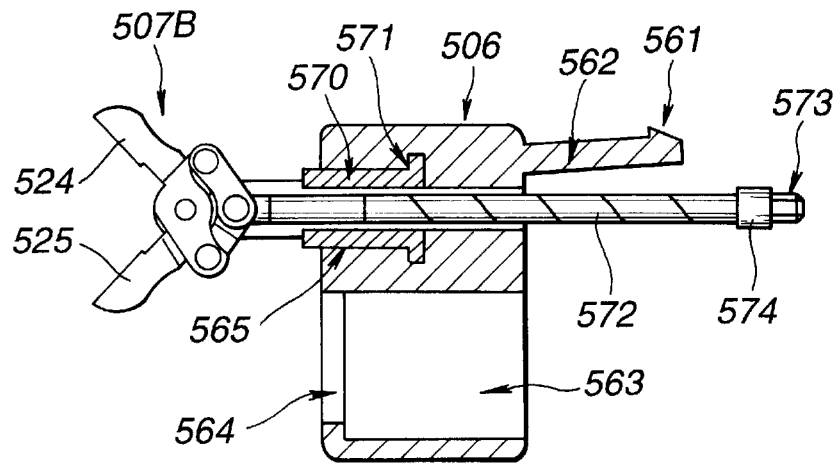
FIGS. 50A to 50C are diagrams for explaining states attained in the course of attaching a module body having a treatment member mounted therein to the distal part of an endoscope according to the sixteenth embodiment.
Figure 50B:
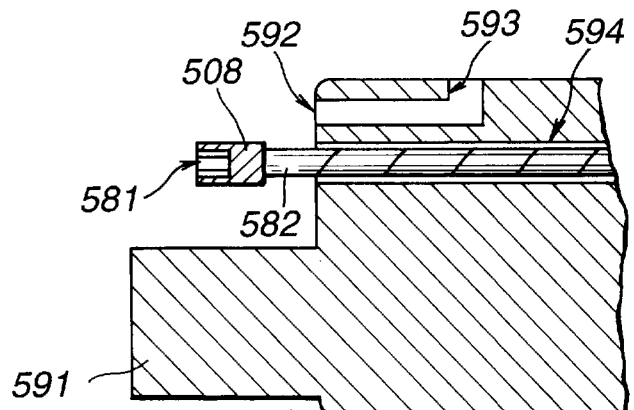
Figure 50C:
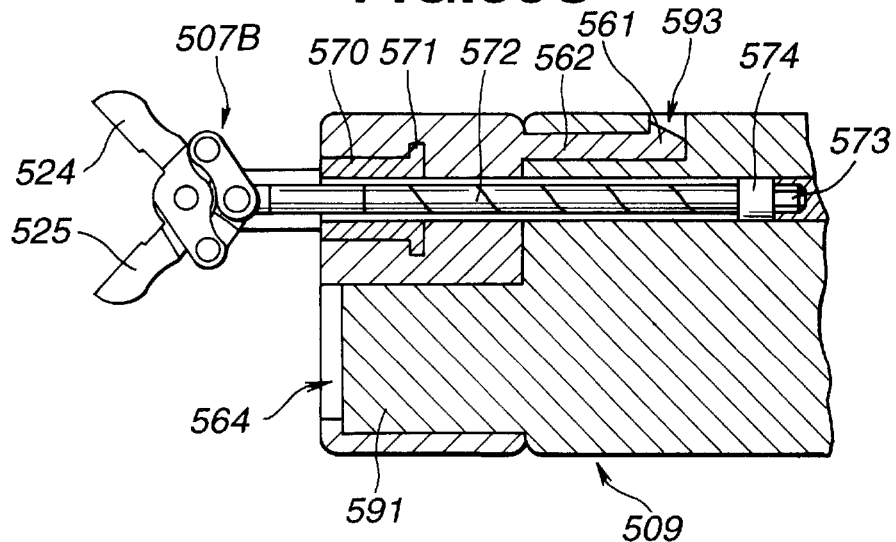

Referring to FIGS. 50A to 50C, the procedure of mounting the treatment member 507 in the module body 506 and the procedure of attaching the module body 506 having the treatment member 507 mounted therein to the endoscope 502 will be described below.

First, for example, the biopsy forceps 507B formed by affixing the pair of biopsy members 524 and 525 to one end of the operation wire 572 is mounted in the module body 506. At this time, the locking portions 571 of the treatment placement member 570 are aligned with the guide grooves 567 included in the treatment member coupling hole 565 in the module body 506. The treatment instrument placement member 570 is inserted until it abuts at the proximal surface of the guide grooves 567 and member placement socket 566. When the treatment instrument placement member 570 hits the proximal surface, it is turned 90° clockwise. The convex parts 571a of the locking portions 571 are fitted into the fitting notches 565a. The treatment instrument placement member 570 is, as shown in FIG. 50A, securely placed at the appropriate position in the module body 506.

Thereafter, the male screw portion 573 of the coupling member 574 is fixed to the proximal end of the operation wire 572 extending from the biopsy forceps 507B shown in FIG. 50A is engaged with the female screw 581 threaded in the endoscope-side connecting tool 508 placed in the wire passage hole 594 bored in the distal part 509 of the endoscope 502 shown in FIG. 50B. This causes the operation wire 572 and control wire 582 to be securely coupled to each other. The movement of advancement or withdrawal transmitted to the control wire 582 by manipulating the handle 510 (FIG. 45) is then transmitted to the operation wire 572.

Thereafter, the convex part 591 is aligned with the convex part placement socket 563 and the locking claw 562 is aligned with the guide hole 592. The module body 506 and the distal part 509 are then united with each other. This causes the convex part 591 to be locked in the convex part placement socket 563, and the locking member 561 of the locking claw 562 to be fitted into the locking recess 593. Consequently, the module body 506 having the biopsy forceps 507B mounted therein is, as shown in FIG. 50C, securely attached to the distal part 509.

The control wire 582 is advanced or withdrawn by manipulating the handle 510 mounted on the operation unit 512 of the endoscope 502. With the movement of the control wire 582, the operation wire 572 is advanced or withdrawn to cause the biopsy forceps 507B to open or close. A desired biopsy procedure can then be performed.

To remove the treatment instrument placement member 570 from the module body 506, the treatment instrument placement member 570 is turned 90° counterclockwise, and then pulled out of the treatment member coupling hole 565.

In this embodiment, two treatment member coupling holes 565 are bored in the module body 506. The module body 506 having up to two treatment members 507 mounted therein can be attached to the distal part 509 of the endoscope 502 for use. For example, the clamps 507C and diathermic snare 507E may be paired in order to conduct a strip biopsy procedure.

Moreover, in this embodiment, the number of treatment coupling holes 565 is two. Alternatively, the number of treatment member coupling holes provided may be any number equal to or larger than one.

Furthermore, each treatment member 507 may be alternately mounted in a plurality of different module bodies 506 in a manner in which it can be dismounted freely. The identifier markers 560 near the treatment member coupling holes 565 on the distal surfaces of the module bodies 506 are therefore colored or marked according to the colors or marks on the treatment instrument placement members 570 of the treatment members 507, whereby incorrect attachment of the treatment members 507 is prevented.

For example, to distinguish among the plurality of module bodies 506, the module bodies may be entirely painted in different colors or marked in a mutually distinguishing manner.

Figure 51A:
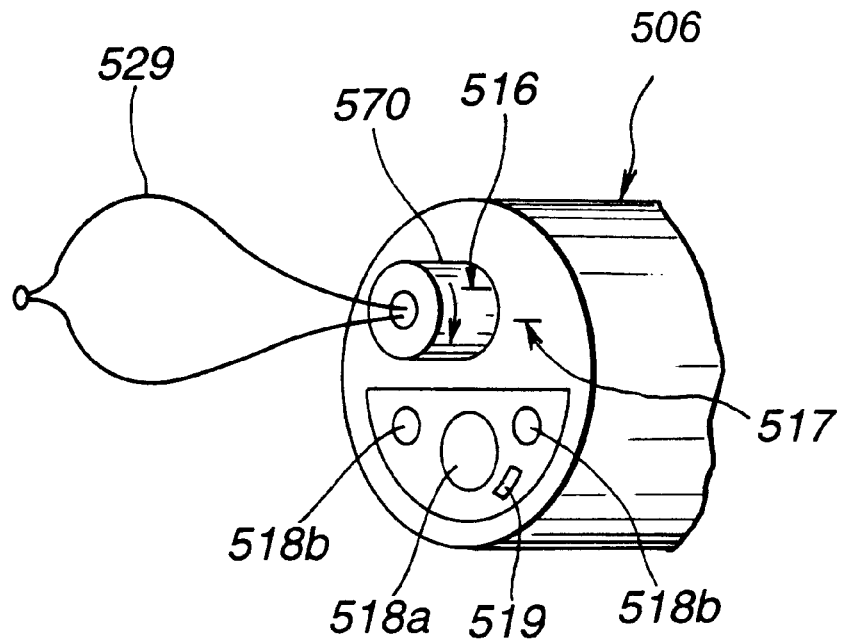
FIGS. 51A and 51B are diagrams showing the relationship between a treatment member and module body.
Figure 51B:
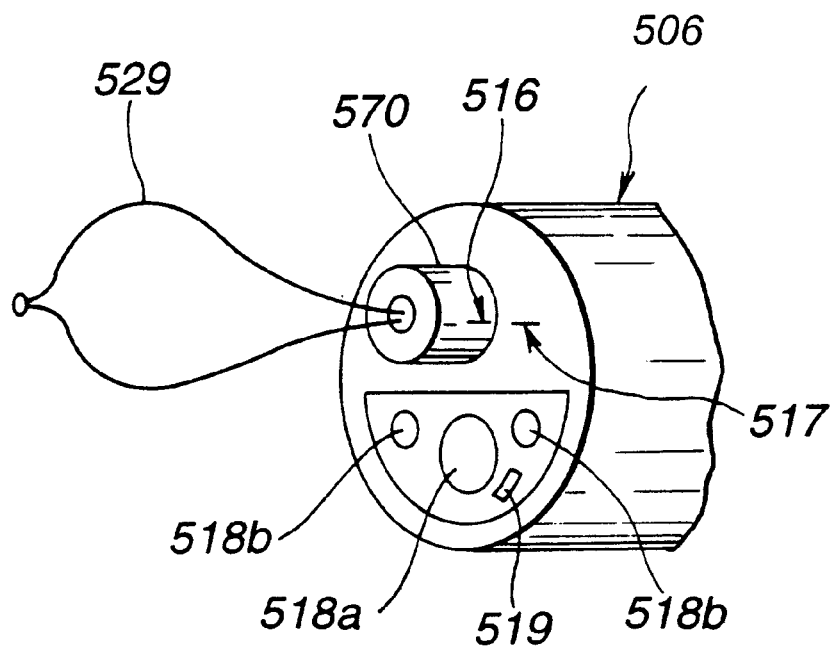

To provide a means to check if the treatment member 507 has been placed at the proper position in the module 506, a mark 516, as shown in FIGS. 51A and 51B, may be inscribed on the treatment instrument placement member 570. An initial state in which the mark 516 is not aligned with a mark 517 is shown in FIG. 51A. The treatment instrument placement member 570 is then shifted to a state in which the marks 516 and 517 are aligned with each other, as shown in FIG. 51B. It is thus confirmed that the treatment member 507 has been placed at the proper position in the module body 506.

As mentioned above, a treatment instrument placement member included in a treatment member can be removably inserted into a treatment member coupling hole in an endoscope module. A plurality of treatment members can be used in combination with one endoscope module. The number of variations thus achievable with a set of treatment members and an endoscope module become more abundant. This results in an endoscope system capable of performing a variety of techniques.

Because the treatment instrument placement member included in the treatment member can be removably inserted into the treatment member coupling hole in the endoscope module, the efficiency in cleaning or sterilizing the endoscope module and treatment member for reuse will improve greatly.

Furthermore, the treatment instrument placement member and endoscope module can each be constructed to be reusable with various members. Alternatively, the treatment instrument placement member alone may be designed to be disposable, the endoscope module alone may be designed to be disposable, or both the treatment instrument placement member and endoscope module may be designed to be disposable. This will improve after-use practicality.

Referring to FIGS. 52 and 53, a seventeenth embodiment of the present invention will be described below.

In this embodiment, the two treatment member coupling holes 565 which are juxtaposed in the upper half of the drawing in the sixteenth embodiment are aligned in tandem in FIG. 52 with an objective lens 518a between them. Moreover, in the sixteenth embodiment, the treatment member 507 is powered by advancing or withdrawing the control wire 582. In this embodiment, power is supplied by means of an electric actuator such as a solenoid or motor. In this embodiment, solenoids 531 are employed. The other components are identical to those of the sixteenth embodiment. The same reference numerals will be assigned to the same members. The description of those members will therefore be omitted.

To be more specific, as shown in FIG. 52, when electrical contacts 535 formed on the proximal end of the module body 506 come into contact with electrical contacts, which are not shown, formed on the distal side of the distal part 509, the solenoids 531 are powered via electric cables 534. This causes shafts 532 to advance or withdraw. A coupling member 533 is fixed to the distal end of each of the shafts 532. The coupling member 533 has, as shown in FIG. 53B, the same structure as the treatment member coupling hole 565.

Moreover, the proximal part 576 of the treatment member 507 has, as shown in FIG. 53A, the same structure as the proximal part of the treatment instrument placement member 570. The proximal part 576 and coupling member 533 can be, like the aforesaid treatment instrument placement member 570 and treatment member coupling hole 565, coupled to each other so that they can be freely detached.

As mentioned above, treatment members are aligned in tandem with an objective lens between them. The treatment members become symmetrical to each other within a field of view. This leads to improved workability for a treatment procedure.

Moreover, an electric actuator such as a solenoid is used to transmit power. This alleviates the load incurred by an operator. Upon coupling the endoscope module to the distal endoscope part, the electric contact conducts. This greatly simplifies the task of coupling the endoscope module to the distal endoscope part.

Figure 54:
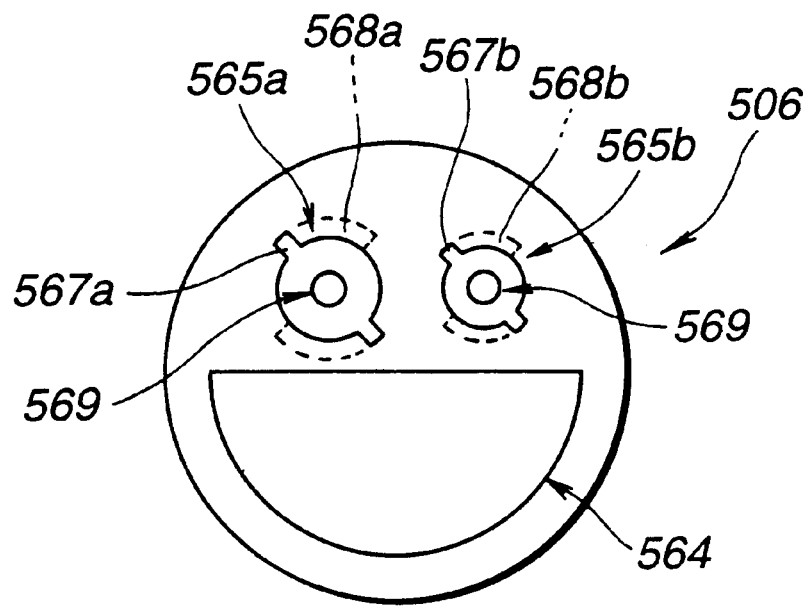
FIG. 54 is a diagram for explaining the structure of an applied example of a module body of the present invention.

As presented with the sixteenth and seventeenth embodiments, the two treatment member coupling holes 565 are bored into body member 506. In this case, as shown in FIG. 54, only the through-holes 569 of a first treatment member coupling hole 565a and second treatment member coupling hole 565b may have the same dimension. The dimension of placement sockets 566a and 566b, guide grooves 567a and 567b, and locking grooves 568a and 568b may be mutually different.

Figure 55:
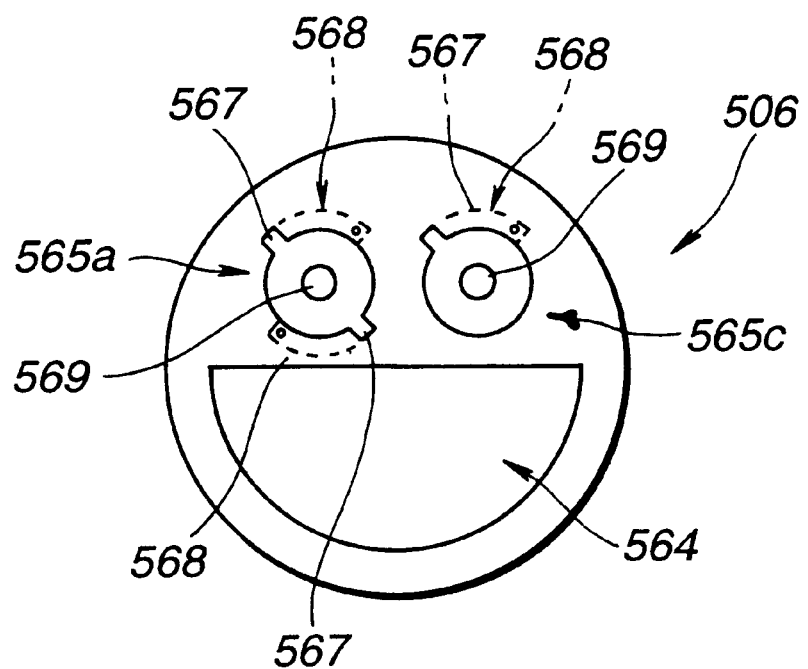
FIG. 55 is a diagram for explaining another structure of an applied example of a module body of the present invention.

Moreover, as shown in FIG. 55, a treatment member coupling hole 565c having only one guide groove 567 instead of the guide grooves 567a may be provided. In this case, the treatment instrument placement member 570 has a locking portion 571 associated with the treatment member coupling hole 565c.

When the placement socket, guide grooves, or locking grooves are mutually differentiated in size or shape, improper attachment can be prevented more effectively during coupling of an endoscope module and treatment member. Thus, for example, a diathermic treatment member can be more reliably prevented from being incorrectly attached in place of a treatment member that is not designed for diathermy or vice versa. This feature of this embodiment leads to greatly improved safety.

Figure 56:
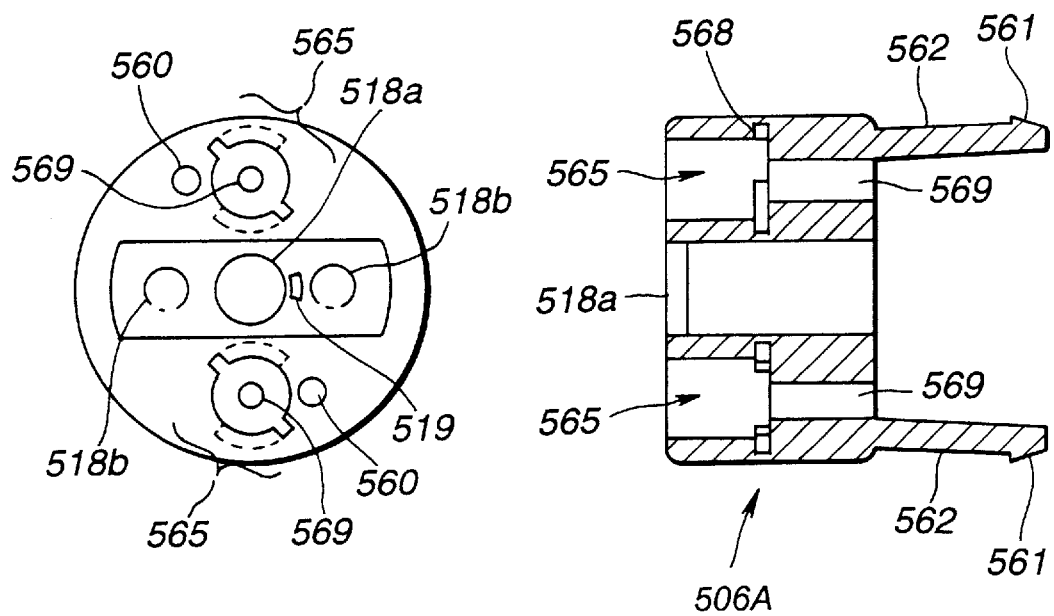
FIG. 56 is a diagram for explaining another structure of an applied example of a module body of the present invention.

Moreover, the two treatment member coupling holes 565 which are juxtaposed in one direction in the module body 506 in the sixteenth embodiment are like those shown in FIG. 52, aligned in tandem in a module body 506A of this embodiment with the objective lens 518a between them, as shown in FIG. 56.

The two treatment member coupling holes 565a and 565b in the module body 506 may be, as shown in FIG. 54, mutually different in size. Preferably, however, the sizes of the two treatment member coupling holes 565 in the module body 506A are identical to those in the module body 506. This permits interchangeable use of the module bodies among the treatment member coupling holes.

As such, the treatment members 507 shown in FIGS. 46 to 47D can be interchangeably inserted into the treatment member coupling holes 565. At this time, the module body 506A and module body 506 of the sixteenth embodiment of FIGS. 48 and 49 are mutually different in the positions of the treatment member coupling holes 565. To readily distinguish between the module bodies, inscribing an identification symbol on their surfaces or painting them in different colors is adopted as a module identifying means. Moreover, the module body 506A is also provided with a proper attachment checking means. Moreover, the module body 506A is also provided with a proper attachment checking means.

As mentioned above, different endoscope modules are formed so that treatment member coupling holes in the endoscope modules will match the treatment instrument placement members included with different treatment members. This permits interchangeable use of treatment members among a plurality of endoscope modules. Consequently, the number of variations achievable with a set of treatment members and an endoscope module become more abundant. This results in and endoscope system capable of performing a wide variety of techniques.

Referring to FIGS. 57A to 57D, an eighteenth embodiment of the present invention will be described below.

Figure 57A:
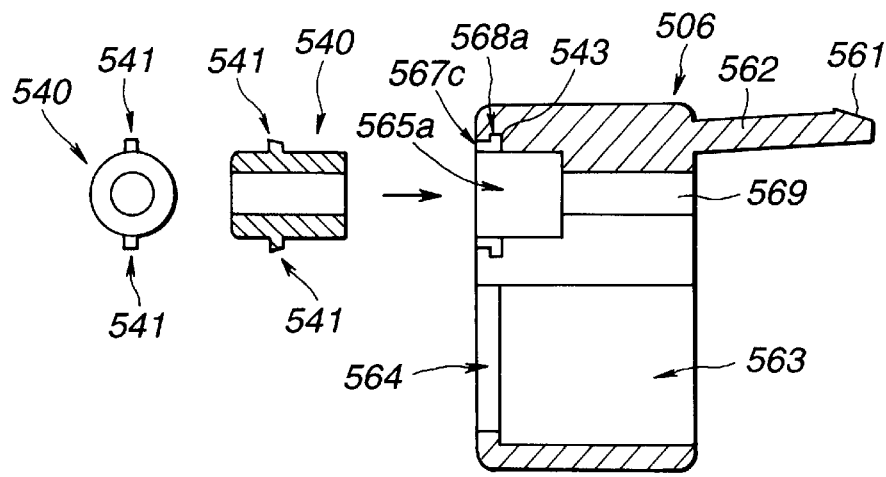
FIGS. 57A to 57D are diagrams for explaining an eighteenth embodiment of the present invention.
Figure 57B:
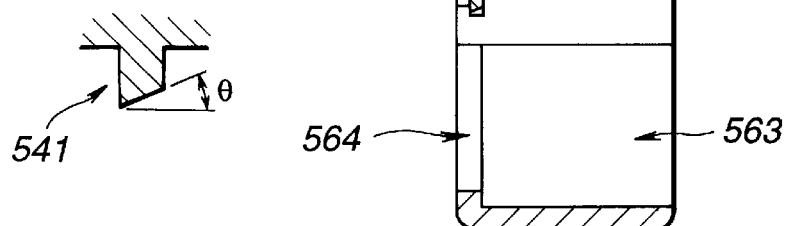

As shown in FIGS. 57A and 57B, a treatment instrument placement member 540 of this embodiment is made of an inexpensive resin material, for example, polyolefine, polycarbonate, ABS, polyamide, vinyl chloride, latex, or natural rubber. Locking portions 541 are located at substantially intermediate positions on the treatment instrument placement member 540. As shown in FIG. 57B, the projecting locking portions 541 have the distal sides thereof made longer than the proximal sides thereof, such that the radial surfaces thereof are angled from the horizontal by an angle Θ. Locking grooves 543 are provided in a module body 506 at positions which coincide with the radial positions of the locking portions 541. The other components are identical to those of the sixteenth embodiment. The same reference numerals will be assigned to the same members. The description of those members will therefore be omitted.

Due to the foregoing structure, to mount the treatment instrument placement member 540 in the module body 506, the treatment instrument placement member 540 should merely be pushed in the axial direction. The locking portions 541 are then fitted into the locking grooves 543. Thus, coupling the module body 506 to the treatment instrument placement member 540 is completed.

Figure 57C:
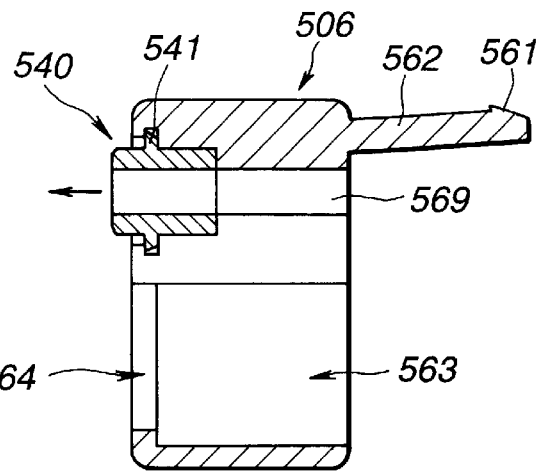
Figure 57D:
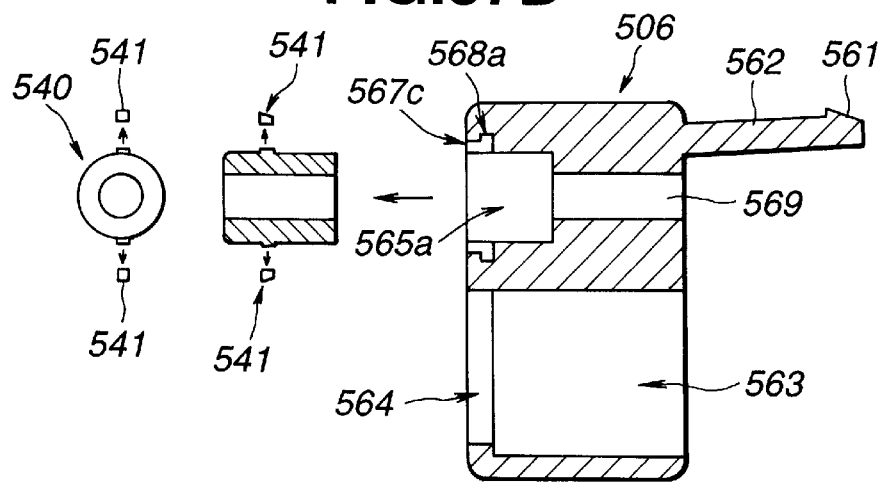

Moreover, when the treatment instrument placement member 540 is dismounted from the module body 506, the treatment instrument placement member 540 is, as shown in FIG. 57C, pulled out of the module body 506. At this time, the locking portions 541 are broken, as shown in FIG. 57D. This disables reuse of the treatment instrument placement member 540.

As mentioned above, a treatment instrument placement member of a treatment member is made of a resin material The treatment instrument placement member can be mounted in an endoscope module by merely fitting locking portions into locking grooves. This permits easy attachment of the treatment member to the endoscope module.

Moreover, when the treatment instrument member is dismounted from the endoscope module, the locking portions are broken. The treatment instrument placement member can therefore be designed to be disposable. Thus, infection deriving from reuse of the treatment instrument placement member can be avoided. Additionally, the task of cleaning and sterilizing equipment after performing a treatment procedure can be efficiently reduced.

According to the present invention, it will be apparent that a wide range of embodiments can be constructed based on the disclosure without departure from the spirit and scope of the invention. This invention will be limited by the appended claims but will not be restricted by any specific embodiments discussed herein.

What is claimed is:

1. An endoscope system comprising:
   a plurality of endoscope modules having different treating elements mounted therein; and
   an endoscope to which said endoscope modules can be attached, said endoscope including
   an insertion unit having a distal part,
   a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, and
   an operation unit for handling a treating element mounted in an endoscope module attached to said distal part, said operation unit having a locking mechanism for locking a position of a treating element mounted in an endoscope module attached to said distal part.

2. An endoscope system comprising:
   a plurality of endoscope modules having different treating elements mounted therein;
   an endoscope to which said endoscope modules can be attached, said endoscope including
   an insertion unit having a distal part,
   a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism,
   an operation unit for handling a treating element mounted in an endoscope module attached to said distal part,
   an operation channel extending along the length of the endoscope, and a suction channel extending along the length of the endoscope; and
   an operation force transmitter disposed in said operation channel for coupling said operation unit to a treating element mounted in an endoscope module to be attached to said distal part.

3. An endoscope system comprising:
   a plurality of endoscope modules having different treating elements mounted therein;
   an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, an operation unit for handling a treating element mounted in an endoscope module attached to said distal part, and a channel extending along the length of the endoscope; and an operation force transmitter disposed in said channel for coupling said operation unit to a treating element mounted in an endoscope module to be attached to said distal part, wherein said channel in which said operation force transmitter is disposed also serves as a suction channel in said endoscope.

4. An endoscope system comprising:

a plurality of endoscope modules having different treating elements mounted therein;

an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, and an operation unit for handling a treating element mounted in an endoscope module attached to said distal part; and an operation force transmission wire for coupling said operation unit to a treating element mounted in an endoscope module to be attached to said distal part, said transmission wire including a connecting member located in said operation unit of said endoscope for connecting said transmission wire to a treating element mounted in an endoscope module to be attached to said distal part.

5. An endoscope system comprising:

a plurality of endoscope modules having different treating elements mounted therein;

an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, and an operation unit for handling a treating element mounted in an endoscope module attached to said distal part; and an operation force transmitter for coupling said operation unit to a treating element mounted in an endoscope module to be attached to said distal part, wherein said operation force transmitter is capable of transmitting a torque.

6. An endoscope system comprising:

a plurality of endoscope modules having different treating elements mounted therein;

an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, an operation unit for handling a treating element mounted in an endoscope module attached to said distal part, and an operation channel extending along the length of the endoscope; and an operation force transmitter for coupling said operation unit to a treating element mounted in an endoscope module to be attached to said distal part, wherein said operation force transmitter includes a transmission wire, a piston fixed along the length of said transmission wire so as to be in close contact with the inner circumference of said operation channel, a liquid to be poured into a space defined by said piston and said operation channel, and a liquid compression means for compressing the liquid.

7. An endoscope system comprising:

a plurality of endoscope modules having different treating elements mounted therein, each endoscope module including a first coupling mechanism formed thereon; and an endoscope to which said endoscope modules can be attached, said endoscope including an insertion unit having a distal part, and a second coupling mechanism located at said distal part of said insertion unit, said second coupling mechanism being exchangeably attachable to each of said plurality of endoscope modules, such that said first coupling mechanism in each endoscope module matingly corresponds to said second coupling mechanism, wherein said plurality of endoscope modules having said different treating elements are interchangeably attachable to said distal part of said insertion unit via said first and second coupling mechanisms, and wherein at least one of said first and second coupling mechanisms is a magnet.

8. An endoscope system comprising:

a plurality of endoscope modules having different treating elements mounted therein, each endoscope module including a first coupling mechanism formed thereon; and an endoscope to which said endoscope modules can be attached, said endoscope including an insertion unit having a distal part; and a second coupling mechanism located at said distal part of said insertion unit, said second coupling mechanism being exchangeably attachable to each of said plurality of endoscope modules such that said first coupling mechanism in each endoscoite module matingly corresponds to said second coupling mechanism, wherein said plurality of endoscope modules having said different treating elements are interchangeably attachable to said distal part of said insertion unit via said first and second coupling mechanism, and wherein said first coupling mechanism includes an elastic member and said second coupling mechanism includes a hard member on said distal part of said endoscope.

9. An endoscope system comprising:

a plurality of endoscope modules having different treating elements mounted therein; and an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, and an operation unit which is capable of moving a treating element mounted in an endoscope module attached to said distal part to a position within a field of view permitted by said endoscope so that the treating element can be observed.

10. An endoscope system comprising:

a plurality of endoscope modules each including a body member and a treating element mounted in the respective body member, wherein each of the treating elements are mutually different from each other; and an endoscope to which said endoscope modules can be attached, said endoscope including an insertion unit having a distal part, a coupling mechanism located at said distal part of said insertion unit said coupling mechanism being exchangeably attachable to each of said plurality of endoscope modules, wherein said plurality of endoscope modules having said different treating elements are interchangeably attachable to said distal part of said insertion unit via said coupling mechanism, and wherein said distal part of said endoscope is covered by said body member of a corresponding endoscope module when said corresponding endoscope module is attached to said distal part.

11. An endoscope system according to claim 10, wherein at least one of said endoscope modules further includes a cover made of a transparent material, and wherein said endoscope further includes an observation window and an illumination window in the distal surface thereof such that when said distal part of said insertion unit is covered with said body member, said cover is placed in front of said observation window and said illumination window.

12. An endoscope system according to claim 11, wherein said cover further includes a light interceptor positioned thereon such that when said cover is placed in front of said observation window and said illumination window, said light interceptor is placed around the perimeter of said illumination window.

13. An endoscope system according to claim 12, wherein said light interceptor has an annular shape.

14. An endoscope system according to claim 10, further comprising a locking member for restraining said body members from moving in the direction of the longitudinal axis of said endoscope.

15. An endoscope system according to claim 10, wherein said body members each include a locking member for holding and locking said endoscope in a body cavity when an endoscope module is attached to said endoscope.

16. An endoscope system according to claim 15, wherein said locking member is a balloon capable of being dilated to a diameter of a body cavity in which said endoscope is to be held.

17. An endoscope system comprising:

a plurality of endoscope modules having different treating elements mounted therein; and an endoscope to which said endoscope modules can be attached, said endoscope including an insertion unit having a distal part, and a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, wherein said distal part of said insertion unit includes a convex part, and wherein said convex part includes an observation window, an illumination window, an aeration/perfusion nozzle, and a treatment channel.

18. An endoscope system according to claim 17, wherein each of said endoscope modules includes an inner space portion into which said convex part is fitted.

19. An endoscope system according to claim 17, wherein at least one of said endoscope modules has an aeration/perfusion nozzle.

20. An endoscope system according to claim 17, wherein said endoscope further includes electrical insulation on a surface of said endoscope which contacts an endoscope module when attached thereto.

21. An endoscope system according to claim 17, wherein at least part of at least one of said endoscope modules is insulated.

22. An endoscope system according to claim 21, wherein the outer circumference of said at least one of said endoscope modules is the insulated part.

23. An endoscope system comprising:

a plurality of endoscope modules having different treating elements mounted therein, each endoscope module being provided with an identifier for identifying the treating element associated with said each endoscope module; and an endoscope to which said endoscope modules can be attached, said endoscope including an insertion unit having a distal part, a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism.

24. An endoscope system according to claim 23, wherein each said identifier is located at a position on an outer circumference of the corresponding endoscope module at which said identifier can be easily viewed.

25. An endoscope system according to claim 23, wherein each said identifier is capable of being viewed when the corresponding endoscope module is attached to said endoscope.

26. An endoscope system according to claim 23, wherein each said identifier is a color indicator placed on at least part of the outer circumference of the corresponding endoscope module.

27. An endoscope system according to claim 23, wherein each said identifier is a plurality of characters or a symbol inscribed on the outer circumference of the corresponding endoscope module.

28. An endoscope system comprising:

a plurality of groups each comprised of an endoscope and a corresponding plurality of endoscope modules used in combination with the endoscope, wherein each of said groups are provided with a matching system for determining if a particular endoscope module and endoscope combination is possible, wherein the endoscope modules of each plurality thereof have mutually different treating elements mounted therein, and wherein each endoscope includes
an insertion unit having a distal part, and
a coupling mechanism located at said distal part of said insertion unit, said coupling mechanism being exchangeably attachable to each endoscope module in the corresponding plurality of endoscope modules, wherein said corresponding plurality of endoscope modules having said different treating elements are interchangeably attachable to said distal part of said insertion unit via said coupling mechanism.

29. An endoscope system according to claim 28, wherein said matching system includes corresponding sets of symbols or characters inscribed on the outer surfaces of the endoscope modules and endoscopes.

30. An endoscope system according to claim 28, wherein said matching system is defined by painting at least part of the outer surfaces of the endoscope modules and endoscopes in colors associated with their respective model names.

31. An endoscope system according to claim 28, wherein said matching system provides a different attachment interface diameter for each group of endoscope modules and endoscopes.

32. An endoscope system according to claim 28, wherein each of said endoscope modules and endoscopes has a connection portion at which each endoscope module is to be connected to a corresponding endoscope, and wherein said matching system is defined by different shapes of the connection portions, wherein each of said groups corresponds to a mutually different model of endoscope, and each shape corresponds to a respective one of the different models.

33. An endoscope system according to claim 28, wherein when an endoscope module is attempted to be incorrectly attached to a mismatched endoscope, said matching system physically prevents connection between the mismatched endoscope module and endoscope.

34. An endoscope system according to claim 28, wherein said matching system includes said coupling mechanism at the distal part of the insertion unit of each endoscope.

35. An endoscope system comprising:

a plurality of endoscope modules having different treating elements mounted therein; and a plurality of endoscopes to which each endoscope module can be attached, wherein each of said endoscopes is of a mutually different type from the others and includes
an insertion unit having a distal part,
a locking member at the distal part of the insertion unit, and
a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism, wherein each endoscope module includes a fitting member capable of being fitted on said locking member of each of said endoscopes.

36. An endoscope system according to claim 35, wherein each of said fitting members is fitted on each said locking member in the direction of the longitudinal axis of the insertion unit of the respective endoscope.

37. An endoscope system according to claim 36, wherein the portions of the distal part of each endoscope and of each endoscope module which contact each other upon being fitted together in the direction of the longitudinal axis of the insertion unit of the respective endoscope are located near said locking member and fitting member, respectively.

38. An endoscope system according to claim 37, wherein said portion of said each endoscope which contacts the endoscope module fitted therewith is the outer circumference of the distal part of the insertion unit of said each endoscope.

39. An endoscope system according to claim 37, wherein each endoscope further includes a suction channel extending through the length thereof, and said portion of said each endoscope which contacts the endoscope module fitted therewith is the inner circumference of the suction channel extending through said each endoscope.

40. An endoscope system according to claim 39, wherein each said fitting member is provided with a projection such that when any one of said endoscope modules is fitted to any one of said endoscopes, the projection of the respective fitting member of said endoscope module fitted to said endoscope abuts on said suction channel in said endoscope.

41. An endoscope system according to claim 40, wherein each said projection has a deformable portion capable of elastically deforming radially relative to the axis of the direction of attachment.

42. An endoscope system according to claim 36, wherein each said locking member is formed by a concave part of the outer circumference of the distal part of the respective endoscope.

43. An endoscope system according to claim 42, wherein said fitting member is formed by a deforming portion capable of elastically deforming radially relative to the axis of the direction of attachment.

44. An endoscope system according to claim 36, wherein each endoscope module includes a coupling member for coupling said each endoscope module to a driving means for driving said treating element included in the respective endoscope module, and further includes a fitting member located near said coupling member.

45. An endoscope system according to claim 44, wherein each said fitting member includes a deforming portion capable of elastically deforming radially relative to the axis of the direction of attachment.

46. An endoscope system comprising:

a plurality of endoscope modules having different treating elements mounted therein;

an endoscope to which said endoscope modules can be attached, said endoscope including
an insertion unit having a distal part, and
a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism; and an attached state checking means to indicate whether a selected one of said endoscope modules is attached to said endoscope properly.

47. An endoscope system according to claim 46, wherein said attached state checking means is an indicator on at least one of said endoscope and said plurality of endoscope modules painted in a color different from a color of portions surrounding said indicator.

48. An endoscope system according to claim 47, wherein said attached state checking means indicates whether a positional relationship between an endoscope module and said endoscope in an attached state is proper, in which the positional relationship is in at least one direction of the direction of the axis of the insertion unit and the circumferential direction of the insertion unit.

49. An endoscope system according to claim 47, wherein said indicator is located on either said plurality of endoscope modules or said endoscope such that when a selected one of said endoscope modules and said endoscope are attached to each other properly, said indicator is covered.

50. An endoscope system according to claim 47, wherein said indicator is placed on each of said endoscope modules and said endoscope such that when one of said endoscope modules is indicated to be properly attached to said endoscope, said indicators placed on said attached endoscope module and said endoscope are juxtapose.

51. An endoscope system according to claim 47, wherein said indicator is placed on one of said endoscope modules and said plurality of modules endoscope, and the other of said endoscope modules and said endoscope modules an instructing member placed thereon, such that when the indicator and instructing member are opposed to each other, a selected one of said endoscope modules and said endoscope are indicated to be attached to each other properly.

52. An endoscope system comprising:
a plurality of endoscope modules, each endoscope module including a module body and a treatment instrument placement member having a treating element that can be mounted in the module body in a freely discountable fashion, wherein the treating elements provided with the endoscope modules are mutually different from each other; and an endoscope to which said endoscope modules can be attached, said endoscope including
an insertion unit having a distal part,
a coupling mechanism located at said distal part of said insertion unit, said coupling mechanism being exchangeably attachable to each of said plurality of endoscope modules, wherein said plurality of endoscope modules having said different treating elements are interchangeably attachable to said distal part of said insertion unit via said coupling mechanism.

53. An endoscope system according to claim 52, wherein each said module body has a treatment member coupling hole bored therein, and the corresponding treatment instrument placement member can be removably inserted into said treatment member coupling hole bored in said module body.

54. An endoscope system according to claim 53, wherein at least one of said endoscope modules is provided with a plurality of treatment member coupling holes bored in the respective module body.

55. An endoscope system according to claim 54, wherein each said plurality of treatment member coupling holes in a respective one of said endoscope modules allows a plurality of treating elements to be mounted in the same direction in the respective module body so as to be within a field of view through said endoscope.

56. An endoscope system according to claim 54, wherein each said plurality of treatment member coupling holes in a respective one of said endoscope modules allows a plurality of treating elements to be mounted in different directions in the respective module body so as to be within a field of view through said endoscope.

57. An endoscope system according to claim 54, further comprising a plurality of treating elements which are adapted to be freely detachably mounted into said plurality of treatment member coupling holes of said respective module body, and wherein said plurality of treating elements have portions which are mutually different in structure.

58. An endoscope system according to claim 54, further comprising a plurality of treating elements which are adapted to be freely detachably mounted into said plurality of treatment member coupling holes of said respective module body, and wherein said plurality of treating elements have portions which are mutually common in structure.

59. An endoscope system according to claim 54, further comprising a plurality of treating elements which can be selectively mounted in each said module body in a freely discountable fashion.

60. An endoscope system according to claim 59, wherein each of said plurality of treating elements includes an identifying feature.

61. An endoscope system according to claim 52, further comprising a combination identifying feature for identifying whether a particular treating element may be used in combination with a particular module body.

62. An endoscope system according to claim 61, further comprising a proper attachment checking feature which indicates whether or not one of said treating elements has been mounted in an appropriate one of said module bodies properly.

63. An endoscope system according to claim 62, further comprising a mechanism usable for detachably mounting said treating elements in an appropriate one of said module bodies, and also for detachably attaching said appropriate one of said module bodies to the distal part of said endoscope.

64. An endoscope system according to claim 52, wherein said treating elements are reusable and can each be repeatedly mounted in a corresponding one of said module bodies in a discountable fashion.

65. An endoscope system according to claim 52, wherein said treating elements can each be mounted in a corresponding one of said module bodies only once so as to prevent reuse of said treating elements.

66. An endoscope system according to claim 52, wherein said treating elements can each be mounted in each of said plurality of different module bodies in a discountable fashion.

67. An endoscope system according to claim 52, further comprising an identifying feature for distinguishing between said plurality of endoscope modules.

68. An endoscope system according to claim 52, wherein each of said treating elements and said module bodies can be sterilized.

69. An endoscope system comprising:
a plurality of endoscope modules each having a body member and a treating element mounted in the respective body member;

an endoscope including an insertion unit having a distal part to which said endoscope modules can be attached; and coupling means via which said plurality of endoscope modules can be attached to said distal part of said insertion unit of said endoscope, wherein said body members of said endoscope module each has an outer configuration dimensioned so as to be substantially the same as that of said distal part of said insertion unit of said endoscope.

* * * * *